US012790331B2

(12) United States Patent
Abagyan et al.

(10) Patent No.: US 12,790,331 B2

(45) Date of Patent: Nov. 10, 2026

(54) SUBSTITUTED 1H-PYRAZOLO [4,3-C] QUINOLINES, METHODS OF PREPARATION, AND USE THEREOF

(71) Applicant: Lomond Therapeutics, Inc., San Diego, CA (US)

(72) Inventors: Ruben Abagyan, La Jolla, CA (US); Oleg D Mitkin, Khimki (RU); Vladislav Zenonovich Parchinsky, Moscow (RU); Alexei Pushechnikov, San Diego, CA (US); Alexandre Vasilievich Ivachtchenko, Hallandale Beach, FL (US); Nikolay Savchuk, San Diego, CA (US)

( * ) Notice: Subject to any disclaimer, the term of this patent is extended or adjusted under 35 U.S.C. 154(b) by 291 days.

(21) Appl. No.: 18/701,223

(22) PCT Filed: Oct. 3, 2022

(86) PCT No.: PCT/US2022/045555

§ 371 (c)(1),
(2) Date: Apr. 13, 2024

(87) PCT Pub. No.: WO2023/064133

PCT Pub. Date: Apr. 20, 2023

(65) Prior Publication Data

US 2025/0011319 A1 Jan. 9, 2025

Related U.S. Application Data

(60) Provisional application No. 63/256,260, filed on Oct. 15, 2021.

(51) Int. Cl.

| | |
|---|---|
| ***C07D 471/04*** | (2006.01) |
| ***A61K 31/4745*** | (2006.01) |
| ***A61K 31/496*** | (2006.01) |
| ***A61K 31/5377*** | (2006.01) |
| ***A61P 35/02*** | (2006.01) |

(52) U.S. Cl.

CPC ........ *C07D 471/04* (2013.01); *A61K 31/4745* (2013.01); *A61K 31/496* (2013.01); *A61K 31/5377* (2013.01); *A61P 35/02* (2018.01)

(58) Field of Classification Search

None

See application file for complete search history.

(56) References Cited

U.S. PATENT DOCUMENTS

2020/0190104 A1 6/2020 Sampson et al.

FOREIGN PATENT DOCUMENTS

WO WO2020193512 10/2020

OTHER PUBLICATIONS

CAS RN 901030-72-6 (entered into STN on Aug. 14, 2006) (Year: 2006).*

CAS RN 901030-76-0 (entered into STN on Aug. 14, 2006) (Year: 2006).*

* cited by examiner

*Primary Examiner* — Craig D Ricci

(74) *Attorney, Agent, or Firm* — Sergey Alyabyev

(57) ABSTRACT

The present invention is generally directed to inhibitors of hematopoietic progenitor kinase 1 (HPK1) and FMS-like tyrosine kinase 3 (FLT3) gene, useful in the treatment of diseases and disorders modulated by said HPK1, and FLT3 having the Formula I:

(I)

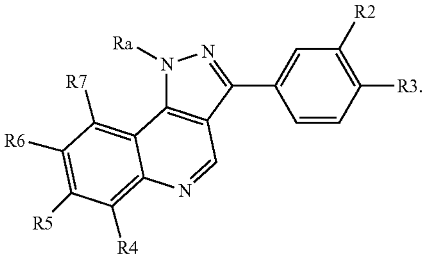

6 Claims, No Drawings

SUBSTITUTED 1H-PYRAZOLO [4,3-C] QUINOLINES, METHODS OF PREPARATION, AND USE THEREOF

CROSS-REFERENCE TO RELATED APPLICATIONS

This application claims priority to and the benefit of U.S. Provisional Patent Application Ser. No. 63/256,260 filed Oct. 15, 2021, and entitled "Substituted 1H-pyrazolo[4,3-c] quinolines, methods of their preparation, and use thereof," the disclosure of which is incorporated herein by reference in its entirety for all purposes.

FIELD OF INVENTION

The present invention is directed to novel anti-cancer agents and intermediates and their synthesis. More specifically, the present invention relates to compounds that are tyrosine kinase inhibitors, including inhibitors of FLT3 mutation-positive relapsed or refractory acute myeloid leukemia (AML), and inhibitors of hematopoietic progenitor kinase 1 (HPK1), pharmaceutical compositions comprising such compounds, methods for inhibiting of FLT3 mutation, and methods for treating of AML. The present invention also relates to novel substituted pyrazolo[4,3-c]quinolines as intermediates for the synthesis of novel anti-cancer agents disclosed herein. The invention also relates to processes for making the novel anti-cancer agents and pharmaceutical compositions comprising them.

BACKGROUND OF THE INVENTION

Discovered in 2001 imatinib was a breakthrough in targeted cancer therapy. It stimulated research on kinase inhibitors as a key class of drugs in oncology, which has proven to be the predominant field of use for kinase inhibitors. There are currently 71 small-molecule kinase inhibitors (SMKIs) approved by the FDA and an additional 16 SMKIs approved by other regulatory agencies. [M M. Attwood et al. *Trends in kinase drug discovery: targets, indications and inhibitor design. Nat. Rev. Drug. Discov.* 2021 Aug. 5. doi: 10.1038/s41573-021-00252-y.]

In recent years, hematopoietic progenitor kinase 1 (HPK1) and FMS-like tyrosine kinase 3 (FLT3) mutation inhibitors have attracted great interest.

HPK1 belongs to the protein kinase superfamily. STE Ser/Thr protein kinase family. STE20 subfamily. Expressed primarily in hematopoietic organs, including bone marrow, spleen, and thymus. Also expressed at very low levels in lung, kidney, mammary glands, and small intestine. Two alternatively spliced human isoforms have been reported. [https://www.phosphosite.org/proteinAction?id=1180&showAllSites=true. S. Sawasdikosol at al. HPK1 as a novel target for cancer immunotherapy. *Immunol. Res.* 2012, 54(1-3), 262-265; doi: 10.1007/s12026-012-8319-1. J. Liu at al. Critical role of kinase activity of hematopoietic progenitor kinase 1 in anti-tumor immune surveillance. *PLoS ONE* 2019, 14(3), e0212670; https://doi.org/10.1371/journal.pone.0212670. Y. Wang et al. Pharmacological inhibition of hematopoietic progenitor kinase 1 positively regulates T-cell function. PLoS ONE 2020, 15(12), e0243145; https://doi.org/10.1371/journal-.pone.0243145. D. You et al. Enhanced antitumor immunity by a novel small molecule HPK1 inhibitor. *J Immunother. Cancer.* 2021, 9(1); e001402. doi: 10.1136/jitc-2020-001402. D. You et al. Enhanced antitumor immunity by a novel small molecule HPK1 inhibitor. *J. Immunother. Cancer* 2021, 9, e001402. doi:10.1136/jitc-2020-001402].

In 2021, the first clinical trial of an inhibitor (phase 1.2) was started in patients with Pembrolizumab in Subjects with Advanced Solid Malignancies. [A First-In-Human, Phase 1/2 Study Of CFI-402411, a Hematopoietic Progenitor Kinase-1 (HPK1) Inhibitor, as a Single Agent and in Combination with Pembrolizumab in Subjects with Advanced Solid Malignancies. Study HIC #:2000029001. Start Date Apr. 13, 2021. End Date Dec. 1, 2021. Last Updated: Jul. 15, 2021. https://www.yalemedicine.org/clinical-trials/8756].

AML is a cancer of the myeloid line of blood cells, characterized by the rapid growth of abnormal cells that build up in the bone marrow and blood and interfere with normal blood cell production. As an acute leukemia, AML progresses rapidly, and is typically fatal within weeks or months if left untreated. [https://www.cancer.gov/types/leukemia/patient/adult-aml-treatment-pdq #section/all. Updated: Mar. 6, 2020].

AML is a highly heterogenous disease with multiple signaling pathways contributing to its pathogenesis. A key driver of AML is FLT3. Activating mutations in FLT3, primarily the FLT3-internal tandem duplication (FLT3-ITD), are associated with decreased progression-free and overall survival. Identification of the importance of FLT3-ITD and the FLT3 pathway in the prognosis of patients with AML has stimulated efforts to develop therapeutic inhibitors of FLT3. Although these inhibitors have shown promising antileukemic activity, they have had limited efficacy to date as single agents and may require use in combination with cytotoxic chemotherapies. [R. Swords, C. Freeman, F. Giles. Targeting the FMS-like tyrosine kinase 3 in acute myeloid leukemia. *Leukemia* 2012, 26 (10), 2176-2185; doi: 10.1038/leu.2012.114. Epub 2012 Apr. 27.]

In 2015, AML affected about one million people, and resulted in 147,000 deaths globally. It most commonly occurs in older adults. Males are affected more often than females. The five-year survival rate is about 35% in people under 60 years old and 10% in people over 60 years old. Older people whose health is too poor for intensive chemotherapy have a typical survival of five to ten months. It accounts for roughly 1.1% of all cancer cases, and 1.9% of cancer deaths in the United States. See, https://en.wikipedia.org/wiki/Acute_myeloid_leukemia.

In recent years, drugs that target specific parts of cancer cells have been developed. Targeted drugs work differently from standard chemotherapy drugs and tend to have different side effects.

In some patients with AML, the leukemia cells have a mutation in the FLT3 gene. This gene helps the cells make a protein (also called FLT3) that helps the cells grow. Drugs that target the FLT3 protein can help treat some of these leukemias. The most advanced example of such drugs appears to be Gilteritinib. [M. Levis, A. E. Perl. Gilteritinib: potent targeting of FLT3 mutations in AML. *Blood advances* 2020, 4 (6), 1178-1191]. Gilteritinib is a clinically active FLT3 inhibitor with broad activity against FLT3 kinase domain mutations [T. C. Tarver et al. *Blood advances* 2020, 4 (3), 514-524; L. Y. Lee et al. Preclinical studies of gilteritinib, a next-generation FLT3 inhibitor. *Blood* 2017, 129 (2), 257-260].

In November 2018, the FDA approved gilteritinib for treatment of adult patients with relapsed or refractory acute myeloid leukemia (AML) with a FLT3 mutation as detected by an FDA-approved test [https://en.wikipedia.org/wiki/Gilteritinib. S. Dhillon. Gilteritinib: First Global Approval. *Drugs* 2019; https://doi.org/10.1007/s40265-019-1062-3].

Gilteritinib (Xospata) works by blocking FLT3 and other proteins on cancer cells that can help the cells grow. This drug can treat adults whose leukemia cells have a mutation in the FLT3 gene and whose AML has not gotten better on previous treatments or has recurred. The structure of Gilteritinib presented below.

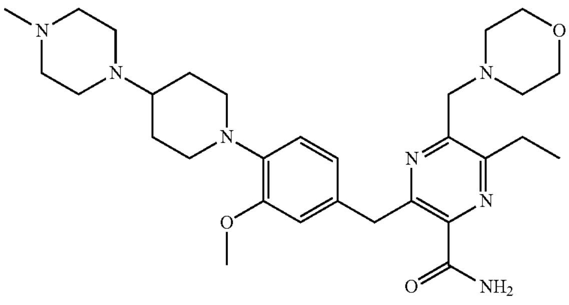 [SMILES: CCc1nc(C(N)=O)c(Cc2ccc(N3CCC(N4CCN(C)CC4)CC3)c(OC)c2)nc1CN1CCOCC1]

There is a need for therapeutic agents that treat adult patients with relapsed or refractory acute myeloid leukemia (AML) with a FLT3 mutation. This invention is intended to fill these unmet needs associated with current FLT3 inhibition therapy.

SUMMARY OF THE INVENTION

A first aspect of the invention relates to compounds of Formula I and pharmaceutically acceptable salts, solvates, prodrugs, enantiomers, stereoisomers, or tautomers thereof:

(I)

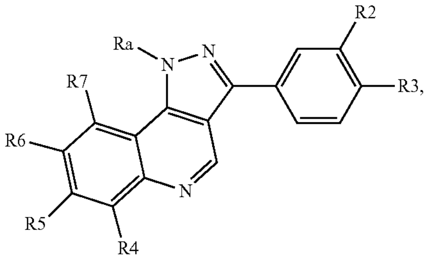

wherein:

$R_a$ is selected from

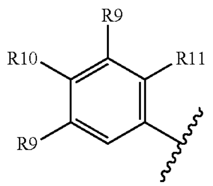

and

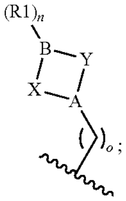

each $R_1$ is independently selected from the group consisting of $C_{1-6}$alkyl, $—NH_2$, $—NH(C_{1-6}$ alkyl), and $—N(C_{1-6}alkyl)_2$;

$R_2$ is selected from H, halogen, $C_{1-6}$alkyl, $—OC_{1-6}$alkyl, $(C_{1-4}alkyl)_2N(CH_2)_mN(C_{1-4}alkyl)$-, $(C_{1-4}alkyl)_2N(CH_2)_mO—$, heterocyclyl, heterocyclyl$(CH_2)_mO—$, heteroaryl, $—W—X—R_1$, or group

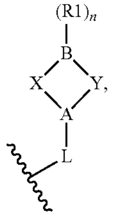

wherein $R_2$ is optionally substituted with 1-6 groups $R_8$;

$R_3$ is selected from H, halogen, $C_{1-6}$alkyl, $—OC_{1-6}$alkyl, $(C_{1-4}alkyl)_2N(CH_2)_mN(C_{1-4}alkyl)$-, $(C_{1-4}alkyl)_2N(CH_2)_mO—$, heterocyclyl, heterocyclyl$(CH_2)_mO—$, heteroaryl, $—W—X—R_1$, or group

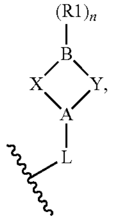

wherein $R_3$ is optionally substituted with 1-6 groups $R_8$;

or $R_2$ and $R_3$ together with the atoms to which they are bound and any intervening atoms, form the group —K—X-M-;

each from $R_4$, $R_5$, $R_6$ or $R_7$ is independently selected from the group consisting of H, halogen, —CN, $—C_{1-4}$alkyl, —OH, $—OR_8$, $—OCF_3$, $—COOR_8$, $—CONH_2$, $—CONHR_8$, $—CON(R_8)_2$, $—SO_2OH$, $—SO_2NHR_8$, and $—SO_2N(R_8)_2$;

$R_8$ is selected from $C_{1-6}$alkyl, $C_{2-6}$alkenyl, $C_{2-6}$alkynyl, and $C_{3-8}$cycloalkyl;

each $R_9$ is independently selected from the group consisting of H, halogen, $C_{1-6}$alkyl, —OH, $—OC_{1-6}$alkyl, and

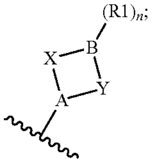

$R_{10}$ is selected from H, halogen, $C_{1-6}$alkyl, —OH, and $—OC_{1-6}$alkyl;

or any one of $R_9$ and $R_{10}$ together with the atoms to which they are bound and any intervening atoms, form the group $—X—N(R_{12})—Y—$;

$R_{11}$ is selected from H, halogen, $C_{1-6}$alkyl, —OH, and $—OC_{1-6}$alkyl;

$R_{12}$ is H or $C_{1-6}$alkyl;

X is independently, at each occurrence selected from $—CH_2—$, $—(CH_2)_2—$, and $—(CH_2)_3—$;

Y is independently, at each occurrence selected from $—CH_2—$, $—(CH_2)_2—$, and $—(CH_2)_3—$;

A is independently, at each occurrence selected from CH and N;

B is independently, at each occurrence selected from CH, $CH_2$, N, NH and O;

L is independently, at each occurrence selected from a single bond, —$(CH_2)_m$—, —$O(CH_2)_m$—, and —$NH(CH_2)_m$—;

W is O, S, NH, or $N(C_{1-6}alkyl)$;

K and M are independently selected from O, S, SO, $SO_2$, CO, NH, and $NR_8$;

m is independently, at each occurrence, an integer selected from 1, 2, 3, 4, 5, and 6;

n is independently, at each occurrence, selected from 0 and 1;

is independently, at each occurrence, selected from 1, 2, and 3;

wherein:

aryl is cyclic, aromatic hydrocarbon groups that have 1 to 3 aromatic rings fused or connected each other via single bond;

heteroaryl is a monovalent monocyclic or polycyclic aromatic radical of 5 to 24 ring atoms, containing one or more ring heteroatoms selected from N, O, S, P, Se, or B, the remaining ring atoms being C;

heterocyclyl is a saturated or partially unsaturated 3-10 membered monocyclic, 7-12 membered bicyclic (fused, bridged, or spiro rings), or 11-14 membered tricyclic ring system (fused, bridged, or spiro rings) having one or more heteroatoms independently selected from O, N, S, P, Se, or B;

provided that the compound contains at least one of the group selected from: $R_2$ or $R_3$ is $(C_{1-4}alkyl)_2N(CH_2)_mN(C_{1-4}alkyl)$-, $(C_{1-4}alkyl)_2N(CH_2)_mO$—, heterocyclyl, heterocyclyl$(CH_2)_mO$—, heteroaryl, —W—X—$R_1$, or

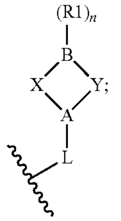

or $R_2$ and $R_3$ together with the atoms to which they are bound and any intervening atoms, form the group —K—X-M-; or $R_a$ is

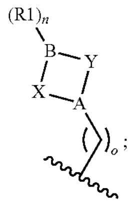

or any one of $R_9$ and $R_{10}$ together with the atoms to which they are bound and any intervening atoms, form the group —X—$N(R_{12})$—Y—; or any one of $R_9$ is

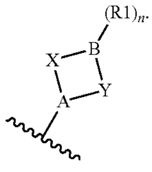

In more specific aspect the invention relates to compounds of Formula I (A, B, C, D and D', E and E', F and G) and pharmaceutically acceptable salts, solvates, prodrugs, enantiomers, stereoisomers, or tautomers thereof:

(I-A)

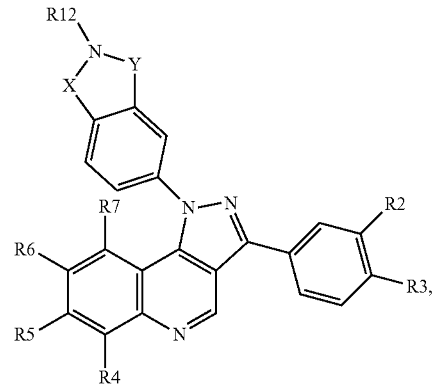

wherein:

X is selected from —$CH_2$—, —$(CH_2)_2$—, and —$(CH_2)_3$—;

Y is selected from —$CH_2$—, —$(CH_2)_2$—, and —$(CH_2)_3$—;

each $R_1$ is independently selected from the group consisting of —$C_{1-6}alkyl$, —$NH_2$, —$NH(C_{1-6}alkyl)$, and —$N(C_{1-6}alkyl)_2$;

$R_2$ is selected from H, halogen, —$C_{1-6}alkyl$, —$OC_{1-6}alkyl$, $(C_{1-4}alkyl)_2N(CH_2)_mN(C_{1-4}alkyl)$-, $(C_{1-4}alkyl)_2N(CH_2)_mO$—, heterocyclyl, heterocyclyl $(CH_2)_mO$—, heteroaryl, —W—X—$R_1$, and

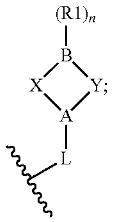

$R_3$ is selected from H, halogen, —$C_{1-6}alkyl$, —$OC_{1-6}alkyl$, $(C_{1-4}alkyl)_2N(CH_2)_mN(C_{1-4}alkyl)$-, $(C_{1-4}alkyl)_2N(CH_2)_mO$—, heterocyclyl, heterocyclyl $(CH_2)_mO$—, heteroaryl, —W—X—$R_1$, and

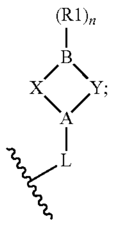

wherein each from $R_2$ and $R_3$ is optionally substituted with 1-6 groups $R_8$;

or $R_2$ and $R_3$ together with the atoms to which they are bound and any intervening atoms, form the group —K—X-M-;

each from $R_4$, $R_5$, $R_6$ and $R_7$ is independently selected from the group consisting of H, halogen, —CN, —$C_1$-

$_4$alkyl, —$OR_8$, —$OCF_3$, —$COOR_8$, —$CONH_2$, —$CONHR_8$, —$CON(R_8)_2$, —$SO_2OH$, —$SO_2NHR_8$, and —$SO_2N(R_8)_2$;

$R_8$ is selected from $C_{1-6}$ alkyl, $C_{2-6}$ alkenyl, $C_{2-6}$ alkynyl, and $C_{3-8}$ cycloalkyl;

$R_{12}$ is H or $C_{1-6}$alkyl;

K and M is independently selected from O, S, SO, $SO_2$, CO, NH, and $NR_8$;

A is CH or N;

B is selected from CH, $CH_2$, N, NH and O;

L is a single bond or —$OCH_2CH_2$—;

W is selected from O, S, NH, and N($C_{1-6}$alkyl);

m is an integer selected from 1, 2, 3, 4, 5, and 6;

n is 0 or 1;

(I-B)

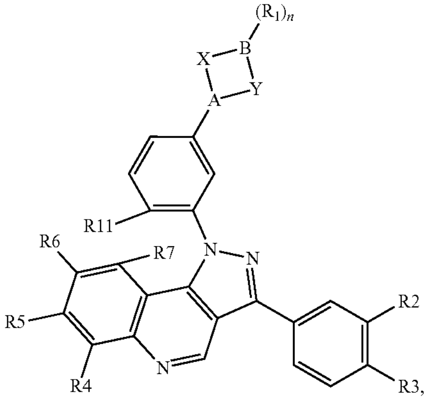

wherein:

A is CH or N;

B is CH, $CH_2$, N, NH or O;

X is selected from —$CH_2$—, —$(CH_2)_2$—, and —$(CH_2)_3$—;

Y is selected from —$CH_2$—, —$(CH_2)_2$—, and —$(CH_2)_3$—;

each $R_1$ is independently selected from —$C_{1-6}$alkyl, —$NH_2$, —NH($C_{1-6}$alkyl), and —N($C_{1-6}$alkyl)$_2$;

$R_2$ is selected from H, halogen, —$C_{1-6}$alkyl, —$OC_{1-6}$alkyl, ($C_{1-4}$alkyl)$_2$N$(CH_2)_m$N($C_{1-4}$alkyl)-, ($C_{1-4}$alkyl)$_2$N$(CH_2)_m$O—, heterocyclyl, heterocyclyl $(CH_2)_m$O—, heteroaryl, —W—X—$R_1$, and

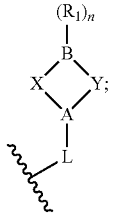

$R_3$ is selected from H, halogen, —$C_{1-6}$alkyl, —$OC_{1-6}$alkyl, ($C_{1-4}$alkyl)$_2$N$(CH_2)_m$N($C_{1-4}$alkyl)-, ($C_{1-4}$alkyl)$_2$N$(CH_2)_m$O—, heterocyclyl, heterocyclyl $(CH_2)_m$O—, heteroaryl, —W—X—$R_1$, and

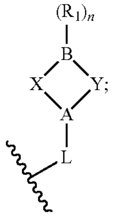

wherein each from $R_2$ and $R_3$ is optionally substituted with 1-6 groups $R_8$;

or $R_2$ and $R_3$ together with the atoms to which they are bound and any intervening atoms, form the group —K—X-M-;

each from $R_4$, $R_5$, $R_6$, and $R_7$ is independently selected from the group consisting of H, halogen, —CN, —$C_{1-4}$alkyl, —$OR_8$, —$OCF_3$, —$COOR_8$, —$CONH_2$, —$CONHR_8$, —$CON(R_8)_2$, —$SO_2OH$, —$SO_2NHR_8$, and —$SO_2N(R_8)_2$;

$R_8$ is selected from $C_{1-6}$ alkyl, $C_{2-6}$ alkenyl, $C_{2-6}$ alkynyl, and $C_{3-8}$ cycloalkyl;

$R_{11}$ is selected from H, halogen, —OH, —$C_{1-6}$alkyl, and —$OC_{1-6}$alkyl;

each from K and M is independently selected from O, S, SO, $SO_2$, CO, NH, and $NR_8$;

W is selected from O, S, NH, and N($C_{1-6}$alkyl);

L is a single bond or —$OCH_2CH_2$—;

m is an integer selected from 1, 2, 3, 4, 5, and 6;

and n is selected from 0 and 1;

(I-C)

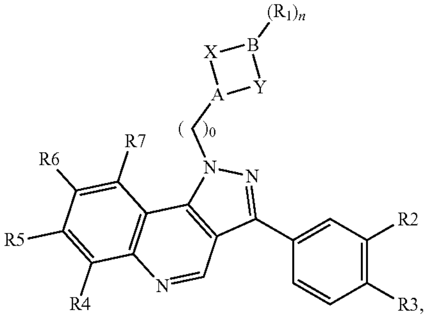

wherein:

A is CH or N;

B is CH, $CH_2$, N, NH, or O;

X is selected from —$CH_2$—, —$(CH_2)_2$—, and —$(CH_2)_3$—;

Y is selected from —$CH_2$—, —$(CH_2)_2$—, and —$(CH_2)_3$—;

each $R_1$ is independently selected from $C_{1-6}$alkyl, —$NH_2$, —NH($C_{1-6}$alkyl), and —N($C_{1-6}$ alkyl)$_2$;

$R_2$ is selected from H, halogen, —$C_{1-6}$alkyl, —$OC_{1-6}$alkyl, ($C_{1-4}$alkyl)$_2$N$(CH_2)_m$N($C_{1-4}$alkyl)-, ($C_{1-4}$alkyl)$_2$N$(CH_2)_m$O—, heterocyclyl, heterocyclyl $(CH_2)_m$O—, heteroaryl, —W—X—$R_1$, and

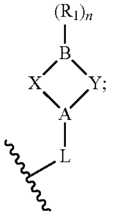

$R_3$ is selected from H, halogen, $C_{1-6}$alkyl, —$OC_{1-6}$alkyl, $(C_{1-4}alkyl)_2N(CH_2)_mN(C_{1-4}alkyl)$-, $(C_{1-4}alkyl)_2N(CH_2)_mO$—, heterocyclyl, heterocyclyl$(CH_2)_mO$—, heteroaryl, —W—X—$R_1$, and

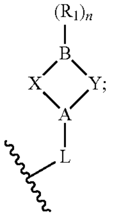

wherein each from $R_2$ and $R_3$ is optionally substituted with 1-6 groups $R_8$;

or $R_2$ and $R_3$ together with the atoms to which they are bound and any intervening atoms, form the group —K—X-M-;

each from $R_4$, $R_5$, $R_6$, and $R_7$ is independently selected from the group H, halogen, —CN, $C_{1-4}$alkyl, —$OR_8$, —$OCF_3$, —$COOR_8$, —$CONH_2$, —$CONHR_8$, —$CON(R_8)_2$, —$SO_2OH$, $SO_2NHR_8$, and $SO_2N(R_8)_2$;

$R_8$ is selected from $C_{1-6}$ alkyl, $C_{2-6}$ alkenyl, $C_{2-6}$ alkynyl, and $C_{3-8}$ cycloalkyl;

each from K and M is independently selected from O, S, SO, $SO_2$, CO, NH, and $NR_8$;

W is selected from O, S, NH, and $N(C_{1-6}alkyl)$;

L is a single bond or —$OCH_2CH_2$—;

m is an integer selected from 1, 2, 3, 4, 5, and 6;

n is selected from 0 and 1;

and o is selected from 1, 2, and 3;

(I-D)

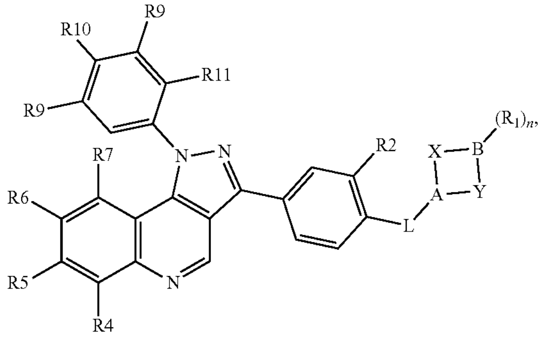

-continued (I-D')

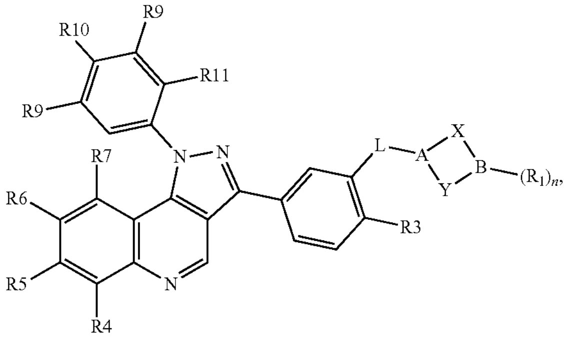

wherein:

A is CH or N;

B is CH, $CH_2$, N, NH, or O;

L is a single bond or —$OCH_2CH_2$—;

X is selected from —$CH_2$—, —$(CH_2)_2$—, and —$(CH_2)_3$—;

Y is selected from —$CH_2$—, —$(CH_2)_2$—, and —$(CH_2)_3$—;

each $R_1$ is independently selected from —$C_{1-6}$alkyl, —$NH_2$, —$NH(C_{1-6}alkyl)$, or —$N(C_{1-6}alkyl)_2$;

each from $R_2$ and $R_3$ is independently selected from the group consisting of H, halogen, —$C_{1-6}$alkyl, —$OC_{1-6}$alkyl, $(C_{1-4}alkyl)_2N(CH_2)_mN(C_{1-4}alkyl)$-, $(C_{1-4}alkyl)_2N(CH_2)_mO$—, heterocyclyl, heterocyclyl $(CH_2)_mO$—, heteroaryl, —W—X—$R_1$, and

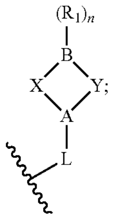

wherein each from $R_2$ and $R_3$, is optionally substituted with 1-6 groups $R_8$;

each from $R_4$, $R_5$, $R_6$ and $R_7$ is independently selected from the group consisting of H, halogen, —CN, —$C_{1-4}$alkyl, —$OR_8$, —$OCF_3$, —$COOR_8$, —$CONH_2$, —$CONHR_8$, —$CON(R_8)_2$, —$SO_2OH$, —$SO_2NHR_8$, and —$SO_2N(R_8)_2$;

$R_8$ is selected from $C_{1-6}$ alkyl, $C_{2-6}$ alkenyl, $C_{2-6}$ alkynyl, and $C_{3-8}$ cycloalkyl;

each $R_9$ is independently selected from the group consisting of H, halogen, $C_{1-6}$alkyl, —OH, —$OC_{1-6}$alkyl, and

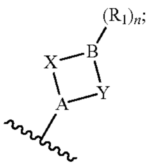

$R_{10}$ is selected from H, halogen, OH, $C_{1-6}$alkyl, and —$OC_{1-6}$alkyl;

or any one of $R_9$ and $R_{10}$ together with the atoms to which they are bound and any intervening atoms, form the group —X—$N(R_{12})$—Y—;

$R_{11}$ is selected from H, halogen, OH, $C_{1-6}$alkyl, and —$OC_{1-6}$alkyl;

$R_{12}$ is H or $C_{1-6}$alkyl;

W is selected from O, S, NH, and N($C_{1-6}$alkyl);

m is an integer selected from 1, 2, 3, 4, 5, and 6;

n is 0 or 1;

(I-E)

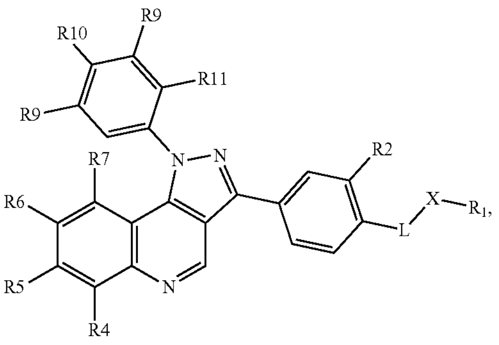

(I-E')

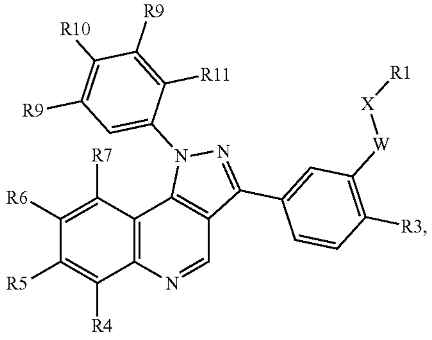

wherein:

$R_1$ is selected from —$C_{1-6}$alkyl, —$NH_2$, —NH($C_{1-6}$alkyl), or —N($C_{1-6}$alkyl)$_2$;

each from $R_2$ and $R_3$ is independently selected from the group consisting of H, halogen, —$C_{1-6}$alkyl, —$OC_{1-6}$alkyl, ($C_{1-4}$alkyl)$_2$N($CH_2$)$_m$N($C_{1-4}$alkyl)-, ($C_{1-4}$alkyl)$_2$N($CH_2$)$_m$O—, heterocyclyl, heterocyclyl ($CH_2$)$_m$O—, heteroaryl, —W—X—$R_1$, and

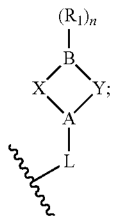

wherein each from $R_2$ and $R_3$, is optionally substituted with 1-6 groups $R_8$;

X is selected from —$CH_2$—, —($CH_2$)$_2$—, and —($CH_2$)$_3$—;

Y is selected from —$CH_2$—, —($CH_2$)$_2$—, and —($CH_2$)$_3$—;

W is selected from O, S, NH, and N($C_{1-6}$alkyl);

each from $R_4$, $R_5$, $R_6$ and $R_7$ is independently selected from the group consisting of H, halogen, —CN, $C_{1-4}$alkyl, —OH, —$OR_8$, —$OCF_3$, —$COOR_8$, —$CONH_2$, —$CONHR_8$, —CON($R_8$)$_2$, —$SO_2OH$, —$SO_2NHR_8$, and —$SO_2N(R_8)_2$;

$R_8$ is selected from $C_{1-6}$ alkyl, $C_{2-6}$ alkenyl, $C_{2-6}$ alkynyl, and $C_{3-8}$ cycloalkyl;

each $R_9$ is independently selected from the group consisting of H, halogen, —$C_{1-6}$alkyl, —OH, —$OC_{1-6}$alkyl, and

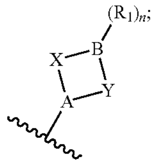

$R_{10}$ is selected from H, halogen, —OH, $C_{1-6}$alkyl, and —$OC_{1-6}$alkyl;

or any one of $R_9$ and $R_{10}$ together with the atoms to which they are bound and any intervening atoms, from the group —X—N($R_{12}$)—Y—;

$R_{11}$ is selected from H, halogen, OH, $C_{1-6}$alkyl, and —$OC_{1-6}$alkyl;

$R_{12}$ is H or $C_{1-6}$alkyl;

L is a single bond or —$OCH_2CH_2$—;

m is an integer selected from 1, 2, 3, 4, 5, and 6;

n is 0 or 1;

(I-F)

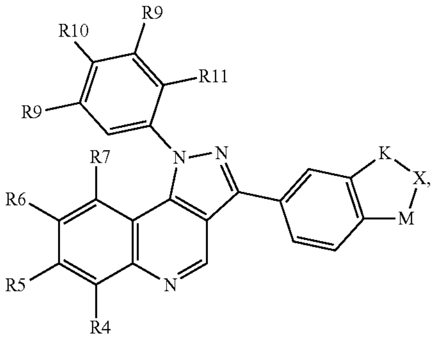

wherein:

each from K and M is independently selected from O, S, SO, $SO_2$, CO, NH, or $NR_8$;

X is selected from —$CH_2$—, —($CH_2$)$_2$—, and —($CH_2$)$_3$—;

Y is selected from —$CH_2$—, —($CH_2$)$_2$—, and —($CH_2$)$_3$—;

each from $R_4$, $R_5$, $R_6$ and $R_7$ is independently selected from the group consisting of H, halogen, —CN, —$C_{1-4}$alkyl, —$OR_8$, —$OCF_3$, —$COOR_8$, —$CONH_2$, —$CONHR_8$, —CON($R_8$)$_2$, —$SO_2OH$, —$SO_2NHR_8$, and —$SO_2N(R_8)_2$;

$R_8$ is selected from $C_{1-6}$ alkyl, $C_{2-6}$ alkenyl, $C_{2-6}$ alkynyl, and $C_{3-8}$ cycloalkyl;

each $R_9$ is independently selected from the group consisting of H, halogen, —$C_{1-6}$alkyl, —OH, —$OC_{1-6}$alkyl, and

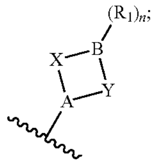

$R_{10}$ is selected from H, halogen, OH, —$C_{1-6}$alkyl, and —$OC_{1-6}$alkyl;

or any one of $R_9$ and $R_{10}$ together with the atoms to which they are bound and any intervening atoms, form the group —X—N($R_{12}$)—Y—;

$R_1$ is selected from H, halogen, OH, $C_{1-6}$alkyl, and —$OC_{1-6}$alkyl;

$R_{12}$ is H or $C_{1-6}$alkyl;

A is CH or N;

B is CH, $CH_2$, N, NH, or O;

m is an integer selected from 1, 2, 3, 4, 5, and 6;

n is 0 or 1;

(I-G)

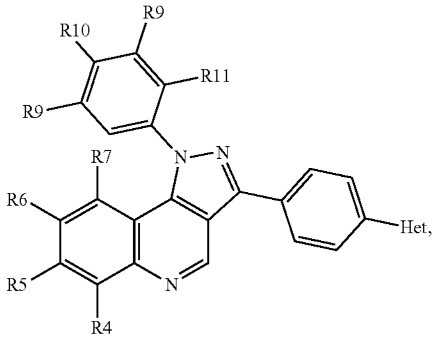

wherein:

Het is Heterocyclyl or Heteroaryl;

wherein Het is optionally substituted with 1-6 groups $R_8$;

each from $R_4$, $R_5$, $R_6$ and $R_7$ is independently selected from H, halogen, —CN, —$C_{1-4}$alkyl, —$OR_8$, —$OCF_3$, —$COOR_8$, —$CONH_2$, —$CONHR_8$, —$CON(R_8)_2$, —$SO_2OH$, —$SO_2NHR_8$, and —$SO_2N(R_8)_2$;

$R_8$ is selected from $C_{1-6}$ alkyl, $C_{2-6}$ alkenyl, $C_{2-6}$ alkynyl, and $C_{3-8}$ cycloalkyl;

each $R_9$ is independently selected from the group consisting of H, halogen, —$C_{1-6}$alkyl, —OH, —$OC_{1-6}$alkyl, and

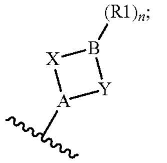

$R_{10}$ is selected from H, halogen, OH, —$C_{1-6}$alkyl, or —$OC_{1-6}$alkyl;

or any one of $R_9$ and $R_{10}$ together with the atoms to which they are bound and any intervening atoms, form the group —X—N($R_{12}$)—Y—;

$R_{11}$ is selected from H, halogen, OH, $C_{1-6}$alkyl, and —$OC_{1-6}$alkyl $R_{12}$ is H or $C_{1-6}$alkyl;

A is CH or N;

B is CH, $CH_2$, N, NH, or O;

X is —$CH_2$—, —$(CH_2)_2$—, or —$(CH_2)_3$—;

Y is —$CH_2$—, —$(CH_2)_2$—, or —$(CH_2)_3$—;

n is 0 or 1.

Another aspect of the invention is directed to pharmaceutical compositions comprising a compound of Formula I (A-G), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the invention relates to a method of treating a disease or disorder associated with modulation of hematopoietic progenitor kinase 1 (HPK1). The method comprises administering to a patient in need of a treatment for diseases or disorders associated with modulation of HPK1 an effective amount of a compound of Formula I (A-G), or a pharmaceutically acceptable salt, hydrate, solvate, prodrug, stereoisomer, tautomer, or pharmaceutical composition thereof.

Another aspect of the invention is directed to a method of inhibiting hematopoietic progenitor kinase 1 (HPK1). The method involves administering to a patient in need thereof an effective amount of a compound of Formula I (A-G), or a pharmaceutically acceptable salt, hydrate, solvate, prodrug, stereoisomer, tautomer, or pharmaceutical composition thereof.

Another aspect of the present invention relates to compounds of Formula I (A-G), or pharmaceutically acceptable salts, hydrates, solvates, prodrugs, stereoisomers, tautomers, or pharmaceutical compositions thereof, for use in the manufacture of a medicament for inhibiting hematopoietic progenitor kinase 1 (HPK1).

Another aspect of the present invention relates to the use of compounds of Formula I (A-G), or pharmaceutically acceptable salts, hydrates, solvates, prodrugs, stereoisomers, tautomers, or pharmaceutical compositions thereof, in the treatment of a disease associated with inhibiting hematopoietic progenitor kinase 1 (HPK1).

Another aspect of the invention relates to a method of treating a disease or disorder associated with modulation of FMS-like tyrosine kinase 3 (FLT3) gene. The method comprises administering to a patient in need of a treatment for diseases or disorders associated with modulation of FLT3 an effective amount of a compound of Formula I (A-G), or a pharmaceutically acceptable salt, hydrate, solvate, prodrug, stereoisomer, tautomer, or pharmaceutical composition thereof.

Another aspect of the invention is directed to a method of inhibiting tyrosine kinase 3 (FLT3). The method involves administering to a patient in need thereof an effective amount of a compound of Formula (I), or a pharmaceutically acceptable salt, hydrate, solvate, prodrug, stereoisomer, tautomer, or pharmaceutical composition thereof.

Another aspect of the present invention relates to compounds of Formula (I), or pharmaceutically acceptable salts, hydrates, solvates, prodrugs, stereoisomers, tautomers, or pharmaceutical compositions thereof, for use in the manufacture of a medicament for inhibiting tyrosine kinase 3 (FLT3).

Another aspect of the present invention relates to the use of compounds of Formula (I), or pharmaceutically acceptable salts, hydrates, solvates, prodrugs, stereoisomers, tautomers, or pharmaceutical compositions thereof, in the treatment of a disease associated with inhibiting tyrosine kinase 3 (FLT3).

Another aspect of the present invention relates to compounds of Formula (I), or pharmaceutically acceptable salts, hydrates, solvates, prodrugs, stereoisomers, tautomers, or pharmaceutical compositions thereof, for use in the manufacture of a medicament for inhibiting FMS-like tyrosine kinase 3 (FLT3) gene.

Another aspect of the present invention relates to the use of compounds of Formula (I), or pharmaceutically acceptable salts, hydrates, solvates, prodrugs, stereoisomers, tautomers, or pharmaceutical compositions thereof, in the treatment of a disease associated with inhibiting FMS-like tyrosine kinase 3 (FLT3) gene.

Another aspect of the present invention relates to compounds of Formula I (A-G), or pharmaceutically acceptable salts, hydrates, solvates, prodrugs, stereoisomers, tautomers, or pharmaceutical compositions thereof, for use in the manufacture of a medicament for treating or preventing a disease or disorder disclosed herein.

Another aspect of the invention is directed to a method of treating or preventing a disease or disorder disclosed herein in a subject in need thereof. The method involves administering to a patient in need of the treatment an effective amount of a compound of Formula I(A-G), or a pharmaceutically acceptable salt, hydrate, solvate, prodrug, stereoisomer, tautomer, or pharmaceutical composition thereof.

Another aspect of the present invention relates to the use of compounds of Formula I(A-G), or pharmaceutically acceptable salts, hydrates, solvates, prodrugs, stereoisomers, tautomers, or pharmaceutical compositions thereof, in the treatment of a disease or disorder disclosed herein.

The present invention further provides methods of treating a disease or disorder associated with modulation of hematopoietic progenitor kinase 1 (HPK1), comprising administering to a patient suffering from at least one of said diseases or disorders a compound of Formula (I), or a pharmaceutically acceptable salt, hydrate, solvate, prodrug, stereoisomer, tautomer, or pharmaceutical composition thereof.

The present invention provides inhibitors of hematopoietic progenitor kinase 1 (HPK1) that are therapeutic agents in the treatment of diseases and disorders.

The present invention further provides compounds and compositions with an improved efficacy and safety profile relative to known hematopoietic progenitor kinase 1 (HPK1) inhibitors. The present disclosure also provides agents with novel mechanisms of action toward protein tyrosine phosphatase enzymes in the treatment of various types of diseases.

The present invention further provides methods of treating a disease or disorder associated with modulation of FMS-like tyrosine kinase 3 (FLT3) gene, comprising administering to a patient suffering from at least one of said diseases or disorders a compound of Formula (I), or a pharmaceutically acceptable salt, hydrate, solvate, prodrug, stereoisomer, tautomer, or pharmaceutical composition thereof.

The present invention provides inhibitors of FMS-like tyrosine kinase 3 (FLT3) gene that are therapeutic agents in the treatment of diseases and disorders.

The present invention further provides compounds and compositions with an improved efficacy and safety profile relative to known FMS-like tyrosine kinase 3 (FLT3) gene inhibitors. The present disclosure also provides agents with novel mechanisms of action toward FLT3 in the treatment of various types of diseases.

The present invention further provides methods of treating a disease, disorder, or condition selected from cancer, acute myeloid leukemia (AML), cytogenetically normal acute myeloid leukemia (CN-AML) comprising administering to a patient suffering from at least one of said diseases or disorders a compound of Formula (I), or a pharmaceutically acceptable salt, hydrate, solvate, prodrug, stereoisomer, tautomer, or pharmaceutical composition thereof.

Another aspect of the invention relates to a method of synthesis of compounds of Formula (I).

In some aspects, the present disclosure provides a compound obtainable by, or obtained by, a method for preparing compounds described herein.

In some aspects, the present disclosure provides an intermediate as described herein, being suitable for use in a method for preparing a compound as described herein.

In some aspects, the present disclosure provides a method of preparing compounds of the present disclosure.

In some aspects, the present disclosure provides a method of preparing compounds of the present disclosure, comprising one or more steps described herein.

Another aspect of the invention is directed to intermediates used for synthesis of compounds of Formula (I).

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims

DETAILED DESCRIPTION OF THE INVENTION

The present disclosure relates to compounds and compositions that are capable of inhibiting the activity of hematopoietic progenitor kinase 1 (HPK1) and FMS-like tyrosine kinase 3 (FLT3) gene. The disclosure features methods of treating, preventing, or ameliorating a disease or disorder in which FLT3 play a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of diseases, disorders, and conditions, including cancer, acute myeloid leukemia (AML), cytogenetically normal acute myeloid leukemia (CN-AML). In a first aspect of the invention, the compounds of Formula I (A-G) are described:

(I-A)

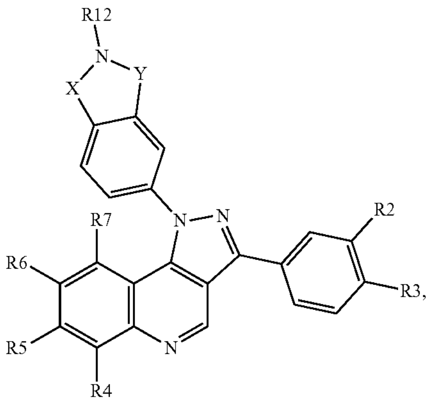
,

-continued (I-B)

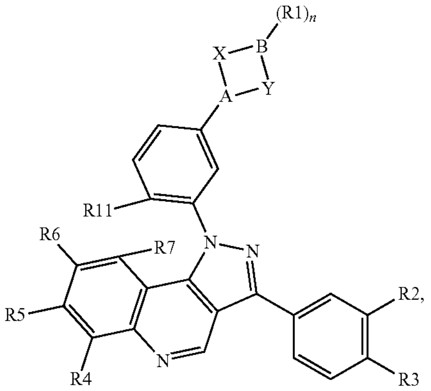

(I-C)

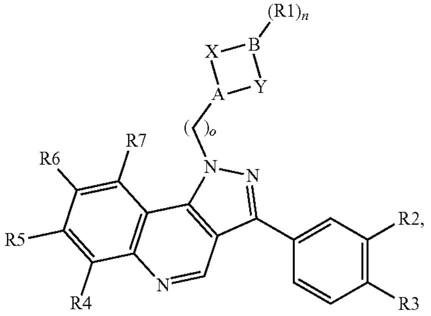

(I-D)

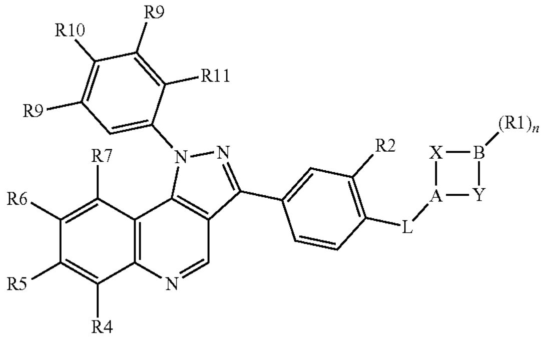

(I-D')

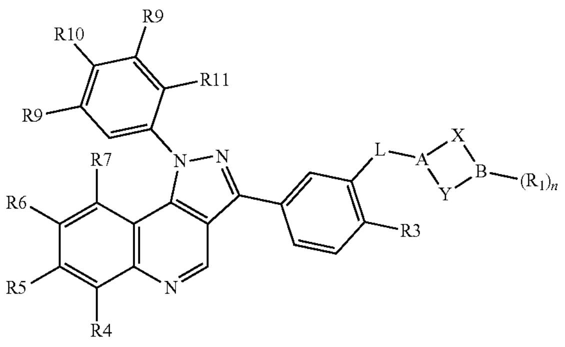

-continued (I-E)

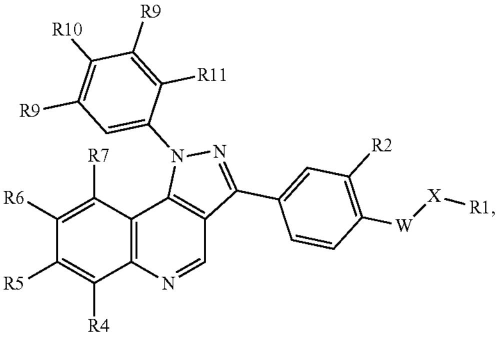

(I-E')

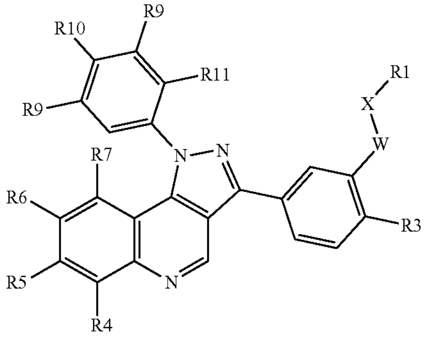

(I-F)

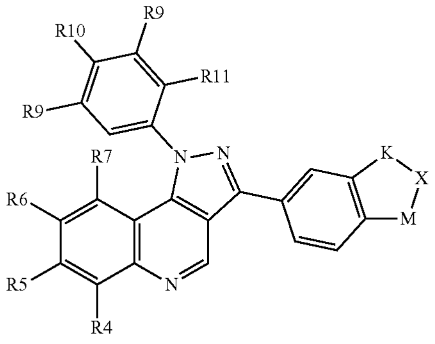

(I-G)

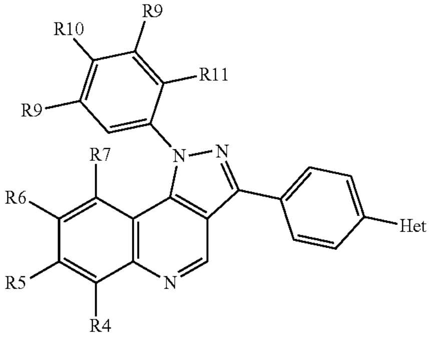

or pharmaceutically acceptable salts, hydrates, solvates, prodrugs, enantiomers, stereoisomers, and tautomers thereof, wherein $R_1$, $R_2$, $R_3$, $R_4$, $R_5$, $R_6$, $R_7$, $R_8$, $R_9$, $R_{10}$, A, B, X, Y, m, n, o, L, W, K, L, Het are described herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —$CH_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$)haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$. The substituents can themselves be optionally substituted. Furthermore, when containing two fused rings, the aryl groups herein defined may have a saturated or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, Se, or B, the remaining ring atoms being C. Heteroaryl as herein defined also means a bicyclic heteroaromatic group wherein the heteroatom is selected from N, O, S, P, Se, or B. Heteroaryl as herein defined also means a tricyclic heteroaromatic group containing one or more ring heteroatoms selected from N, O, S, P, Se, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4] thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated aromatic ring, e.g., a 5-membered heteroaromatic ring containing 1 to 3 heteroatoms selected from N, O, S, P, Se, or B, or a 6-membered heteroaromatic ring containing 1 to 3 nitrogens, wherein the saturated or partially unsaturated ring includes 0 to 4 heteroatoms selected from N, O, S, P, Se, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-TH-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, or benzo[c][1,2]oxaborol-1(3H)-olyl.

"Halogen" or "halo" refers to fluorine, chlorine, bromine, or iodine.

"Alkyl" refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "0" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above-mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, $—CH_2—$, $—CH(CH_3)—$, $—C(CH_3)_2—$, $—CH_2CH_2—$, $—CH_2CH(CH_3)—$, $—CH_2C(CH_3)_2—$, $—CH_2CH_2CH_2—$, $—CH_2CH_2CH_2CH_2—$, and the like.

"Cycloalkyl" means a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, adamantyl, and derivatives thereof. In the case of polycyclic cycloalkyl, only one of the rings in the cycloalkyl needs to be non-aromatic.

"Heterocyclyl", "heterocycle" or "heterocycloalkyl" refers to a saturated or partially unsaturated 3-10 membered monocyclic, 7-12 membered bicyclic (fused, bridged, or spiro rings), or 11-14 membered tricyclic ring system (fused, bridged, or spiro rings) having one or more heteroatoms (such as O, N, S, P, Se, or B), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary ($RNH_2$, R≠H), secondary ($(R)_2NH$, both R≠H) and tertiary ($R_3N$, each R≠H) amines. A substituted amine is intended to mean an amine where at least one of the hydrogen atoms has been replaced by the substituent.

The term "amino" as used herein means a substituent containing at least one nitrogen atom. Specifically, $—NH_2$, —NH(alkyl) or alkylamino, $—N(alkyl)_2$ or dialkylamino, amide-, carbamide-, urea, and sulfamide substituents are included in the term "amino".

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically labelled compounds of Formula I (e.g., those labeled with $^2H$ and $^{14}C$). Deuterated (i.e., $^2H$ or D) and carbon-14 (i.e., $^{14}C$) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease or disorder in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

In some embodiments, $R_1$ is Methyl, Ethyl, $—N(CH_3)_2$, $—N(C_2H_5)_2$.

In some embodiments, $R_2$ is H, halogen, $—C_{1-6}$alkyl, $—OC_{1-6}$alkyl, $(C_{1-4}\ alkyl)_2N(CH_2)_mN(C_{1-4}alkyl)$-, or $(C_{1-4}alkyl)_2N(CH_2)_mO—$.

In some embodiments, $R_2$ is H, Cl, $CH_3—$, $—OCH_3$, $—N(CH_3)CH_2CH_2CH_2N(CH_3)_2$, or $—OCH_2CH_2N(CH_3)_2$.

In some embodiments, $R_3$ is selected from H, halogen, $—C_{1-6}$alkyl, $—OC_{1-6}$alkyl, $(C_{1-4}alkyl)_2N(CH_2)_mN(C_{1-4}alkyl)$-, $(C_{1-4}alkyl)_2N(CH_2)_mO—$, heterocyclyl, heterocyclyl $(CH_2)_mO—$, heteroaryl.

In a further embodiment, $R_3$ is H, $—CH_3$, $—OCH_3$, morpholinyl, $—N(CH_3)CH_2CH_2CH_2N(CH_3)_2$, $—OCH_2CH_2N(CH_3)_2$, or $—O(CH_2)_3$morpholinyl, pyridinyl.

In some embodiments, $R_4$ is selected from H, $—OC_{1-6}$alkyl. In a further embodiment, $R_4$ is H, $—OCH_3$.

In some embodiments, $R_5$ is H.

In some embodiments, $R_6$ is H, $—CH_3$, $—OCH_3$.

In some embodiments, $R_7$ is H, $—CH_3$, or $—OCH_3$. In a further embodiment, $R_7$ is H.

In some embodiments, $R_8$ is $—CH_3$.

In some embodiments, $R_9$ is H, halogen, $C_{1-6}$alkyl, $C_{1-6}$ alkoxy, heterocyclyl.

In some embodiments, $R_9$ is H, Cl, $—CH_3$, 4-Methylpyperazine, 4-N,N-dimethylpiperidine, morpholine.

In some embodiments, $R_{10}$ is H, halogen, $C_{1-6}$ alkyl, or $C_{1-6}$ alkoxy.

In some embodiments, Rn is H, halogen, or $C_1$-$C_6$ alkyl.

In some embodiments, $R_{12}$ is H or $C_{1-6}$alkyl.

In some embodiments, m is 0, 1, 2, 3, 4, 5, or 6. In some embodiments, m is 0, 1, 2, 3, 4, or 5. In some embodiments, m is 0, 1, 2, 3, or 4. In some embodiments, m is 0, 1, 2, or 3. In some embodiments, m is 0, 1, or 2. In some embodiments, m is 0 or 1. In some embodiments, m is 0. In some embodiments, m is 1. In some embodiments, m is 2. In some embodiments, m is 3. In some embodiments, m is 4. In some embodiments, m is 5. In some embodiments, m is 6.

In some embodiments, n is 0, or 1. In some embodiments, n is 0. In some embodiments, n is 1.

In some embodiments, o is 1, 2, or 3. In some embodiments, o is 1, or 2. In some embodiments, o is 1. In some embodiments, o is 2. In some embodiments, o is 3.

Non-limiting illustrative compounds of the present disclosure include:

1-{3-[1-(3,4-dimethylphenyl)-8-methoxy-TH-pyrazolo[4,3-c]quinolin-3-yl]phenyl}-N,N-dimethylpiperidin-4-amine;

4-{3-[1-(3,4-dimethylphenyl)-8-methoxy-TH-pyrazolo[4,3-c]quinolin-3-yl]phenyl}morpholine;

1-{3-[1-(3,4-dimethylphenyl)-8-methoxy-TH-pyrazolo[4,3-c]quinolin-3-yl]phenyl}-4-methylpiperazine;

1-{3-[8-methoxy-3-(3-methoxyphenyl)-1H-pyrazolo[4,3-c]quinolin-1-yl]phenyl}-N,N-dimethylpiperidin-4-amine;

1-{3-[8-methoxy-3-(3-methoxyphenyl)-1H-pyrazolo[4,3-c]quinolin-1-yl]phenyl}-4-methylpiperazine;

1-{3-[8-methoxy-3-(3-methoxyphenyl)-1H-pyrazolo[4,3-c]quinolin-1-yl]-4-methylphenyl}-N,N-dimethylpiperidin-4-amine;

1-{3-[8-methoxy-3-(3-methoxyphenyl)-1H-pyrazolo[4,3-c]quinolin-1-yl]-4-methylphenyl}-4-methylpiperazine;

1-{3-[3-(3,4-dimethylphenyl)-8-methoxy-1H-pyrazolo[4,3-c]quinolin-1-yl]-4-methylphenyl}-N,N-dimethylpiperidin-4-amine;

1-{3-[3-(3,4-dimethylphenyl)-8-methoxy-1H-pyrazolo[4,3-c]quinolin-1-yl]-4-methylphenyl}-4-methylpiperazine;

1-{3-[3-(3,4-dimethylphenyl)-8-methoxy-1H-pyrazolo[4,3-c]quinolin-1-yl]phenyl}-N,N-dimethylpiperidin-4-amine;

1-{3-[1-(2,3-dimethylphenyl)-8-methoxy-1H-pyrazolo[4,3-c]quinolin-3-yl]phenyl}-N,N-dimethylpiperidin-4-amine;

4-{4-[1-(3,4-dimethylphenyl)-8-methoxy-1H-pyrazolo[4,3-c]quinolin-3-yl]phenyl}morpholine;

1-{4-[1-(3,4-dimethylphenyl)-8-methoxy-1H-pyrazolo[4,3-c]quinolin-3-yl]phenyl}-4-methylpiperazine;

1-{4-[1-(3,4-dimethylphenyl)-8-methoxy-1H-pyrazolo[4,3-c]quinolin-3-yl]phenyl}-N,N-dimethylpiperidin-4-amine;

N-[3-(dimethylamino)propyl]-4-[1-(3,4-dimethylphenyl)-8-methoxy-1H-pyrazolo[4,3-c]quinolin-3-yl]-N-methylaniline;

4-{4-[1-(3,4-dimethylphenyl)-8-methoxy-1H-pyrazolo[4,3-c]quinolin-3-yl]phenyl}pyridine;

4-{4-[1-(3,4-dimethylphenyl)-1H-pyrazolo[4,3-c]quinolin-3-yl]phenyl}morpholine;

1-{4-[1-(3,4-dimethylphenyl)-1H-pyrazolo[4,3-c]quinolin-3-yl]phenyl}-4-methylpiperazine;
1-{4-[1-(3,4-dimethylphenyl)-1H-pyrazolo[4,3-c]quinolin-3-yl]phenyl}piperazine;
4-(4-{1-phenyl-1H-pyrazolo[4,3-c]quinolin-3-yl}phenyl)morpholine;
(2-{4-[1-(3,4-dimethylphenyl)-8-methoxy-1H-pyrazolo[4,3-c]quinolin-3-yl]-2-methoxyphenoxy}ethyl)dimethylamine;
4-(2-{4-[1-(3,4-dimethylphenyl)-8-methoxy-1H-pyrazolo[4,3-c]quinolin-3-yl]-2-methoxyphenoxy}ethyl)morpholine;
4-(3-{4-[1-(3,4-dimethylphenyl)-8-methoxy-1H-pyrazolo[4,3-c]quinolin-3-yl]-2-methoxyphenoxy}propyl)morpholine;
3-(2H-1,3-benzodioxol-5-yl)-1-(3,4-dimethylphenyl)-1H-pyrazolo[4,3-c]quinoline;
3-(2H-1,3-benzodioxol-5-yl)-1-phenyl-1H-pyrazolo[4,3-c]quinoline;
3-(2H-1,3-benzodioxol-5-yl)-1-(3,4-dimethylphenyl)-8-methoxy-1H-pyrazolo[4,3-c]quinoline;
3-(2H-1,3-benzodioxol-5-yl)-8-methoxy-1-phenyl-1H-pyrazolo[4,3-c]quinoline;
7-[3-(3,4-dimethoxyphenyl)-1H-pyrazolo[4,3-c]quinolin-1-yl]-1,2,3,4-tetrahydroisoquinoline;
6-[3-(3,4-dimethoxyphenyl)-1H-pyrazolo[4,3-c]quinolin-1-yl]-1,2,3,4-tetrahydroisoquinoline;
5-[3-(3,4-dimethoxyphenyl)-1H-pyrazolo[4,3-c]quinolin-1-yl]-2,3-dihydro-TH-isoindole;
7-[3-(3,4-dimethoxyphenyl)-8-methoxy-1H-pyrazolo[4,3-c]quinolin-1-yl]-1,2,3,4-tetrahydroisoquinoline;
6-[3-(3,4-dimethoxyphenyl)-8-methoxy-1H-pyrazolo[4,3-c]quinolin-1-yl]-1,2,3,4-tetrahydroisoquinoline;
5-[3-(3,4-dimethoxyphenyl)-8-methoxy-1H-pyrazolo[4,3-c]quinolin-1-yl]-2,3-dihydro-1H-isoindole;
7-[3-(3,4-dimethoxyphenyl)-6-methoxy-1H-pyrazolo[4,3-c]quinolin-1-yl]-1,2,3,4-tetrahydroisoquinoline;
6-[3-(3,4-dimethoxyphenyl)-6-methoxy-1H-pyrazolo[4,3-c]quinolin-1-yl]-1,2,3,4-tetrahydroisoquinoline;
5-[3-(3,4-dimethoxyphenyl)-6-methoxy-1H-pyrazolo[4,3-c]quinolin-1-yl]-2,3-dihydro-1H-isoindole;
4-{2-[3-(3,4-dimethoxyphenyl)-8-methoxy-1H-pyrazolo[4,3-c]quinolin-1-yl]ethyl}morpholine;
1-{3-[1-(3,4-dimethylphenyl)-8-methoxy-TH-pyrazolo[4,3-c]quinolin-3-yl]phenyl}piperazine;
N-[3-(dimethylamino)propyl]-3-[1-(3,4-dimethylphenyl)-8-methoxy-1H-pyrazolo[4,3-c]quinolin-3-yl]-N-methylaniline;
4-(2-{5-[1-(3,4-dimethylphenyl)-8-methoxy-1H-pyrazolo[4,3-c]quinolin-3-yl]-2-methoxyphenoxy}ethyl)morpholine;
(2-{5-[1-(3,4-dimethylphenyl)-8-methoxy-1H-pyrazolo[4,3-c]quinolin-3-yl]-2-methoxyphenoxy}ethyl)dimethylamine;
(2-{4-[1-(3,4-dimethylphenyl)-1H-pyrazolo[4,3-c]quinolin-3-yl]-2-methoxyphenoxy}ethyl)dimethylamine;
4-(2-{4-[1-(3,4-dimethylphenyl)-1H-pyrazolo[4,3-c]quinolin-3-yl]-2-methoxyphenoxy}ethyl)morpholine;
4-(2-{5-[1-(3,4-dimethylphenyl)-1H-pyrazolo[4,3-c]quinolin-3-yl]-2-methoxyphenoxy}ethyl)morpholine;
(2-{5-[1-(3,4-dimethylphenyl)-1H-pyrazolo[4,3-c]quinolin-3-yl]-2-methoxyphenoxy}ethyl)dimethylamine;
[2-(2-methoxy-4-{1-phenyl-1H-pyrazolo[4,3-c]quinolin-3-yl}phenoxy)ethyl]dimethylamine;
4-[2-(2-methoxy-4-{1-phenyl-1H-pyrazolo[4,3-c]quinolin-3-yl}phenoxy)ethyl]morpholine;
[2-(2-methoxy-4-{8-methoxy-1-phenyl-TH-pyrazolo[4,3-c]quinolin-3-yl}phenoxy)ethyl]dimethylamine;
4-[2-(2-methoxy-4-{8-methoxy-1-phenyl-1H-pyrazolo[4,3-c]quinolin-3-yl}phenoxy)ethyl]morpholine;
4-[2-(2-methoxy-5-{1-phenyl-1H-pyrazolo[4,3-c]quinolin-3-yl}phenoxy)ethyl]morpholine;
[2-(2-methoxy-5-{1-phenyl-1H-pyrazolo[4,3-c]quinolin-3-yl}phenoxy)ethyl]dimethylamine;
4-[2-(2-methoxy-5-{8-methoxy-1-phenyl-1H-pyrazolo[4,3-c]quinolin-3-yl}phenoxy)ethyl]morpholine;
[2-(2-methoxy-5-{8-methoxy-1-phenyl-1H-pyrazolo[4,3-c]quinolin-3-yl}phenoxy)ethyl]dimethylamine;
4-(2-{4-[1-(3,4-dimethylphenyl)-8-methyl-1H-pyrazolo[4,3-c]quinolin-3-yl]-2-methoxyphenoxy}ethyl)morpholine;
4-(2-{4-[1-(2,4-dimethylphenyl)-8-methyl-1H-pyrazolo[4,3-c]quinolin-3-yl]-2-methoxyphenoxy}ethyl)morpholine;
4-(2-{4-[1-(2,3-dimethylphenyl)-8-methyl-1H-pyrazolo[4,3-c]quinolin-3-yl]-2-methoxyphenoxy}ethyl)morpholine;
4-(2-{4-[1-(2,5-dimethylphenyl)-8-methyl-1H-pyrazolo[4,3-c]quinolin-3-yl]-2-methoxyphenoxy}ethyl)morpholine;
4-(2-{4-[1-(3-chloro-2-methylphenyl)-8-methyl-1H-pyrazolo[4,3-c]quinolin-3-yl]-2-methoxyphenoxy}ethyl)morpholine;
4-(2-{4-[1-(3,4-dimethylphenyl)-8-(trifluoromethoxy)-1H-pyrazolo[4,3-c]quinolin-3-yl]-2-methoxyphenoxy}ethyl)morpholine;
4-(2-chloro-4-{1-phenyl-1H-pyrazolo[4,3-c]quinolin-3-yl}phenyl)morpholine;
1-(2-chloro-4-{1-phenyl-1H-pyrazolo[4,3-c]quinolin-3-yl}phenyl)piperazine;
1-(2-chloro-4-{1-phenyl-1H-pyrazolo[4,3-c]quinolin-3-yl}phenyl)-4-methylpiperazine;
4-(2-chloro-4-{8-methoxy-1-phenyl-1H-pyrazolo[4,3-c]quinolin-3-yl}phenyl)morpholine;
1-(2-chloro-4-{8-methoxy-1-phenyl-TH-pyrazolo[4,3-c]quinolin-3-yl}phenyl)piperazine;
1-(2-chloro-4-{8-methoxy-1-phenyl-TH-pyrazolo[4,3-c]quinolin-3-yl}phenyl)-4-methylpiperazine;
4-{2-chloro-4-[1-(3,4-dimethylphenyl)-1H-pyrazolo[4,3-c]quinolin-3-yl]phenyl}morpholine;
1-{2-chloro-4-[1-(3,4-dimethylphenyl)-1H-pyrazolo[4,3-c]quinolin-3-yl]phenyl}piperazine;
1-{2-chloro-4-[1-(3,4-dimethylphenyl)-1H-pyrazolo[4,3-c]quinolin-3-yl]phenyl}-4-methylpiperazine;
4-{2-chloro-4-[1-(3,4-dimethylphenyl)-8-methoxy-1H-pyrazolo[4,3-c]quinolin-3-yl]phenyl}morpholine;
1-{2-chloro-4-[1-(3,4-dimethylphenyl)-8-methoxy-1H-pyrazolo[4,3-c]quinolin-3-yl]phenyl}piperazine;
1-{2-chloro-4-[1-(3,4-dimethylphenyl)-8-methoxy-1H-pyrazolo[4,3-c]quinolin-3-yl]phenyl}-4-methylpiperazine;
4-(4-{8-methoxy-1-phenyl-1H-pyrazolo[4,3-c]quinolin-3-yl}phenyl)morpholine;
1-(4-{8-methoxy-1-phenyl-1H-pyrazolo[4,3-c]quinolin-3-yl}phenyl)-4-methylpiperazine;
1-(4-{1-phenyl-TH-pyrazolo[4,3-c]quinolin-3-yl}phenyl)piperazine;
1-{3-[3-(3,4-dimethylphenyl)-8-methoxy-TH-pyrazolo[4,3-c]quinolin-1-yl]phenyl}-4-methylpiperazine;
or a pharmaceutically acceptable salt, stereoisomer, solvate, prodrug, or tautomer thereof.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of hematopoietic progenitor kinase 1 (HPK1).

In one embodiment, the compounds of the present invention are inhibitors of hematopoietic progenitor kinase 1 (HPK1).

In some embodiments, the compounds of Formula I are selective inhibitors of hematopoietic progenitor kinase 1 (HPK1).

The present invention relates to compounds which are modulators of hematopoietic progenitor kinase 1 (HPK1).

In one embodiment, the compounds of the present invention are inhibitors of hematopoietic progenitor kinase 1 (HPK1).

In some embodiments, the compounds of Formula I are selective inhibitors of hematopoietic progenitor kinase 1 (HPK1).

The present invention relates to compounds which are modulators of FMS-like tyrosine kinase 3 (FLT3) gene.

In one embodiment, the compounds of the present invention are inhibitors of FMS-like tyrosine kinase 3 (FLT3) gene.

In some embodiments, the compounds of Formula I are selective inhibitors of FMS-like tyrosine kinase 3 (FLT3) gene.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesis of the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Suitable methods include but are not limited to those methods described below. Compounds of the present invention can be synthesized by following the steps outlined in General Procedure A, or in General Procedure B which comprises different sequences of assembling intermediates or compounds. Starting materials are either commercially available or made by known procedures in the reported literature or as illustrated below.

General Procedure A

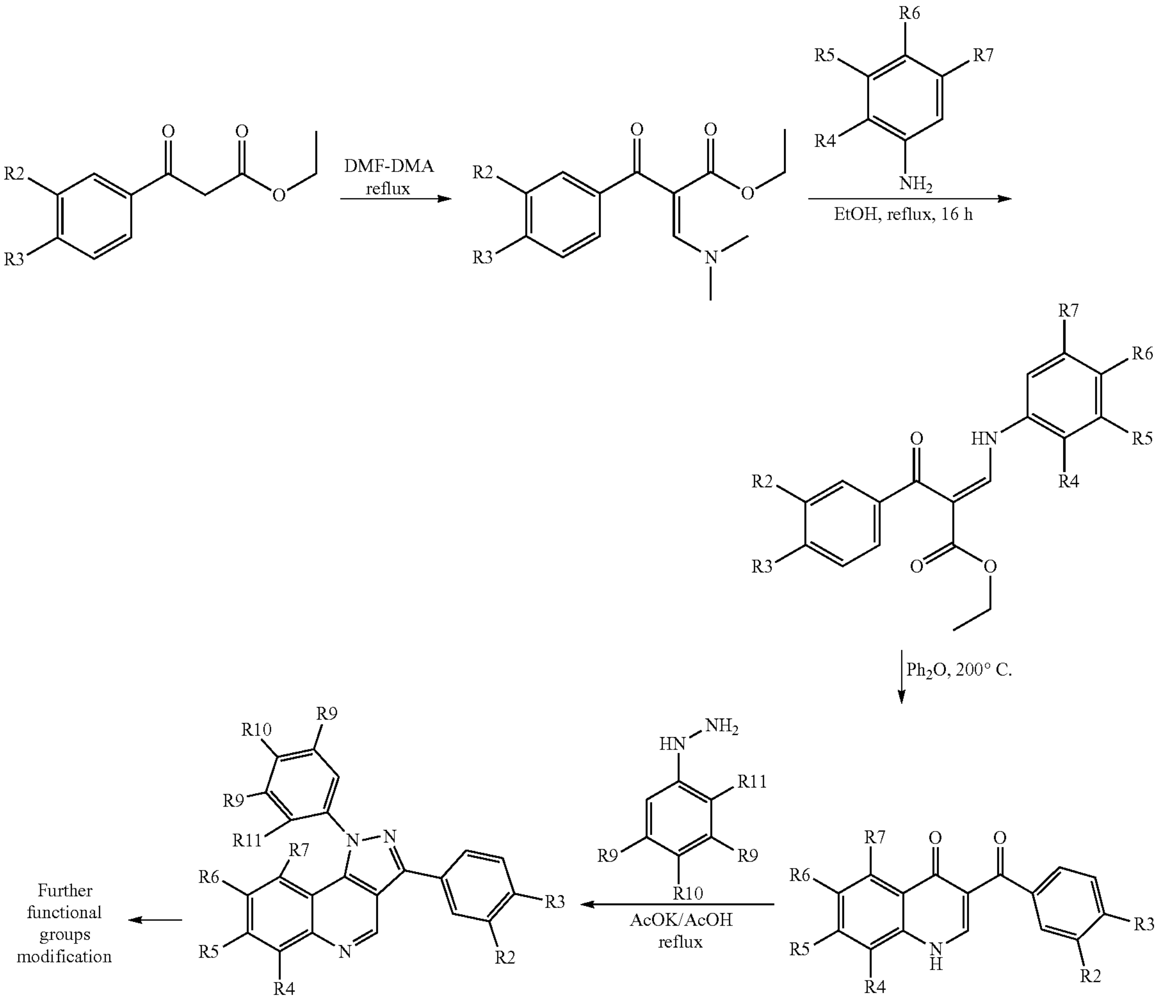

The method of synthesis of the compound of Formula I according to the General Procedure A comprising:

(a) synthesizing substituted ethyl-2-benzoyl-3-(dimethylamino)prop-2-enoate from substituted ethyl 3-oxo-3-phenyl-propanoate, and N,N-Dimethylformamide dimethyl acetal

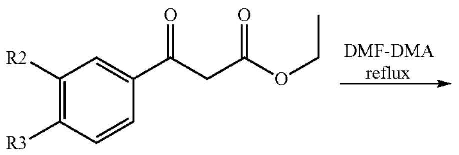

-continued

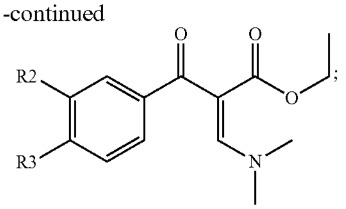

(b) synthesizing of substituted ethyl 3-anilino-2-benzoyl-prop-2-enoate

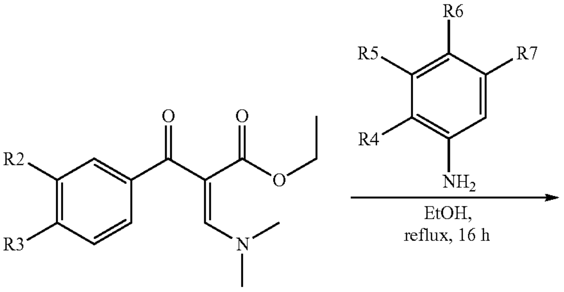

-continued

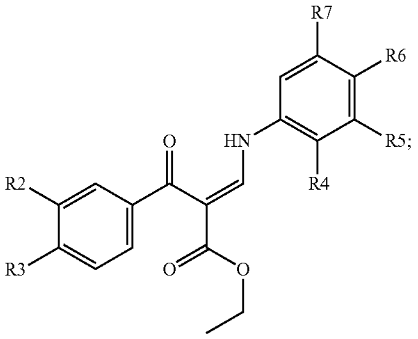

(c) synthesizing of substituted 3-benzoyl-1H-quinolin-4-one

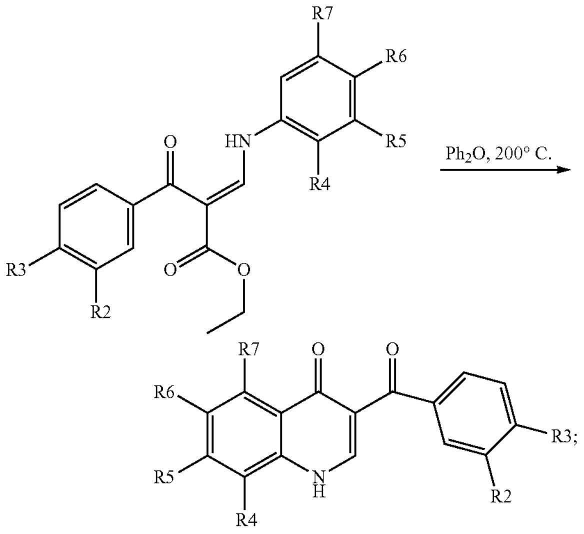

(d) synthesizing of substituted 1,3-diphenylpyrazolo[4,3-c]quinoline

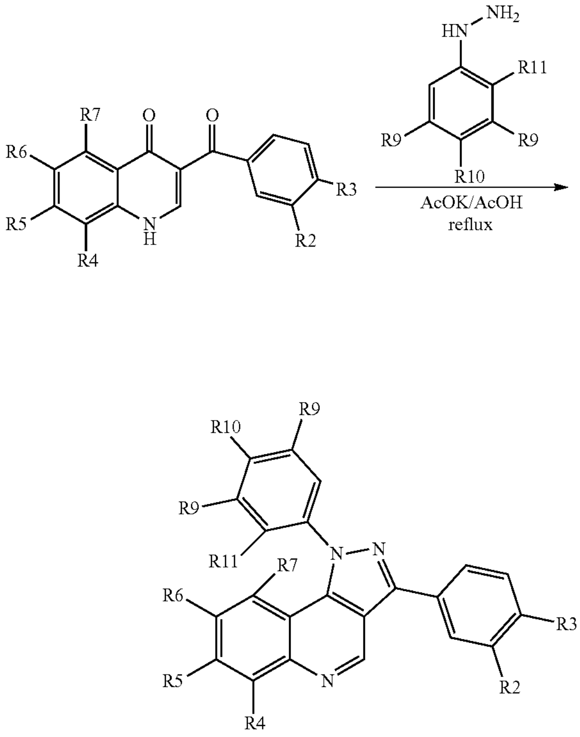

and subsequently;

(e) synthesis of substituted 1,3-diphenylpyrazolo[4,3-c]quinoline by further modification of functional groups such as substitution of halogen (by amine, arylation by boronic acid, etc.), or by etherification, hydrolysis, oxidation, or reduction appropriate functional groups.

As a none limited example of such kind of modification can be halogen substitution in any aromatic ring of the system:

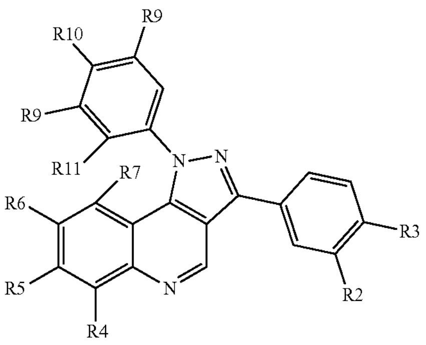

-continued
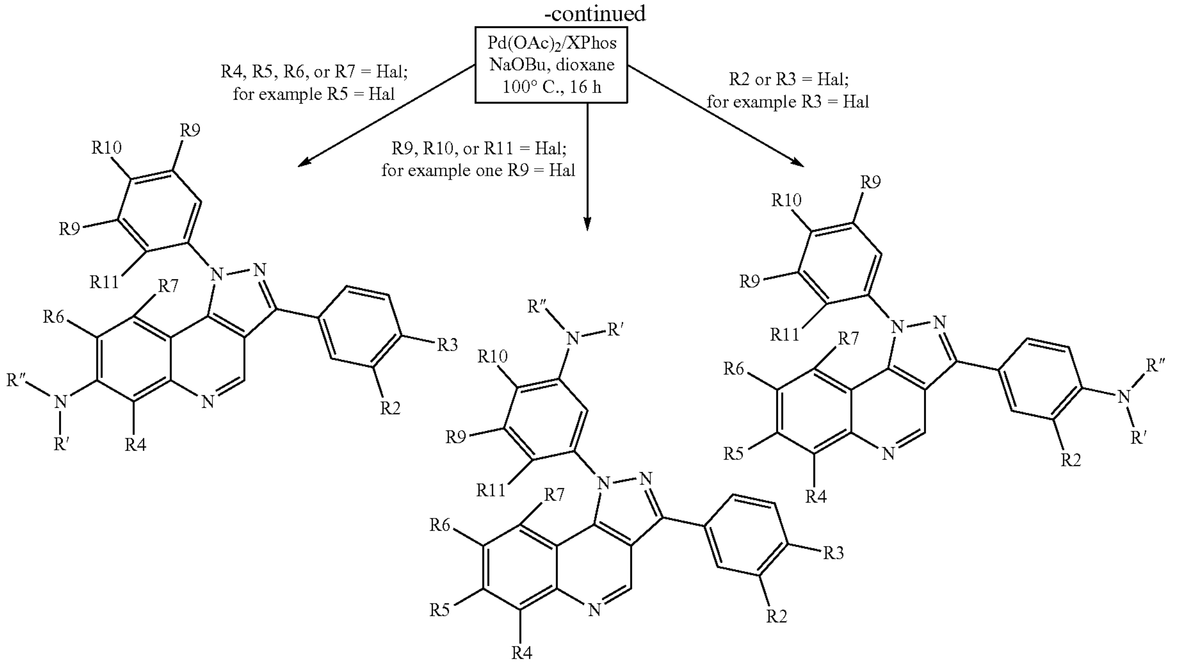
General Procedure B
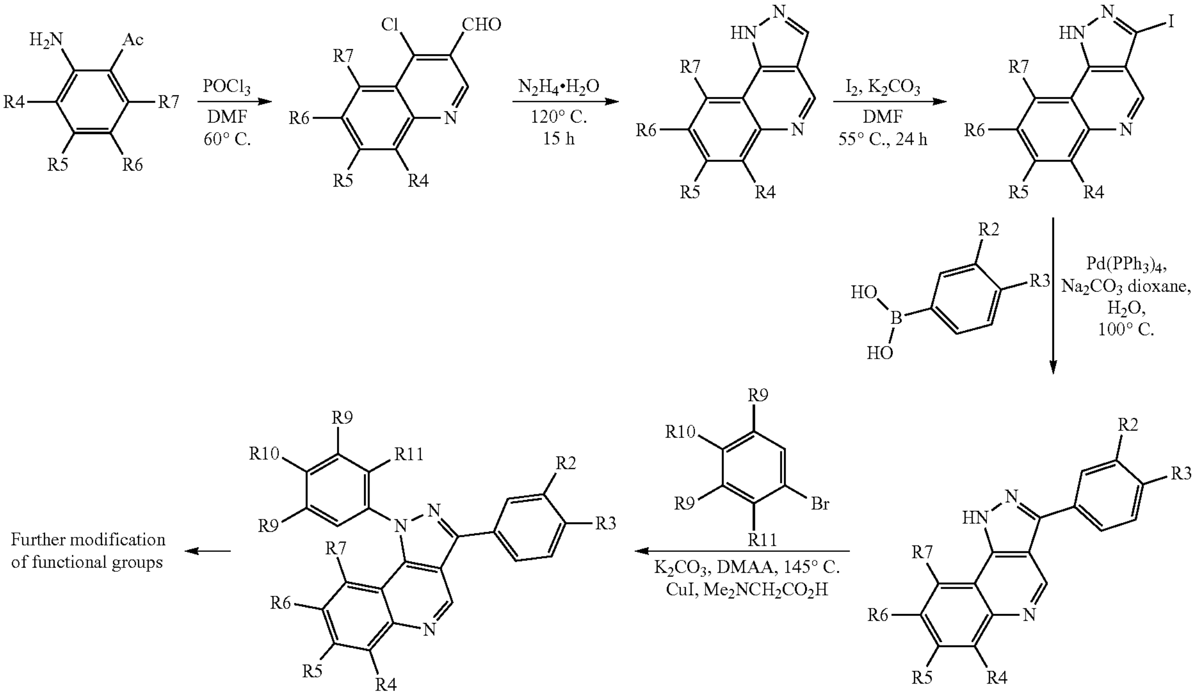

The method of synthesis of the compound of Formula I according to the General Procedure B comprising:

(a) synthesizing substituted 4-chloroquinoline-3-carbaldehyde

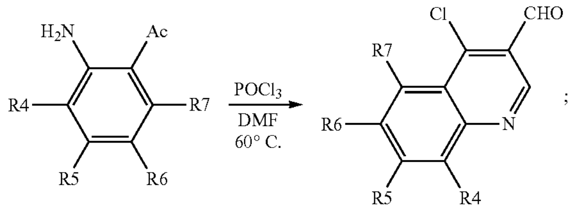

(b) synthesizing of substituted 1H-pyrazolo[4,3-c]quinoline

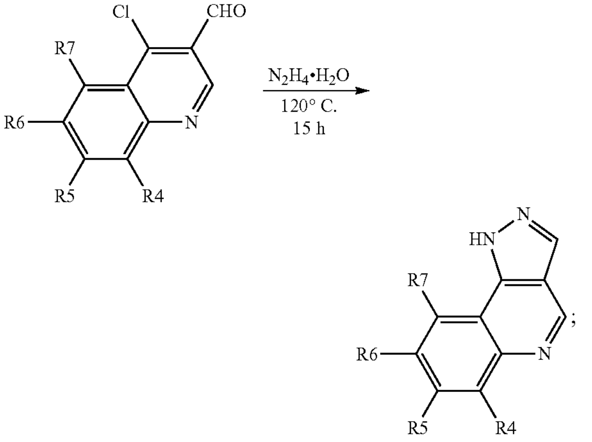

(c) synthesizing of substituted 3-iodo-1H-pyrazolo[4,3-c]quinoline

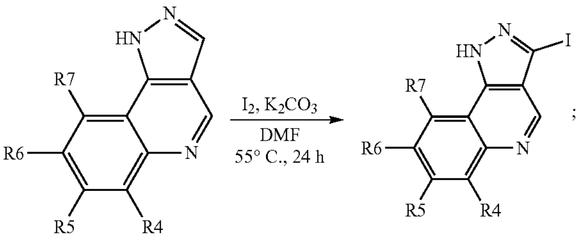

(d) synthesizing of substituted 3-phenyl-1H-pyrazolo[4,3-c]quinoline

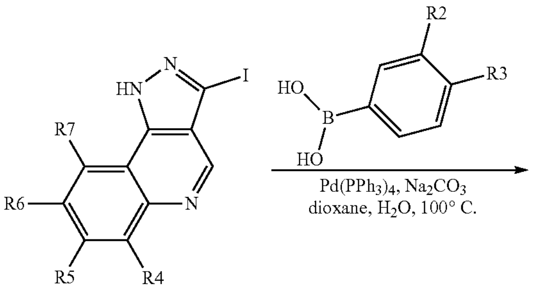

-continued

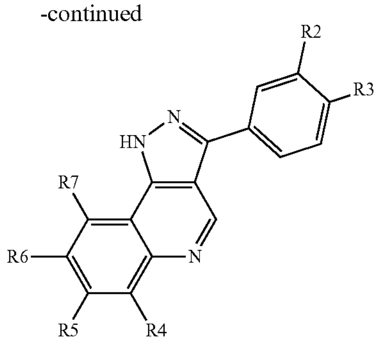

and subsequently;

(e) synthesis of substituted 1,3-diphenylpyrazolo[4,3-c]quinoline

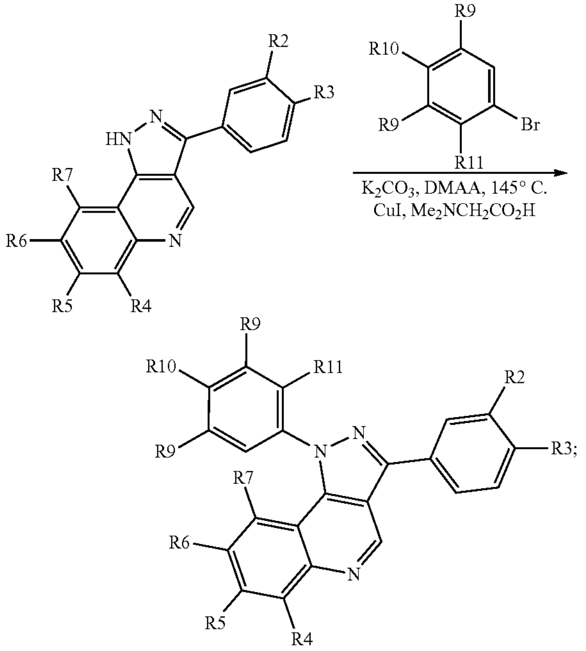

(f) synthesis of substituted 1,3-diphenylpyrazolo[4,3-c]quinoline by further modification of functional groups such as substitution of halogen (by amine, arylation by boronic acid, etc.), or by etherification, hydrolysis, oxidation, or reduction appropriate functional groups.

Methods of Using the Disclosed Compounds

Another aspect of the invention relates to a method of treating a disease or disorder associated with modulation of hematopoietic progenitor kinase 1 (HPK1). The method comprises administering to a patient in need of a treatment for diseases or disorders associated with modulation of HPK1 an effective amount the compositions and compounds of Formula (I).

In another aspect, the present invention is directed to a method of inhibiting hematopoietic progenitor kinase 1 (HPK1). The method involves administering to a patient in need thereof an effective amount of a compound of Formula (I).

Another aspect of the present invention relates to a method of treating, preventing, inhibiting or eliminating a disease or disorder in a patient associated with the inhibition of hematopoietic progenitor kinase 1 (HPK1), the method comprising administering to a patient in need thereof an effective amount of a compound of Formula (I). In one embodiment, the disease may be, but not limited to, cancer.

The present invention also relates to the use of an inhibitor of hematopoietic progenitor kinase 1 (HPK1) for the preparation of a medicament used in the treatment, prevention, inhibition or elimination of a disease or condition mediated by HPK1, wherein the medicament comprises a compound of Formula (I).

In another aspect, the present invention relates to a method for the manufacture of a medicament for treating, preventing, inhibiting, or eliminating a disease or condition mediated by hematopoietic progenitor kinase 1 (HPK1), wherein the medicament comprises a compound of Formula (I).

Another aspect of the present invention relates to a compound of Formula (I) for use in the manufacture of a medicament for treating a disease associated with inhibiting hematopoietic progenitor kinase 1 (HPK1).

In another aspect, the present invention relates to the use of a compound of Formula (I) in the treatment of a disease associated with inhibiting hematopoietic progenitor kinase 1 (HPK1).

Another aspect of the invention relates to a method of treating a disease or disorder associated with modulation of FMS-like tyrosine kinase 3 (FLT3) gene. The method comprises administering to a patient in need of a treatment for diseases or disorders associated with modulation of FLT3 an effective amount the compositions and compounds of Formula (I).

In another aspect, the present invention is directed to a method of inhibiting FMS-like tyrosine kinase 3 (FLT3) gene. The method involves administering to a patient in need thereof an effective amount of a compound of Formula (I).

Another aspect of the present invention relates to a method of treating, preventing, inhibiting or eliminating a disease or disorder in a patient associated with the inhibition of FMS-like tyrosine kinase 3 (FLT3) gene, the method comprising administering to a patient in need thereof an effective amount of a compound of Formula (I).

The present invention also relates to the use of an inhibitor of FMS-like tyrosine kinase 3 (FLT3) gene for the preparation of a medicament used in the treatment, prevention, inhibition or elimination of a disease or condition mediated by FLT3, wherein the medicament comprises a compound of Formula (I).

In another aspect, the present invention relates to a method for the manufacture of a medicament for treating, preventing, inhibiting, or eliminating a disease or condition mediated by FMS-like tyrosine kinase 3 (FLT3) gene, wherein the medicament comprises a compound of Formula (I).

Another aspect of the present invention relates to a compound of Formula (I) for use in the manufacture of a medicament for treating a disease associated with inhibiting FMS-like tyrosine kinase 3 (FLT3) gene.

In another aspect, the present invention relates to the use of a compound of Formula (I) in the treatment of a disease associated with inhibiting FMS-like tyrosine kinase 3 (FLT3) gene.

In some embodiments, the FMS-like tyrosine kinase 3 (FLT3) gene is a mutant FLT3 gene.

Another aspect of the invention relates to a method of treating cancer. The method comprises administering to a patient in need thereof an effective amount of a compound of Formula (I).

Another aspect of the invention relates to a method of treating or preventing cancer. The method comprises administering to a patient in need thereof an effective amount of a compound of Formula (I).

In one embodiment, the present invention relates to the use of an inhibitor of hematopoietic progenitor kinase 1 (HPK1) for the preparation of a medicament used in treatment, prevention, inhibition or elimination of a disease or disorder associated with cancer.

In some embodiments, the disease, disorder, or condition is selected from cancer, an autoimmune disease, HBV, HIV, cancer, and/or a hyper-proliferative disease.

In some embodiments, the disease, disorder, or condition is cancer.

In some embodiments, the cancer is selected from bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL), chronic lymphocytic leukemia/small lymphocytic lymphoma (CLL/SLL), acute myeloid leukemia (AML), and acute promyelocytic leukemia (APL).

In some embodiments, the cancer is selected from the group consisting of bladder cancer, breast cancer, colorectal cancer, gastric cancer, head and neck squamous cell carcinoma, Hodgkin lymphoma, Merkel-cell carcinoma, mesothelioma, melanoma, non-small cell lung cancer, lung cancer, ovarian cancer, pancreatic cancer, prostate cancer, renal cell carcinoma, small cell lung cancer, transitional cell carcinoma, and urothelial cancer. In some embodiments, the cancer is a solid tumor.

In some embodiments, the disease, disorder, or condition is an autoimmune disease.

In some embodiments, the autoimmune disease is selected from chronic obstructive pulmonary disease (COPD), asthma, bronchitis, lupus, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease, interferonopathy, atherosclerosis, and amyotrophic lateral sclerosis.

In some embodiments, the inflammatory bowel disease is selected from Crohn's disease and ulcerative colitis.

In some embodiments, the disease, disorder, or condition is a viral infection.

In some embodiments, the viral infection is an infection by a virus selected from human adenovirus, human cytomegalovirus, Kaposi's sarcoma-associated herpesvirus, hepatitis A virus (HAV), hepatitis B virus (HBV), hepatitis C virus (HCV), Epstein-Barr virus, human immunodeficiency virus (HIV), HPS-associated hantaviruses, Sin Nombre virus, rotavirus, echovirus, foot-and-mouth disease virus, coxsackievirus, West Nile virus, Ebola virus, Ross River virus, human papillomavirus, and coronavirus.

In some embodiments, the viral infection is an infection by hepatitis B virus (HBV).

In some embodiments, the viral infection is an infection by human immunodeficiency virus (HIV).

In some embodiments, the disease, disorder, or condition is male fertility control.

In some embodiments, the disease, disorder, or condition is a benign hyperplasia.

In some embodiments, the benign hyperplasia is selected from benign hyperplasia of the prostate gland and benign hyperplasia of the mammary gland.

In some embodiments, the disease, disorder, or condition is sepsis.

In some embodiments, the disease, disorder, or condition is a vascular disorder.

In some embodiments, the vascular disorder is selected from erythromelalgia, peripheral artery disease, renal artery stenosis, Buerger's disease, Raynaud's disease, disseminated intravascular coagulation, and cerebrovascular disease.

In some embodiments, the disease, disorder, or condition is an atherosclerotic disorder.

In some embodiments, the atherosclerotic disease is selected from myocardial infarction and stroke.

In some embodiments, the disease, disorder, or condition is a neurodegenerative disorder.

In some embodiments, the neurodegenerative disorder is selected from Alzheimer's disease, vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease.

Another aspect of the invention is directed to pharmaceutical compositions comprising a compound of Formula (I) and a pharmaceutically acceptable carrier. The pharmaceutical acceptable carrier may further include an excipient, diluent, or surfactant.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate. Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant. In some embodiments, the pharmaceutical composition can further comprise an additional pharmaceutically active agent. In some embodiments, the additional therapeutic agent is selected from an immune checkpoint inhibitor, a cell-based therapy, and a cytokine therapy.

In some embodiments, the immune checkpoint antibody is selected from a PD-1 antibody, a PD-L1 antibody, a PD-L2 antibody, a CTLA-4 antibody, a TIM3 antibody, a LAG3 antibody, and a TIGIT antibody.

In some embodiments, the immune checkpoint inhibitor is an anti-PD-1 antibody.

In some embodiments, the immune checkpoint inhibitor is an anti-PD-L1 antibody.

In some embodiments, the cell-based therapy is a cancer vaccine.

In some embodiments, the cancer vaccine is selected from an anti-tumor vaccine or a vaccine based on neoantigens.

Cell-based therapies usually involve the removal of immune cells from a subject suffering from cancer, either from the blood or from a tumor. Immune cells specific for the tumor will be activated, grown, and returned to a subject suffering from cancer where the immune cells provide an immune response against the cancer.

In some embodiments, the immune cells are selected from natural killer cells, lymphokine-activated killer cells, cytotoxic T-cells, and dendritic cells.

In some embodiments, the cancer vaccine is natural killer cell-based.

In some embodiments, the cancer vaccine is lymphokine-activated killer cell-based.

In some embodiments, the cancer vaccine is cytotoxic T-cell-based.

In some embodiments, the cancer vaccine is dendritic cell-based.

In some embodiments, the cell-based therapy is selected from CAR-T therapy (e.g., chimeric antigen receptor T-cells which are T-cells engineered to target specific antigens), TIL therapy (e.g., administration of tumor-infiltrating lymphocytes), and TCR gene therapy.

In some embodiments, the cytokine therapy is interleukin-2 therapy.

In some embodiments, the cytokine therapy is interferon-alpha therapy.

Compositions can be prepared according to conventional mixing, granulating or coating methods, respectively, and the present pharmaceutical compositions can contain from about 0.10% to about 99%, from about 5% to about 90%, or from about 10% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

In some embodiments, the use in a method of inhibiting the growth or proliferation of cancer cells in a subject in need thereof further comprises administering one or more additional therapeutic agents selected from the group consisting of Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAMI inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, CD73 inhibitors, inhibitory RNA, IL2/15/17 fusion proteins, MKNK1/2 inhibitors, JAK inhibitors, and PI3K inhibitors, or a pharmaceutically acceptable salt of any of the foregoing, or any combinations thereof.

In some embodiments, the use in a method of inhibiting the growth or proliferation of cancer cells in a subject in need thereof further comprises administering one or more additional therapeutic agents selected from the group consisting of rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino)pyrimidin-4-yl]benzamide, XL147, BKM120, GDC-0941, BAY80-6946, PX-866, CH5132799, XL756, BEZ235, and GDC-0980, wortmannin, LY294002, TGR1202, AMG-319, GSK2269557, X-339, X-414, RP5090, KAR4141, XL499, OXY111A, IPI145, IPI-443, GSK2636771, BAY 10824391, buparlisib, BYL719, RG7604, MLN1117, WX037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9Hpurin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbonitrile, and ipilimumab, or a pharmaceutically acceptable salt of any of the foregoing, or any combinations thereof.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations

AcOH Acetic acid
AcOK Potassium acetate
Anh. Anhydrous
ATP Adenosine triphosphate
br. Broad
aq. Aqueous
BSA Bovine serum albumin
CC Column chromatography (e.g. silica CC)
CDI 1,1'-Carbonyldiimidazole
DCM Dichloromethane
DMAA 1,3-Dimethylamylamine
DMF N,N-dimethyl formamide
DMF-DMA N,N-dimethylformamide dimethyl acetal
DMSO Dimethyl sulfoxide
DTT Dithiothreitol
$Et_2O$ Diethyl ether
EtOAc Ethyl acetate
EtOH Ethanol
FC Flash chromatography
h Hour(s)
HPLC High pressure (or performance) liquid chromatography
i-PrOAc Isopropyl acetate
LCMS Liquid chromatography-mass spectrometry
m Multiplet
M Molar
MBP Native Swine Myelin Basic Protein MeOH Methanol
MHz Megahertz
min Minutes
MS Molecular sieves or mass spectroscopy
MTBE Methyl-t-Butyl Ether
NBS N-bromosuccinimide
NMR Nuclear magnetic resonance
NOESY Nuclear Overhauser Effect Spectroscopy
PEG Polyethylene glycol
$Ph_2O$ Diphenyl ether (diphenyl oxide)
rt Room temperature
t-BuONa Sodium tert-butoxide
TFA Trifluoroacetic acid
TRIS-HCl Tris(hydroxymethyl)aminomethane hydrochloride
XPhos 2-Dicyclohexylphosphino-2',4',6'-triisopropylbiphenyl Purity and identity of all synthesized compounds were confirmed by LC-MS analysis performed on Shimadzu Analytical 10Avp equipped with PE SCIEX API 165 mass-, Sedex 75 ELSD-, and Shimadzu UV- (254 and 215) detectors. Separation was achieved with C18 column 100×4.6 mm, 5.0 µm, pore size 100 Å, water-acetonitrile+0.1 TFA, gradient 5 to 87 for 10 min.

Preparative HPLC purification was carried out on Shimadzu instrument equipped with SPD-10Avp detector and FRC-10A fraction collector. Separation was achieved with a column YMC-Pack ODS-AQ 250×20 mml, S-10 µm, 12 nm, gradient solution A-solution B (A: 1000 mL $H_2O$-226 µL TFA; B: 1000 mL $CH_3CN$-226 µL TFA).

In the Table 1 presented examples of the compound synthesized in the frame of this invention, results of MS analysis and ID numbers for each compound for the further reference.

TABLE 1

Examples of the compounds and analytical data

| Cmpd # | IUPAC name | MS calc. [MH+] | MS found [MH+] |
|---|---|---|---|
| 1.1 | 1-{3-[1-(3,4-dimethylphenyl)-8-methoxy-1H-pyrazolo[4,3-c]quinolin-3-yl]phenyl}-N,N-dimethylpiperidin-4-amine | 506.29 | 506 |
| 1.2 | 4-{3-[1-(3,4-dimethylphenyl)-8-methoxy-1H-pyrazolo[4,3-c]quinolin-3-yl]phenyl}morpholine | 465.22 | 465 |
| 1.3 | 1-{3-[1-(3,4-dimethylphenyl)-8-methoxy-1H-pyrazolo[4,3-c]quinolin-3-yl]phenyl}-4-methylpiperazine | 478.26 | 478 |
| 1.4 | 1-{3-[8-methoxy-3-(3-methoxyphenyl)-1H-pyrazolo[4,3-c]quinolin-1-yl]phenyl}-N,N-dimethylpiperidin-4-amine | 508.27 | 508 |
| 1.5 | 1-{3-[8-methoxy-3-(3-methoxyphenyl)-1H-pyrazolo[4,3-c]quinolin-1-yl]phenyl}-4-methylpiperazine | 480.24 | 480 |
| 1.7 | 1-{3-[8-methoxy-3-(3-methoxyphenyl)-1H-pyrazolo[4,3-c]quinolin-1-yl]-4-methylphenyl}-N,N-dimethylpiperidin-4-amine | 522.29 | 522 |
| 1.8 | 1-{3-[8-methoxy-3-(3-methoxyphenyl)-1H-pyrazolo[4,3-c]quinolin-1-yl]-4-methylphenyl}-4-methylpiperazine | 494.26 | 494 |
| 1.10 | 1-{3-[3-(3,4-dimethylphenyl)-8-methoxy-1H-pyrazolo[4,3-c]quinolin-1-yl]-4-methylphenyl}-N,N-dimethylpiperidin-4-amine | 520.31 | 520 |
| 1.11 | 1-{3-[3-(3,4-dimethylphenyl)-8-methoxy-1H-pyrazolo[4,3-c]quinolin-1-yl]-4-methylphenyl}-4-methylpiperazine | 492.28 | 492 |
| 1.13 | 1-{3-[3-(3,4-dimethylphenyl)-8-methoxy-1H-pyrazolo[4,3-c]quinolin-1-yl]phenyl}-N,N-dimethylpiperidin-4-amine | 506.29 | 506 |

TABLE 1-continued

Examples of the compounds and analytical data

| Cmpd # | IUPAC name | MS calc. [MH+] | MS found [MH+] |
|---|---|---|---|
| 1.14 | 1-{3-[1-(2,3-dimethylphenyl)-8-methoxy-1H-pyrazolo[4,3-c]quinolin-3-yl]phenyl}-N,N-dimethylpiperidin-4-amine | 506.29 | 506 |
| 1.15 | 4-{4-[1-(3,4-dimethylphenyl)-8-methoxy-1H-pyrazolo[4,3-c]quinolin-3-yl]phenyl}morpholine | 465.22 | 465 |
| 1.16 | 1-{4-[1-(3,4-dimethylphenyl)-8-methoxy-1H-pyrazolo[4,3-c]quinolin-3-yl]phenyl}-4-methylpiperazine | 478.26 | 478 |
| 1.17 | 1-{4-[1-(3,4-dimethylphenyl)-8-methoxy-1H-pyrazolo[4,3-c]quinolin-3-yl]phenyl}-N,N-dimethylpiperidin-4-amine | 506.29 | 506 |
| 1.18 | N-[3-(dimethylamino)propyl]-4-[1-(3,4-dimethylphenyl)-8-methoxy-1H-pyrazolo[4,3-c]quinolin-3-yl]-N-methylaniline | 494.29 | 494 |
| 1.19 | 4-{4-[1-(3,4-dimethylphenyl)-8-methoxy-1H-pyrazolo[4,3-c]quinolin-3-yl]phenyl}pyridine | 457.20 | 457 |
| 1.20 | 4-{4-[1-(3,4-dimethylphenyl)-1H-pyrazolo[4,3-c]quinolin-3-yl]phenyl}morpholine | 435.22 | 435 |
| 1.21 | 1-{4-[1-(3,4-dimethylphenyl)-1H-pyrazolo[4,3-c]quinolin-3-yl]phenyl}-4-methylpiperazine | 448.25 | 448 |
| 1.22 | 1-{4-[1-(3,4-dimethylphenyl)-1H-pyrazolo[4,3-c]quinolin-3-yl]phenyl}piperazine | 434.23 | 434 |
| 1.23 | 4-(4-{1-phenyl-1H-pyrazolo[4,3-c]quinolin-3-yl}phenyl)morpholine | 407.18 | 407 |
| 1.24 | (2-{4-[1-(3,4-dimethylphenyl)-8-methoxy-1H-pyrazolo[4,3-c]quinolin-3-yl]-2-methoxyphenoxy}ethyl)dimethylamine | 497.26 | 497 |
| 1.25 | 4-(2-{4-[1-(3,4-dimethylphenyl)-8-methoxy-1H-pyrazolo[4,3-c]quinolin-3-yl]-2-methoxyphenoxy}ethyl)morpholine | 539.27 | 539 |
| 1.26 | 4-(3-{4-[1-(3,4-dimethylphenyl)-8-methoxy-1H-pyrazolo[4,3-c]quinolin-3-yl]-2-methoxyphenoxy}propyl)morpholine | 553.28 | 553 |
| 1.27 | 3-(2H-1,3-benzodioxol-5-yl)-1-(3,4-dimethylphenyl)-1H-pyrazolo[4,3-c]quinoline | 394.16 | 394 |
| 1.28 | 3-(2H-1,3-benzodioxol-5-yl)-1-phenyl-1H-pyrazolo[4,3-c]quinoline | 366.12 | 366 |
| 1.29 | 3-(2H-1,3-benzodioxol-5-yl)-1-(3,4-dimethylphenyl)-8-methoxy-1H-pyrazolo[4,3-c]quinoline | 424.17 | 424 |
| 1.30 | 3-(2H-1,3-benzodioxol-5-yl)-8-methoxy-1-phenyl-1H-pyrazolo[4,3-c]quinoline | 396.13 | 396 |
| 1.31 | 7-[3-(3,4-dimethoxyphenyl)-1H-pyrazolo[4,3-c]quinolin-1-yl]-1,2,3,4-tetrahydroisoquinoline | 437.20 | 437 |
| 1.32 | 6-[3-(3,4-dimethoxyphenyl)-1H-pyrazolo[4,3-c]quinolin-1-yl]-1,2,3,4-tetrahydroisoquinoline | 437.20 | 437 |
| 1.33 | 5-[3-(3,4-dimethoxyphenyl)-1H-pyrazolo[4,3-c]quinolin-1-yl]-2,3-dihydro-1H-isoindole | 423.18 | 423 |
| 1.34 | 7-[3-(3,4-dimethoxyphenyl)-8-methoxy-1H-pyrazolo[4,3-c]quinolin-1-yl]-1,2,3,4-tetrahydroisoquinoline | 467.21 | 467 |
| 1.35 | 6-[3-(3,4-dimethoxyphenyl)-8-methoxy-1H-pyrazolo[4,3-c]quinolin-1-yl]-1,2,3,4-tetrahydroisoquinoline | 467.21 | 467 |
| 1.36 | 5-[3-(3,4-dimethoxyphenyl)-8-methoxy-1H-pyrazolo[4,3-c]quinolin-1-yl]-2,3-dihydro-1H-isoindole | 453.19 | 453 |
| 1.37 | 7-[3-(3,4-dimethoxyphenyl)-6-methoxy-1H-pyrazolo[4,3-c]quinolin-1-yl]-1,2,3,4-tetrahydroisoquinoline | 467.21 | 467 |

TABLE 1-continued

Examples of the compounds and analytical data

| Cmpd # | IUPAC name | MS calc. [MH+] | MS found [MH+] |
|---|---|---|---|
| 1.38 | 6-[3-(3,4-dimethoxyphenyl)-6-methoxy-1H-pyrazolo[4,3-c]quinolin-1-yl]-1,2,3,4-tetrahydroisoquinoline | 467.21 | 467 |
| 1.39 | 5-[3-(3,4-dimethoxyphenyl)-6-methoxy-1H-pyrazolo[4,3-c]quinolin-1-yl]-2,3-dihydro-1H-isoindole | 453.19 | 453 |
| 1.40 | 4-{2-[3-(3,4-dimethoxyphenyl)-8-methoxy-1H-pyrazolo[4,3-c]quinolin-1-yl]ethyl}morpholine | 449.22 | 449 |
| 1.41 | 1-{3-[1-(3,4-dimethylphenyl)-8-methoxy-1H-pyrazolo[4,3-c]quinolin-3-yl]phenyl}piperazine | 464.25 | 464 |
| 1.42 | N-[3-(dimethylamino)propyl]-3-[1-(3,4-dimethylphenyl)-8-methoxy-1H-pyrazolo[4,3-c]quinolin-3-yl]-N-methylaniline | 494.29 | 494 |
| 1.43 | 4-(2-{5-[1-(3,4-dimethylphenyl)-8-methoxy-1H-pyrazolo[4,3-c]quinolin-3-yl]-2-methoxyphenoxy}ethyl)morpholine | 539.27 | 539 |
| 1.44 | (2-{5-[1-(3,4-dimethylphenyl)-8-methoxy-1H-pyrazolo[4,3-c]quinolin-3-yl]-2-methoxyphenoxy}ethyl)dimethylamine | 497.26 | 497 |
| 1.45 | (2-{4-[1-(3,4-dimethylphenyl)-1H-pyrazolo[4,3-c]quinolin-3-yl]-2-methoxyphenoxy}ethyl)dimethylamine | 467.24 | 467 |
| 1.46 | 4-(2-{4-[1-(3,4-dimethylphenyl)-1H-pyrazolo[4,3-c]quinolin-3-yl]-2-methoxyphenoxy}ethyl)morpholine | 509.26 | 509 |
| 1.47 | 4-(2-{5-[1-(3,4-dimethylphenyl)-1H-pyrazolo[4,3-c]quinolin-3-yl]-2-methoxyphenoxy}ethyl)morpholine | 509.26 | 509 |
| 1.48 | (2-{5-[1-(3,4-dimethylphenyl)-1H-pyrazolo[4,3-c]quinolin-3-yl]-2-methoxyphenoxy}ethyl)dimethylamine | 467.24 | 467 |
| 1.49 | [2-(2-methoxy-4-{1-phenyl-1H-pyrazolo[4,3-c]quinolin-3-yl}phenoxy)ethyl]dimethylamine | 439.21 | 439 |
| 1.50 | 4-[2-(2-methoxy-4-{1-phenyl-1H-pyrazolo[4,3-c]quinolin-3-yl}phenoxy)ethyl]morpholine | 481.22 | 481 |
| 1.51 | [2-(2-methoxy-4-{8-methoxy-1-phenyl-1H-pyrazolo[4,3-c]quinolin-3-yl}phenoxy)ethyl]dimethylamine | 469.22 | 469 |
| 1.52 | 4-[2-(2-methoxy-4-{8-methoxy-1-phenyl-1H-pyrazolo[4,3-c]quinolin-3-yl}phenoxy)ethyl]morpholine | 511.23 | 511 |
| 1.53 | 4-[2-(2-methoxy-5-{1-phenyl-1H-pyrazolo[4,3-c]quinolin-3-yl}phenoxy)ethyl]morpholine | 481.22 | 481 |
| 1.54 | [2-(2-methoxy-5-{1-phenyl-1H-pyrazolo[4,3-c]quinolin-3-yl}phenoxy)ethyl]dimethylamine | 439.21 | 439 |
| 1.55 | 4-[2-(2-methoxy-5-{8-methoxy-1-phenyl-1H-pyrazolo[4,3-c]quinolin-3-yl}phenoxy)ethyl]morpholine | 511.23 | 511 |
| 1.56 | [2-(2-methoxy-5-{8-methoxy-1-phenyl-1H-pyrazolo[4,3-c]quinolin-3-yl}phenoxy)ethyl]dimethylamine | 469.22 | 469 |
| 1.57 | 4-(2-{4-[1-(3,4-dimethylphenyl)-8-methyl-1H-pyrazolo[4,3-c]quinolin-3-yl]-2-methoxyphenoxy}ethyl)morpholine | 523.27 | 523 |
| 1.58 | 4-(2-{4-[1-(2,4-dimethylphenyl)-8-methyl-1H-pyrazolo[4,3-c]quinolin-3-yl]-2-methoxyphenoxy}ethyl)morpholine | 523.27 | 523 |
| 1.59 | 4-(2-{4-[1-(2,3-dimethylphenyl)-8-methyl-1H-pyrazolo[4,3-c]quinolin-3-yl]-2-methoxyphenoxy}ethyl)morpholine | 523.27 | 523 |
| 1.60 | 4-(2-{4-[1-(2,5-dimethylphenyl)-8-methyl-1H-pyrazolo[4,3-c]quinolin-3-yl]-2-methoxyphenoxy}ethyl)morpholine | 523.27 | 523 |

TABLE 1-continued

Examples of the compounds and analytical data

| Cmpd # | IUPAC name | MS calc. [MH+] | MS found [MH+] |
|---|---|---|---|
| 1.61 | 4-(2-{4-[1-(3-chloro-2-methylphenyl)-8-methyl-1H-pyrazolo[4,3-c]quinolin-3-yl]-2-methoxyphenoxy}ethyl)morpholine | 543.22 | 543 |
| 1.62 | 4-(2-{4-[1-(3,4-dimethylphenyl)-8-(trifluoromethoxy)-1H-pyrazolo[4,3-c]quinolin-3-yl]-2-methoxyphenoxy}ethyl)morpholine | 593.24 | 593 |
| 1.63 | 4-(2-chloro-4-{1-phenyl-1H-pyrazolo[4,3-c]quinolin-3-yl}phenyl)morpholine | 441.15 | 441 |
| 1.64 | 1-(2-chloro-4-{1-phenyl-1H-pyrazolo[4,3-c]quinolin-3-yl}phenyl)piperazine | 440.16 | 440 |
| 1.65 | 1-(2-chloro-4-{1-phenyl-1H-pyrazolo[4,3-c]quinolin-3-yl}phenyl)-4-methylpiperazine | 454.18 | 454 |
| 1.66 | 4-(2-chloro-4-{8-methoxy-1-phenyl-1H-pyrazolo[4,3-c]quinolin-3-yl}phenyl)morpholine | 471.16 | 471 |
| 1.67 | 1-(2-chloro-4-{8-methoxy-1-phenyl-1H-pyrazolo[4,3-c]quinolin-3-yl}phenyl)piperazine | 470.17 | 470 |
| 1.68 | 1-(2-chloro-4-{8-methoxy-1-phenyl-1H-pyrazolo[4,3-c]quinolin-3-yl}phenyl)-4-methylpiperazine | 484.19 | 484 |
| 1.69 | 4-{2-chloro-4-[1-(3,4-dimethylphenyl)-1H-pyrazolo[4,3-c]quinolin-3-yl]phenyl}morpholine | 469.18 | 469 |
| 1.70 | 1-{2-chloro-4-[1-(3,4-dimethylphenyl)-1H-pyrazolo[4,3-c]quinolin-3-yl]phenyl}piperazine | 468.20 | 468 |
| 1.71 | 1-{2-chloro-4-[1-(3,4-dimethylphenyl)-1H-pyrazolo[4,3-c]quinolin-3-yl]phenyl}-4-methylpiperazine | 482.21 | 482 |
| 1.72 | 4-{2-chloro-4-[1-(3,4-dimethylphenyl)-8-methoxy-1H-pyrazolo[4,3-c]quinolin-3-yl]phenyl}morpholine | 499.19 | 499 |
| 1.73 | 1-{2-chloro-4-[1-(3,4-dimethylphenyl)-8-methoxy-1H-pyrazolo[4,3-c]quinolin-3-yl]phenyl}piperazine | 498.21 | 498 |
| 1.74 | 1-{2-chloro-4-[1-(3,4-dimethylphenyl)-8-methoxy-1H-pyrazolo[4,3-c]quinolin-3-yl]phenyl}-4-methylpiperazine | 512.22 | 512 |
| 1.75 | 4-(4-{8-methoxy-1-phenyl-1H-pyrazolo[4,3-c]quinolin-3-yl}phenyl)morpholine | 437.20 | 437 |
| 1.76 | 1-(4-{8-methoxy-1-phenyl-1H-pyrazolo[4,3-c]quinolin-3-yl}phenyl)-4-methylpiperazine | 450.23 | 450 |
| 1.77 | 1-(4-{1-phenyl-1H-pyrazolo[4,3-c]quinolin-3-yl}phenyl)piperazine | 406.20 | 406 |
| 1.78 | 1-{3-[3-(3,4-dimethylphenyl)-8-methoxy-1H-pyrazolo[4,3-c]quinolin-1-yl]phenyl}-4-methylpiperazine | 478.26 | 478 |

Intermediates

In the Table 2 presented examples of the intermediates synthesized in the frame of this invention and useful for the preparation of the compounds described in the invention, results of MS analysis and ID numbers for each compound for the further reference.

TABLE 2

Examples of intermediates useful for the compound's preparation.

| Cmpd # | IUPAC name | MS calc. [MH+] | MS found [MH+] |
|---|---|---|---|
| P12 | 3-(1,3-benzodioxole-5-carbonyl)-6-methoxy-1H-quinolin-4-one | 324.09 | 324 |
| P16 | 4-chloro-6-(trifluoromethoxy)quinoline-3-carbaldehyde | 276.00 | 276 |

In the Table 3 presented examples of the intermediates synthesized in the frame of this invention and useful for the preparation of the compounds described in the invention, results of MS analysis and ID numbers for each compound for the further reference.

TABLE 3

Examples of intermediates useful for the compound's preparation.

| Cmpd # | IUPAC name | MS calc. [MH+] | MS found [MH+] |
|---|---|---|---|
| P18 | 8-methoxy-1H-pyrazolo[4,3-c]quinoline | 200.08 | 200 |
| P19 | 6-methoxy-1H-pyrazolo[4,3-c]quinoline | 200.08 | 200 |

In the Table 4 presented examples of the intermediates synthesized in the frame of this invention and useful for the preparation of the compounds described in the invention, results of MS analysis and ID numbers for each compound for the further reference.

TABLE 4

Examples of intermediates useful for the compound's preparation.

| Cmpd # | IUPAC name | MS calc. [MH+] | MS found [MH+] |
|---|---|---|---|
| P20 | 3-iodo-1H-pyrazolo[4,3-c]quinoline | 295.97 | 296 |
| P21 | 3-iodo-8-methoxy-1H-pyrazolo[4,3-c]quinoline | 325.98 | 326 |
| P22 | 3-iodo-6-methoxy-1H-pyrazolo[4,3-c]quinoline | 325.98 | 326 |

In the Table 5 presented examples of the intermediates synthesized in the frame of this invention and useful for the preparation of the compounds described in the invention, results of MS analysis and ID numbers for each compound for the further reference.

TABLE 5

Examples of intermediates useful for the compound's preparation.

| Cmpd # | IUPAC name | MS calc. [MH+] | MS found [MH+] |
|---|---|---|---|
| P23 | 3-(3,4-dimethoxyphenyl)-1H-pyrazolo[4,3-c]quinoline | 306.12 | 306 |
| P24 | 3-(3,4-dimethoxyphenyl)-8-methoxy-1H-pyrazolo[4,3-c]quinoline | 336.13 | 336 |
| P25 | 3-(3,4-dimethoxyphenyl)-6-methoxy-1H-pyrazolo[4,3-c]quinoline | 336.13 | 336 |

In the Table 6 presented examples of the intermediates synthesized in the frame of this invention and useful for the preparation of the compounds described in the invention, results of MS analysis and ID numbers for each compound for the further reference.

TABLE 6

Examples of intermediates useful for the compound's preparation.

| Cmpd # | IUPAC name | MS calc. [MH+] | MS found [MH+] |
|---|---|---|---|
| 1.6 P03 | 1-(5-chloro-2-methylphenyl)-8-methoxy-3-(3-methoxyphenyl)-1H-pyrazolo[4,3-c]quinoline | 430.13 | 430 |

TABLE 6-continued

Examples of intermediates useful for the compound's preparation.

| Cmpd # | IUPAC name | MS calc. [MH+] | MS found [MH+] |
|---|---|---|---|
| 1.9 P04 | 1-(5-chloro-2-methylphenyl)-3-(3,4-dimethylphenyl)-8-methoxy-1H-pyrazolo[4,3-c]quinoline | 428.15 | 428 |
| P38 | 4-[1-(3-chloro-2-methylphenyl)-8-methyl-1H-pyrazolo[4,3-c]quinolin-3-yl]-2-methoxyphenol | 430.13 | 430 |

In the Table 7 presented examples of the intermediates synthesized in the frame of this invention and useful for the preparation of the compounds described in the invention, results of MS analysis and ID numbers for each compound for the further reference.

TABLE 7

Examples of intermediates useful for the compound's preparation.

| Cmpd # | IUPAC name | MS calc. [MH+] | MS found [MH+] |
|---|---|---|---|
| 1.12 P05 | 1-(3-bromophenyl)-3-(3,4-dimethylphenyl)-8-methoxy-1H-pyrazolo[4,3-c]quinoline | 458.09 | 458 |
| 1.79 | 1-(3-bromophenyl)-8-methoxy-3-(3-methoxyphenyl)-1H-pyrazolo[4,3-c]quinoline | 460.07 | 460 |
| P02 | 1-(3-bromophenyl)-8-methoxy-3-(3-methoxyphenyl)pyrazolo[4,3-c]quinoline | 460.07 | 460 |

In the Table 8 presented examples of the intermediates synthesized in the frame of this invention and useful for the preparation of the compounds described in the invention, results of MS analysis and ID numbers for each compound for the further reference.

TABLE 8

Examples of intermediates useful for the compound's preparation.

| Cmpd # | IUPAC name | MS calc. [MH+] | MS found [MH+] |
|---|---|---|---|
| P06 | 3-(3-bromophenyl)-1-(2,3-dimethylphenyl)-8-methoxy-pyrazolo[4,3-c]quinoline | 458.09 | 458 |
| P01 | 3-(3-bromophenyl)-1-(3,4-dimethylphenyl)-8-methoxy-pyrazolo[4,3-c]quinoline | 458.09 | 458 |
| P40 | 3-(4-bromo-3-chloro-phenyl)-1-phenyl-pyrazolo[4,3-c]quinoline | 434.01 | 434 |
| P41 | 3-(4-bromo-3-chloro-phenyl)-8-methoxy-1-phenyl-pyrazolo[4,3-c]quinoline | 464.02 | 464 |
| P42 | 3-(4-bromo-3-chloro-phenyl)-1-(3,4-dimethylphenyl)pyrazolo[4,3-c]quinoline | 462.04 | 462 |
| P43 | 3-(4-bromo-3-chloro-phenyl)-1-(3,4-dimethylphenyl)-8-methoxy-pyrazolo[4,3-c]quinoline | 492.05 | 492 |

In the Table 9 presented examples of the intermediates synthesized in the frame of this invention and useful for the preparation of the compounds described in the invention, results of MS analysis and ID numbers for each compound for the further reference.

TABLE 9

| Examples of intermediates useful for the compound's preparation. | | | |
|---|---|---|---|
| Cmpd # | IUPAC name | MS calc. [MH+] | MS found [MH+] |
| P10 | 4-[1-(3,4-dimethylphenyl)-8-methoxy-pyrazolo[4,3-c]quinolin-3-yl]-2-methoxy-phenol | 426.18 | 426 |
| P28 | 4-[1-(3,4-dimethylphenyl)pyrazolo[4,3-c]quinolin-3-yl]-2-methoxy-phenol | 396.17 | 396 |
| P30 | 2-methoxy-4-(1-phenylpyrazolo[4,3-c]quinolin-3-yl)phenol | 368.14 | 368 |
| P31 | 2-methoxy-4-(8-methoxy-1-phenyl-pyrazolo[4,3-c]quinolin-3-yl)phenol | 398.15 | 398 |
| P34 | 4-[1-(3,4-dimethylphenyl)-8-methyl-pyrazolo[4,3-c]quinolin-3-yl]-2-methoxy-phenol | 410.19 | 410 |
| P35 | 4-[1-(2,4-dimethylphenyl)-8-methyl-pyrazolo[4,3-c]quinolin-3-yl]-2-methoxy-phenol | 410.19 | 410 |
| P36 | 4-[1-(2,3-dimethylphenyl)-8-methyl-pyrazolo[4,3-c]quinolin-3-yl]-2-methoxy-phenol | 410.19 | 410 |
| P37 | 4-[1-(2,5-dimethylphenyl)-8-methyl-pyrazolo[4,3-c]quinolin-3-yl]-2-methoxy-phenol | 410.19 | 410 |
| P39 | 4-[1-(3,4-dimethylphenyl)-8-(trifluoromethoxy)pyrazolo[4,3-c]quinolin-3-yl]-2-methoxy-phenol | 480.15 | 480 |

In the Table 10 presented examples of the intermediates synthesized in the frame of this invention and useful for the preparation of the compounds described in the invention, results of MS analysis and ID numbers for each compound for the further reference.

TABLE 10

| Examples of intermediates useful for the compound's preparation. | | | |
|---|---|---|---|
| Cmpd # | IUPAC name | MS calc. [MH+] | MS found [MH+] |
| P27 | 5-[1-(3,4-dimethylphenyl)-8-methoxy-pyrazolo[4,3-c]quinolin-3-yl]-2-methoxy-phenol | 426.18 | 426 |
| P29 | 5-[1-(3,4-dimethylphenyl)pyrazolo[4,3-c]quinolin-3-yl]-2-methoxy-phenol | 396.17 | 396 |
| P32 | 2-methoxy-5-(1-phenylpyrazolo[4,3-c]quinolin-3-yl)phenol | 368.14 | 368 |
| P33 | 2-methoxy-5-(8-methoxy-1-phenyl-pyrazolo[4,3-c]quinolin-3-yl)phenol | 398.15 | 398 |

General Synthetical Procedures and Examples of the Compound's Preparation

Preparation of Intermediates

Preparation 1: 3-(3-bromophenyl)-1-(3,4-dimethylphenyl)-8-methoxy-pyrazolo[4,3-c]quinoline

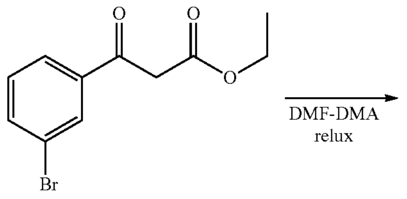

P1-1

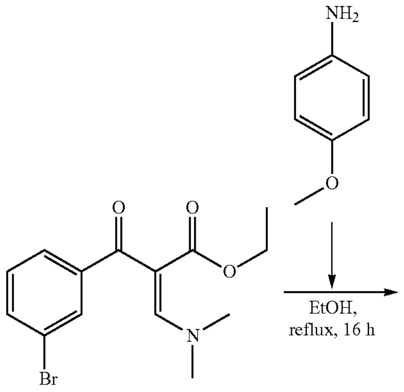

P1-2

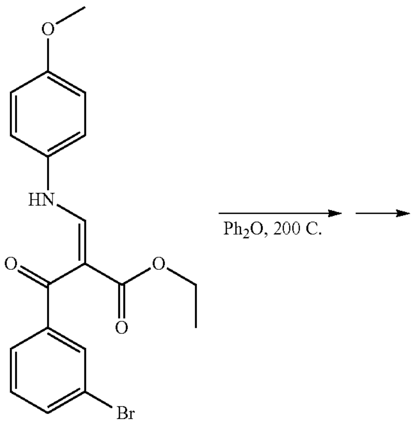

P1-3

-continued

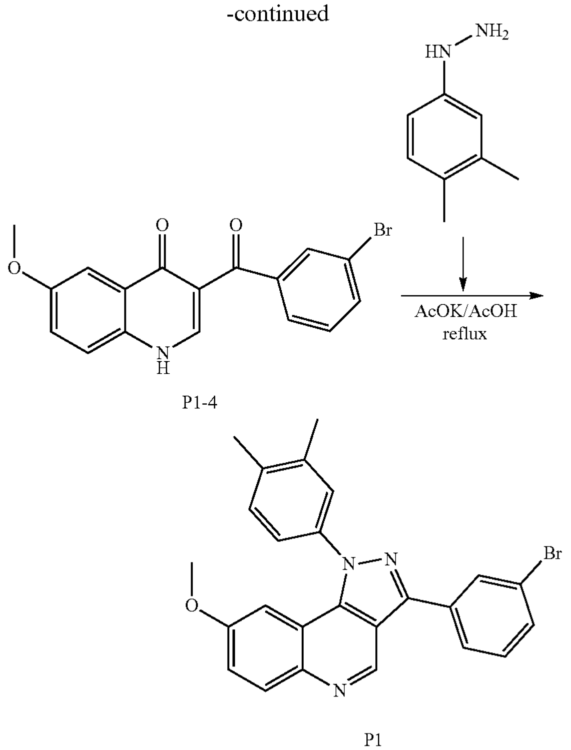

P1-4

P1

A mixture of ethyl 3-(3-bromophenyl)-3-oxopropanoate (P1-1) (6.0 g, 22 mmol) and DMF-DMA (13.2 g, 110 mmol) was stirred and heated under reflux for 8 h, then concentrated under reduced pressure to afford 7.25 g, (100%) of ethyl 2-[(3-bromophenyl)carbonyl]-3-(dimethylamino) prop-2-enoate (P1-2) that was used for the next step without purification.

A mixture of Ethyl 2-[(3-bromophenyl)carbonyl]-3-(dimethylamino)prop-2-enoate (P1-2) (6.4 g, 119 mmol), p-anisidine (2.9 g, 23 mmol), and anh. EtOH (100 mL) was stirred and heated under reflux overnight and then concentrated under reduced pressure. The residue was subjected to silica CC eluting with a mixture of hexane and EtOAc (10:1) to afford 7.0 g (88%) of ethyl 2-[(3-bromophenyl)carbonyl]-3-[(4-methoxyphenyl)amino]prop-2-enoate (P1-3) as a mixture Z- and E-isomers.

Ethyl 2-[(3-bromophenyl)carbonyl]-3-[(4-methoxyphenyl)amino]prop-2-enoate (P1-3) (3.00 g, 7.42 mmol) was added to a stirred at 200° C. $Ph_2O$ (50 mL). Resulted solution was stirred at 200-230° C. for 30 min, cooled to ambient temperature, and poured into hexane (200 mL). The resulted mixture was stirred for 30 min. Formed precipitate was filtered off and washed with hexane to afford 0.50 g (19%) of 3-[(3-bromophenyl)carbonyl]-6-methoxyquinolin-4(1H)-one (P1-4) as a brown solid.

A mixture of 3-[(3-bromophenyl)carbonyl]-6-methoxyquinolin-4(1H)-one (P1-4) (0.50 g, 1.40 mmol), 3,4-dimethylphenyl hydrazine hydrochloride (0.29 g, 1.68 mmol), AcOK (0.165 g, 1.68 mmol), and AcOH (10 mL) was stirred and heated under reflux for 7 h, and cooled to ambient temperature. Formed precipitate was filtered off and purified by re-crystallized with AcOH (10 mL) followed by washing with $Et_2O$ to afford 0.35 g (55%) of 3-(3-bromophenyl)-1-(3,4-dimethylphenyl)-8-methoxy-1H-pyrazolo[4,3-c]quinoline (P1) as a light brown solid. $^1H$ NMR (400 MHz, DMSO-$d_6$): 9.55 (s, 1H), 8.23-8.15 (m, 3H), 7.75-7.73 (m, 1H), 7.58-7.51 (m, 5H), 6.87 (s, 1H), 3.66 (s, 3H), 2.41 (s, 3H), 2.37 (s, 3H).

Preparation 2: 3-(4-bromo-3-chlorophenyl)-1-phenyl-1H-pyrazolo[4,3-c]quinoline (P40)

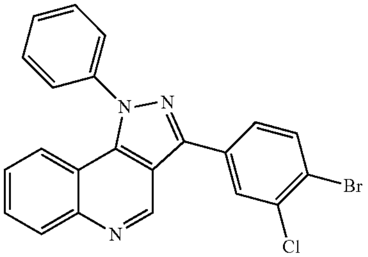 [SMILES: Clc1cc(-c2nn(-c3ccccc3)c3c2cnc2ccccc23)ccc1Br]

The compound was synthesized according to the procedure described in Preparation 1 using ethyl 3-(4-bromo-3-chlorophenyl)-3-oxopropanoate instead of ethyl 3-(3-bromophenyl)-3-oxopropanoate, aniline instead of p-anisidine, and phenylhydrazine hydrochloride instead of 3,4-dimethylphenylhydrazine hydrochloride. Product was analyzed by LCMS: [$MH^+$] 434, 435.

Preparation 3: 3-(4-bromo-3-chlorophenyl)-8-methoxy-1-phenyl-1H-pyrazolo[4,3-c]quinoline (P41)

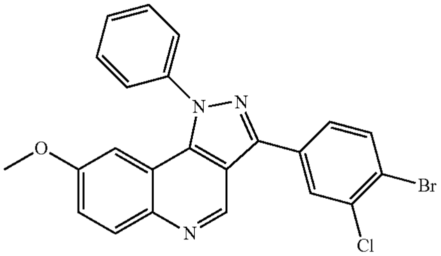 [SMILES: COc1ccc2ncc3c(-c4ccc(Br)c(Cl)c4)nn(-c4ccccc4)c3c2c1]

The compound was synthesized according to the procedure described in Preparation 1 using ethyl 3-(4-bromo-3-chlorophenyl)-3-oxopropanoate instead of ethyl 3-(3-bromophenyl)-3-oxopropanoate and phenylhydrazine hydrochloride instead of 3,4-dimethylphenylhydrazine hydrochloride. The product was analyzed by LCMS.

Preparation 4: 3-(4-bromo-3-chlorophenyl)-1-(3,4-dimethylphenyl)-1H-pyrazolo[4,3-c]quinoline (P42)

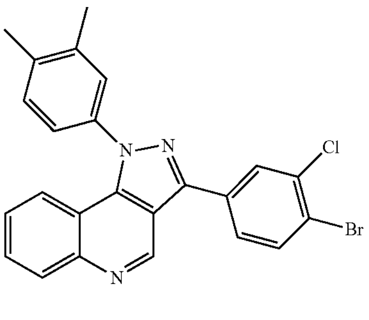 [SMILES: Cc1ccc(-n2nc(-c3ccc(Br)c(Cl)c3)c3cnc4ccccc4c32)cc1C]

The compound was synthesized according to the procedure described in Preparation 1 using ethyl 3-(4-bromo-3-chlorophenyl)-3-oxopropanoate instead of ethyl 3-(3-bromophenyl)-3-oxopropanoate and aniline instead of p-anisidine. The product was analyzed by LCMS.

Preparation 5: 3-(4-bromo-3-chlorophenyl)-1-(3,4-dimethylphenyl)-8-methoxy-1H-pyrazolo[4,3-c]quinoline (P43)

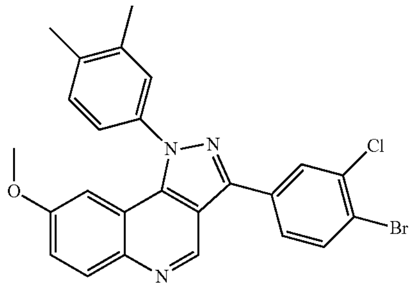 [SMILES: COc1ccc2ncc3c(-c4ccc(Br)c(Cl)c4)nn(-c4ccc(C)c(C)c4)c3c2c1]

The compound was synthesized according to the procedure described in Preparation 1 using ethyl 3-(4-bromo-3-chlorophenyl)-3-oxopropanoate instead of ethyl 3-(3-bromophenyl)-3-oxopropanoate and phenylhydrazine hydrochloride instead of 3,4-dimethylphenylhydrazine hydrochloride. The product was analyzed by LCMS.

Preparation 6: 3-(4-bromophenyl)-8-methoxy-1-phenyl-1H-pyrazolo[4,3-c]quinoline (P44)

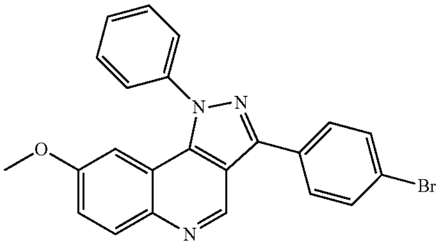 [SMILES: COc1ccc2ncc3c(-c4ccc(Br)cc4)nn(-c4ccccc4)c3c2c1]

The compound was synthesized according to the procedure described in Preparation 1 using ethyl 3-(4-bromophenyl)-3-oxopropanoate instead of ethyl 3-(3-bromophenyl)-3-oxopropanoate and phenylhydrazine hydrochloride instead of 3,4-dimethylphenylhydrazine hydrochloride. The product was analyzed by LCMS.

Preparation 7: 1-(3-bromophenyl)-8-methoxy-3-(3-methoxyphenyl)-1H-pyrazolo[4,3-c]quinoline (P2, 1.79)

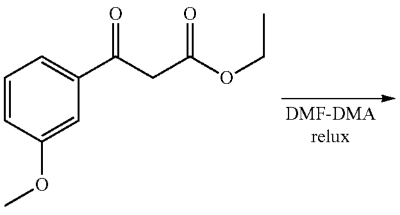

P2-1

-continued

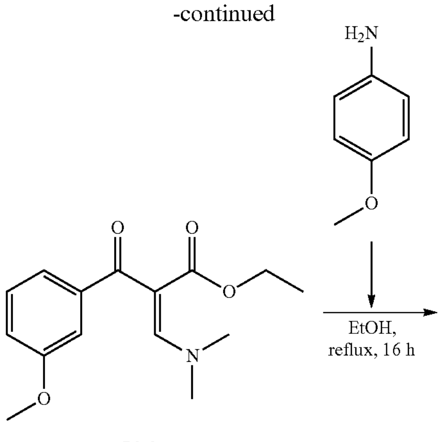

P2-2

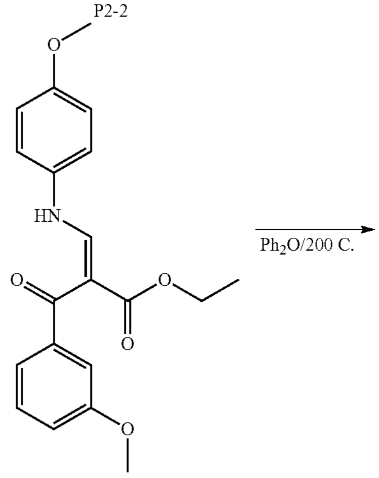

P2-3

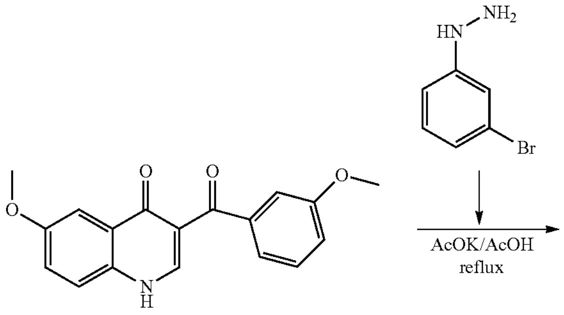

P2-4

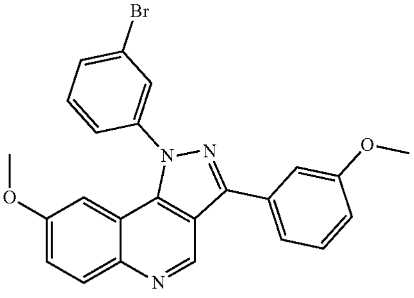

P2

A mixture of ethyl 3-(3-methoxyphenyl)-3-oxopropanoate (P2-1) (51 g, 230 mmol) and DMF-DMA (136 g, 1.14 mmol) was stirred and heated under reflux for 8 hours, then concentrated under reduced pressure to afford crude 62.0 g (97%) of ethyl 3-(dimethylamino)-2-[(3-methoxyphenyl) carbonyl]prop-2-enoate (P2-2) that was used for the next step without purification.

A mixture of ethyl 3-(dimethylamino)-2-[(3-methoxyphenyl)carbonyl]prop-2-enoate (P2-2) (15 g, 55 mmol), p-anisidine (8.1 g, 65 mmol), and anh. EtOH (100 mL) was stirred and heated under reflux overnight and then concentrated under reduced pressure. The residue was subjected to silica CC eluting with a mixture of hexane and EtOAc (10:1) to afford 14.0 g (73%) of ethyl (2E)-3-[(4-methoxyphenyl) amino]-2-[(3-methoxyphenyl)carbonyl]prop-2-enoate (P2-3) as a mixture Z- and E-isomers.

Ethyl (2E)-3-[(4-methoxyphenyl)amino]-2-[(3-methoxyphenyl)carbonyl]prop-2-enoate (P2-3) (14.0 g, 40 mmol) was added to a stirred at 200 C $Ph_2O$ (50 mL). Resulted solution was stirred at 200-230° C. for a 30 min, cooled to ambient temperature, and poured into hexane (200 mL). The resulted mixture was stirred for 30 min. Formed precipitate was filtered off and washed with hexane to afford 5.70 g (44%) of 6-methoxy-3-[(3-methoxyphenyl)carbonyl]quinolin-4(1H)-one (P2-4) as a brown solid.

A mixture of 6-methoxy-3-[(3-methoxyphenyl)carbonyl] quinolin-4(1H)-one (P2-4) (0.435 g, 1.43 mmol), 3-bromophenyl hydrazine hydrochloride (0.479 g, 2.15 mmol), AcOK (0.210 g, 2.15 mmol), and AcOH (10 mL) was stirred and heated under reflux for 7 h and cooled to ambient temperature. Formed precipitate was filtered off and purified by re-crystallized with AcOH (10 mL) followed by washing with $Et_2O$ to afford 0.20 g (31%) of the title compound P2 (1.79) as a light brown solid. $^1H$ NMR (400 MHz, DMSO-$d_6$): 9.42 (s, 1H), 8.14-8.12 (m, 2H), 7.93 (d, J=8.1 Hz, 1H), 7.87 (d, J=7.8 Hz, 1H), 7.72-7.67 (m, 2H), 7.57 (s, 1H), 7.52 (t, J=7.8 Hz, 1H), 7.43 (d, J=6.6 Hz, 1H), 7.10 (d, J=6.2 Hz, 1H), 6.88 (d, J=2.4 Hz, 1H), 3.88 (s, 3H), 3.60 (s, 3H).

Preparation 8: 1-(5-chloro-2-methylphenyl)-8-methoxy-3-(3-methoxyphenyl)-1H-pyrazolo[4,3-c] quinoline (P3, 1.6)

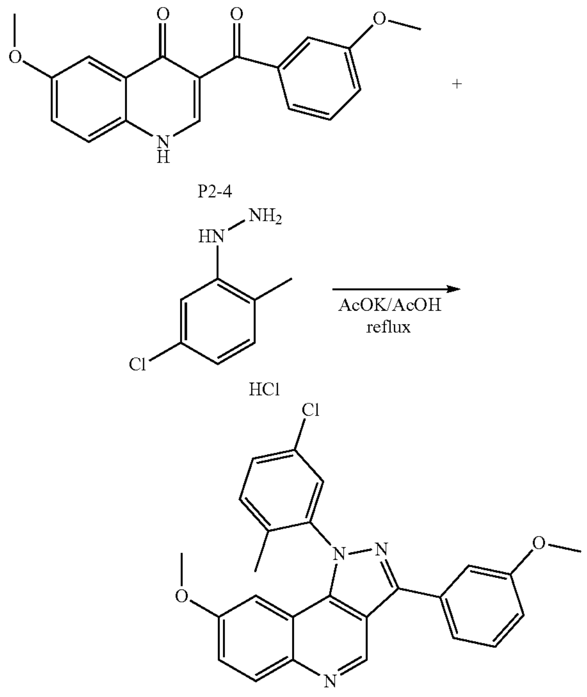

P2-4

HCl

P3

A mixture of 6-methoxy-3-[(3-methoxyphenyl)carbonyl] quinolin-4(1H)-one (P2-4) (0.30 g, 0.97 mmol), 3-chloro-6-methylphenyl hydrazine hydrochloride (0.243 g, 1.26 mmol), AcOK (0.165 g, 1.68 mmol), and AcOH (7 mL) was stirred and heated under reflux for 7 h and cooled to ambient temperature. Formed precipitate was filtered off and purified by re-crystallized from AcOH (10 mL) followed by washing with $Et_2O$ to afford 0.18 g (43%) of the title compound P3 (1.6) as a light brown solid. 1H NMR (400 MHz, DMSO-$d_6$): 9.45 (s, 1H), 8.13 (d, J=9.2 Hz, 1H), 7.91 (d, J=2.2 Hz, 1H), 7.76 (d, J=6.1 Hz, 1H), 7.71 (d, J=8.1 Hz, 1H), 7.67 (d, J=8.3 Hz, 1H), 7.59-7.58 (m, 1H), 7.52 (t, J=8.2 Hz, 1H), 7.43 (d, J=6.4 Hz, 1H), 7.10 (d, J=5.3 Hz, 1H), 6.55 (d, J=2.8 Hz, 1H), 3.88 (s, 3H), 3.53 (s, 3H), 1.96 (s, 3H).

Preparation 9: 1-(5-chloro-2-methylphenyl)-3-(3,4-dimethylphenyl)-8-methoxy-1H-pyrazolo[4,3-c] quinoline (P4, 1.9)

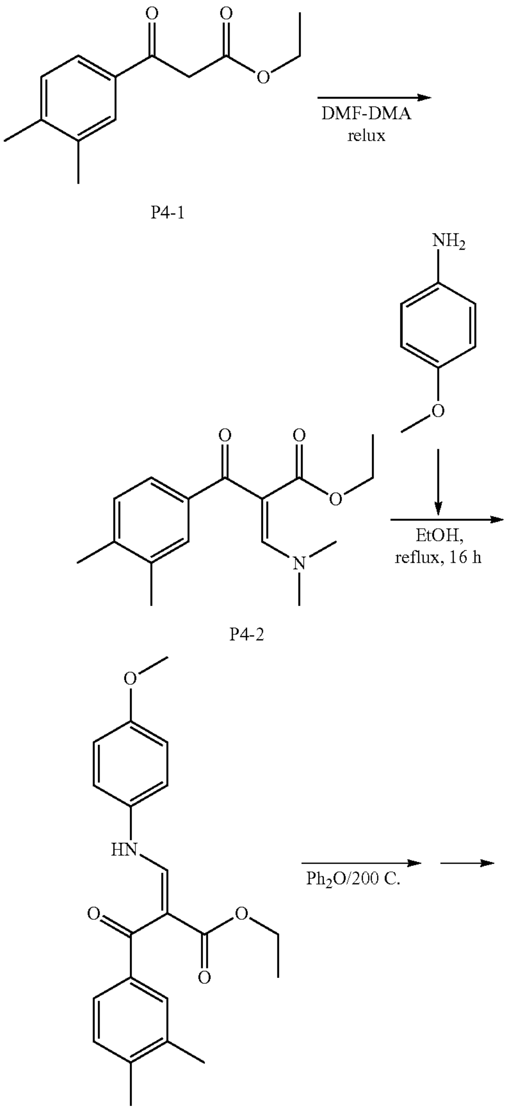

P4-1

P4-2

P4-3

-continued

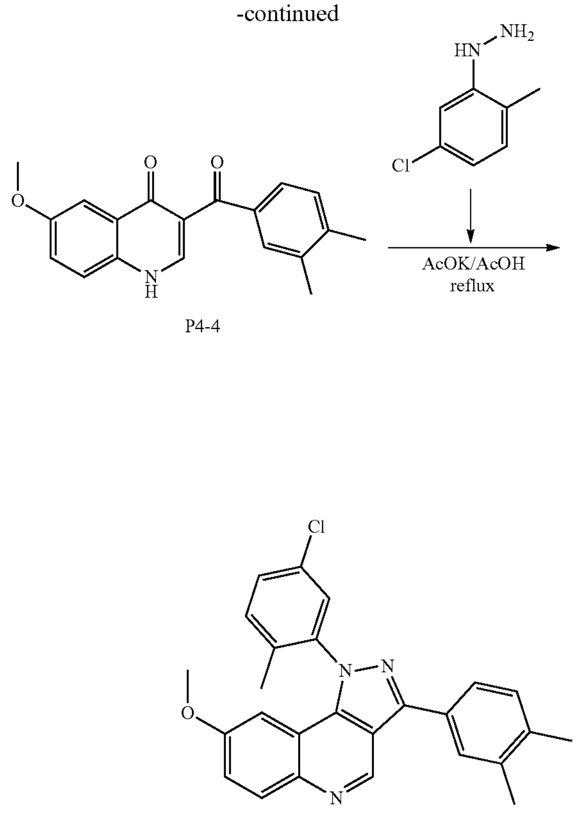

P4-4

P4

A mixture of ethyl 3-(3,4-dimethylphenyl)-3-oxopropanoate (P4-1) (12.1 g, 55 mmol) and DMF-DMA (33.0 g, 275 mmol) was stirred and heated under reflux for 8 hours, then concentrated under reduced pressure to afford 15.0 g, (99%) of ethyl 3-(dimethylamino)-2-[(3,4-dimethylphenyl) carbonyl]prop-2-enoate (P4-2) that was used for the next step without purification.

A mixture of ethyl 3-(dimethylamino)-2-[(3,4-dimethylphenyl)carbonyl]prop-2-enoate (P4-2) (15 g, 55 mmol), p-anisidine (8.1 g, 65 mmol), and anh. EtOH (100 mL) was stirred and heated under reflux overnight and then concentrated under reduced pressure. The residue was subjected to silica CC eluting with a mixture of hexane and EtOAc (10:1) to afford 14.0 g (73%) of ethyl 2-[(3,4-dimethylphenyl) carbonyl]-3-[(4-methoxyphenyl)amino]prop-2-enoate (P4-3) as a mixture Z- and E-isomers.

2-[(3,4-Dimethylphenyl)carbonyl]-3-[(4-methoxyphenyl) amino]prop-2-enoate (P4-3) (14.0 g, 40 mmol) was added to a stirred at 200° C. $Ph_2O$ (50 mL). Resulted solution was stirred at 200-230° C. for a 30 min, cooled to ambient temperature, and poured into hexane (200 mL). The resulted mixture was stirred for 30 min. Formed precipitate was filtered off and washed with hexane to afford 5.70 g (44%) of 3-[(3,4-dimethylphenyl)carbonyl]-6-methoxyquinolin-4 (1H)-one (P4-4) as a brown solid.

A mixture of 3-[(3,4-dimethylphenyl)carbonyl]-6-methoxyquinolin-4(1H)-one (P4-4) (0.500 g, 1.63 mmol), 3-chloro-6-methylphenyl hydrazine hydrochloride (0.470 g, 2.44 mmol), AcOK (0.24 g, 2.44 mmol), and AcOH (7 mL) was stirred and heated under reflux for 7 h and cooled to ambient temperature. Formed precipitate was filtered off and purified by re-crystallized from AcOH (10 mL) followed by washing with $Et_2O$ to afford 0.35 g (55%) of the title compound P4 as a light brown solid. The product was analyzed by LCMS.

Preparation 10: 1-(3-bromophenyl)-3-(3,4-dimethylphenyl)-8-methoxy-1H-pyrazolo[4,3-c]quinoline (P5, 1.12)

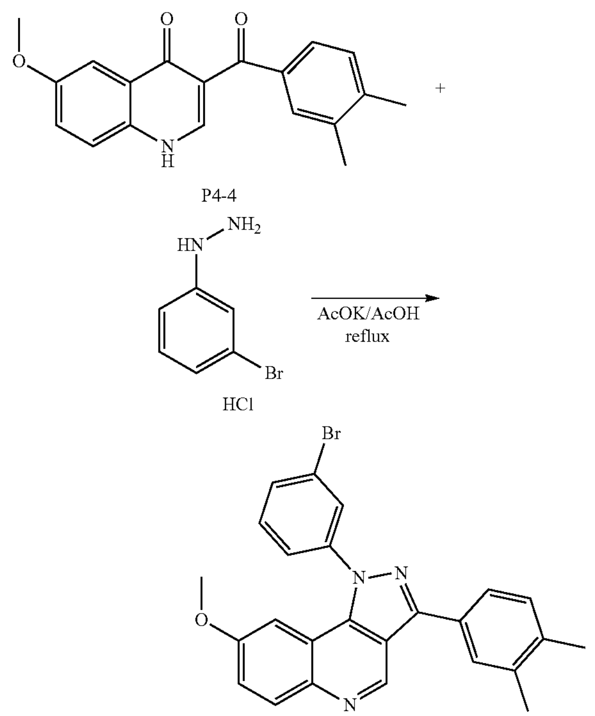

P4-4

HCl

P5

A mixture of 3-[(3,4-dimethylphenyl)carbonyl]-6-methoxyquinolin-4(1H)-one (P4-4) (0.50 g, 1.63 mmol), 3-bromophenyl hydrazine hydrochloride (0.546 g, 2.44 mmol), AcOK (0.24 g, 2.44 mmol), and AcOH (7 mL) was stirred and heated under reflux for 7 h and cooled to ambient temperature. Formed precipitate was filtered off and purified by re-crystallized from AcOH (10 mL) followed by washing with $Et_2O$ to afford 0.36 g (48%) of the title compound P5 as a light brown solid. $^1H$ NMR (400 MHz, DMSO-$d_6$): 9.45 (s, 1H), 8.14-8.12 (m, 2H), 7.93-7.81 (m, 4H), 7.71-7.68 (m, 1H), 7.45-7.43 (m, 1H), 7.35-7.34 (m, 1H), 6.88-6.87 (m, 1H), 3.59 (s, 3H), 2.35 (s, 3H), 2.31 (s, 3H).

Preparation 11: 3-(3-bromophenyl)-1-(2,3-dimethylphenyl)-8-methoxy-1H-pyrazolo[4,3-c]quinoline (P6)

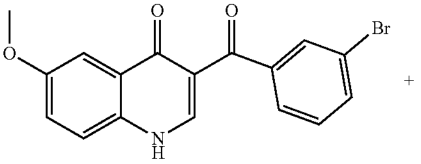

P1-4

-continued

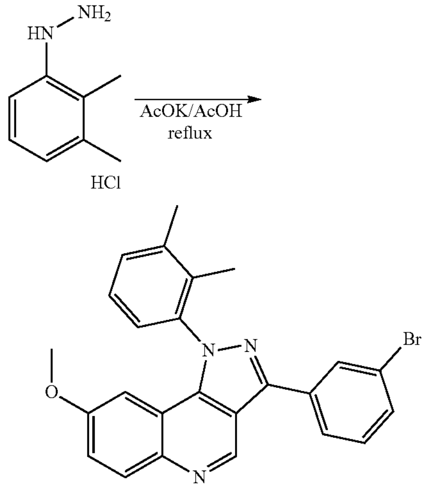

P6

To a mixture of compound 3-[(3-bromophenyl)carbonyl]-6-methoxyquinolin-4(1H)-one (P1-4) (0.420 g, 1.18 mmol) and 2,3-dimethylphenyl hydrazine hydrochloride (0.303 g, 1.76 mmol) in AcOH (10 ml) a AcOK (0.165 g, 1.76 mmol) was added, and mixture was stirred at 110° C. for a 7 h. Then mixture was cooled to rt and precipitate was filtered off A solid was recrystallized from AcOH (10 ml), filtered, washed with $Et_2O$ to give 0.200 g of crude product with 60% content of P6. The product was analyzed by LCMS.

Preparation 12: 3-(4-bromophenyl)-1-(3,4-dimethylphenyl)-8-methoxy-1H-pyrazolo[4,3-c]quinoline (P7)

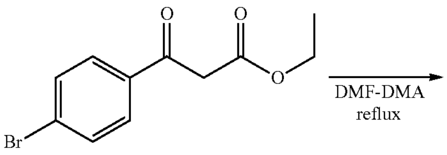

P7-1

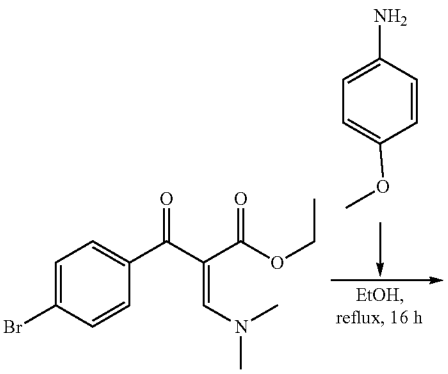

P7-2

-continued

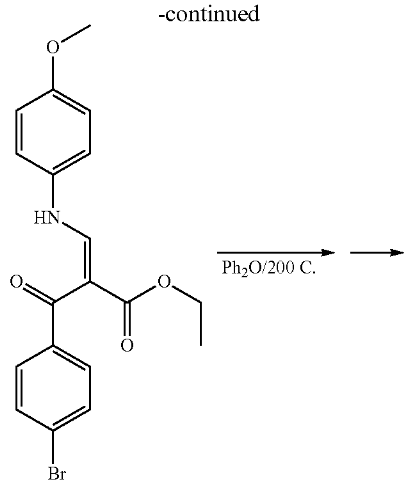

P7-3

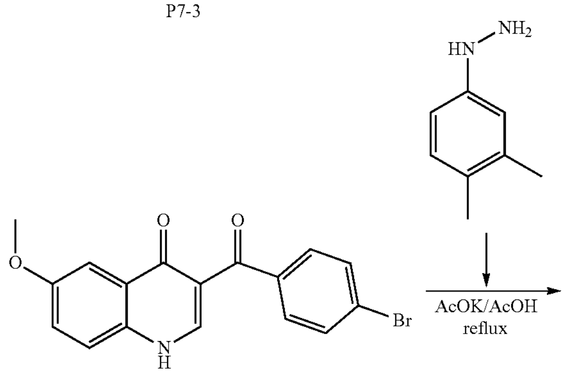

P7-4

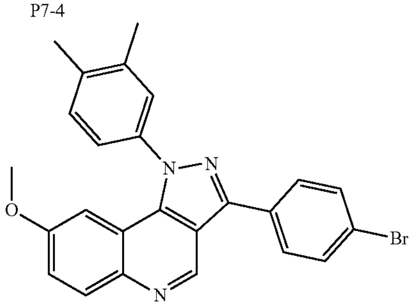

P7

A mixture of ethyl 3-(4-bromophenyl)-3-oxopropanoate (P7-1) (5.2 g, 19 mmol) and DMF-DMA (13.2 g, 110 mmol) was stirred and heated under reflux for 8 h, then concentrated under reduced pressure to afford 6.20 g, (99%) of ethyl 2-[(4-bromophenyl)carbonyl]-3-(dimethylamino)prop-2-enoate (P7-2) that was used in the next step without purification.

A mixture of ethyl 2-[(4-bromophenyl)carbonyl]-3-(dimethylamino)prop-2-enoate (P7-2) (3 g, 9 mmol), p-anisidine (1.35 g, 11 mmol), and anh. EtOH (100 mL) was stirred and heated under reflux overnight and then concentrated under reduced pressure. The residue was subjected to silica CC eluting with a mixture of hexane and EtOAc (10:1) to afford 3.1 g (83%) of ethyl 2-[(4-bromophenyl)carbonyl]-3-[(4-methoxyphenyl)amino]prop-2-enoate (P7-3) as a mixture of Z- and E-isomers.

Ethyl 2-[(4-bromophenyl)carbonyl]-3-[(4-methoxyphenyl)amino]prop-2-enoate (P7-3) (3.00 g, 7.42 mmol) was added to a stirred at 200° C. $Ph_2O$ (50 mL). Resulted solution was stirred at 200-230° C. for a 30 min, cooled to ambient temperature, and poured into hexane (200 mL). The resulted mixture was stirred for 30 min. Formed precipitate was filtered off and washed with hexane to afford 0.50 g (19%) of 3-[(4-bromophenyl)carbonyl]-6-methoxyquinolin-4(1H)-one (P7-4) as a brown solid.

A mixture of 3-[(4-bromophenyl)carbonyl]-6-methoxyquinolin-4(1H)-one (P7-4) (0.50 g, 1.40 mmol), 3,4-dimethylphenyl hydrazine hydrochloride (0.29 g, 1.68 mmol), AcOK (0.165 g, 1.68 mmol), and AcOH (10 mL) was stirred and heated under reflux for 7 h and cooled to ambient temperature. Formed precipitate was filtered off and purified by re-crystallized from AcOH (10 mL) followed by washing with $Et_2O$ to afford 0.35 g (55%) of the title compound P7 as a light brown solid. $^1H$ NMR (400 MHz, DMSO-$d_6$): 9.79 (s, 1H), 8.34 (d, J=8.0 Hz, 1H), 8.11 (d, J=8.0 Hz, 2H), 7.82 (d, J=8.0 Hz, 2H), 7.64-7.61 (m, 2H), 7.54 (s, 2H), 6.87 (s, 1H), 3.57 (s, 3H), 2.41 (s, 3H), 2.38 (s, 3H).

Preparation 13: 3-(4-bromophenyl)-1-(3,4-dimethylphenyl)-1H-pyrazolo[4,3-c]quinoline (P8)

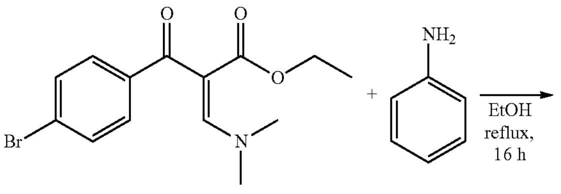

P7-2

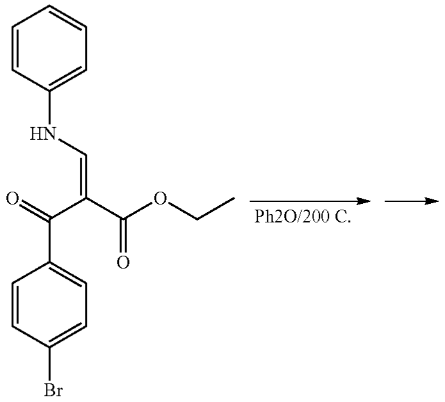

P8-1

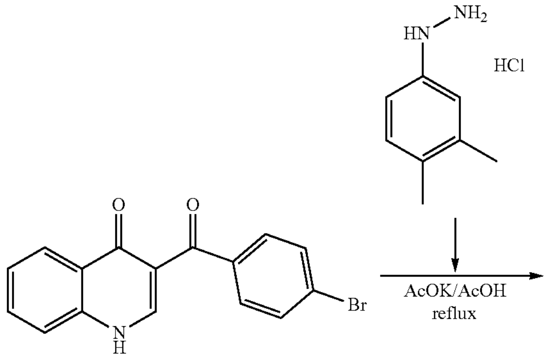

P8-2

-continued

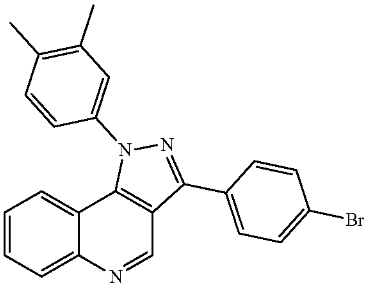

P8

A mixture of ethyl 3-(4-bromophenyl)-1-(3,4-dimethylphenyl)-1H-pyrazolo[4,3-c]quinoline (P7-2, see Preparation 12) (3 g, 9 mmol), aniline (1.04 g, 11 mmol), and anh. EtOH (100 mL) was stirred and heated under reflux overnight and then concentrated under reduced pressure. The residue was subjected to silica CC eluting with a mixture of hexane and EtOAc (10:1) to afford 2.0 g (58%) of ethyl 2-[(4-bromophenyl)carbonyl]-3-(phenylamino)prop-2-enoate (P8-1) as a mixture of Z- and E-isomers.

Ethyl 2-[(4-bromophenyl)carbonyl]-3-(phenylamino) prop-2-enoate (P8-1) (5.0 g, 13.3 mmol) was added to a stirred at 200° C. $Ph_2O$ (50 mL). Resulted solution was stirred at 200-230° C. for a 30 min, cooled to ambient temperature, and poured into hexane (200 mL). The resulted mixture was stirred for 30 min. Formed precipitate was filtered off and washed with hexane to afford 0.50 g (19%) of 3-[(4-bromophenyl)carbonyl]quinolin-4(1H)-one (P8-2) as a brown solid.

A mixture of 3-[(4-bromophenyl)carbonyl]quinolin-4 (1H)-one (P8-2) (1.6 g, 4.8 mmol), 3,4-dimethylphenyl hydrazine hydrochloride (0.73 g, 5.3 mmol), AcOK (0.165 g, 1.68 mmol), and AcOH (10 mL) was stirred and heated under reflux for 7 h and cooled to ambient temperature. Formed precipitate was filtered off and purified by re-crystallized from AcOH (10 mL) followed by washing with $Et_2O$ to afford 0.4 g (19%) of the title compound P8 as a light brown solid. $^1H$ NMR (400 MHz, DMSO-$d_6$): 9.63 (s, 1H), 8.20 (d, J=8 Hz, 1H), 8.09-8.07 (d, J=8 Hz, 2H), 7.80-7.75 (m, 3H), 7.56-7.49 (m, 3H), 7.47 (s, 2H), 2.41 (s, 3H), 2.36 (s, 3H).

Preparation 14: 3-(4-bromophenyl)-1-phenyl-1H-pyrazolo[4,3-c]quinoline (P9)

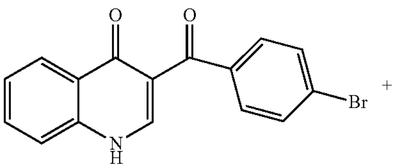

P8-2

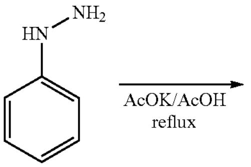

-continued

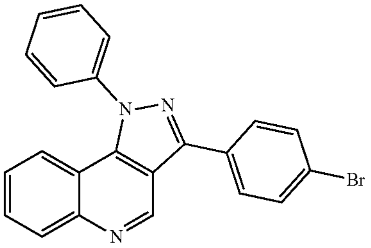

P9

A mixture of 3-[(4-bromophenyl)carbonyl]quinolin-4(1H)-one (P8-2, see Preparation 13) (0.55 g, 1.17 mmol), phenyl hydrazine hydrochloride (0.36 g, 2.5 mmol), AcOK (0.165 g, 1.68 mmol), and AcOH (10 mL) was stirred and heated under reflux for 7 h, and cooled to ambient temperature. Formed precipitate was filtered off and purified by re-crystallized from AcOH (10 mL) followed by washing with $Et_2O$ to afford 0.30 g (45%) of the title compound P9 as a light brown solid. $^1H$ NMR (400 MHz, DMSO-$d_6$): 9.59 (s, 1H), 8.21 (d, J=8.0 Hz, 1H), 8.1 (d, J=8.0 Hz, 2H), 7.82-7.75 (m, 8H), 7.50-7.49 (m, 2H).

Preparation 15: 4-[1-(3,4-dimethylphenyl)-8-methoxy-1H-pyrazolo[4,3-c]quinolin-3-yl]-2-methoxyphenol (P10)

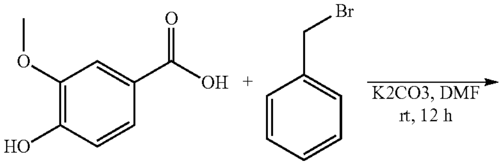

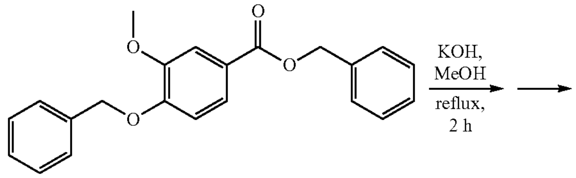

P10-1

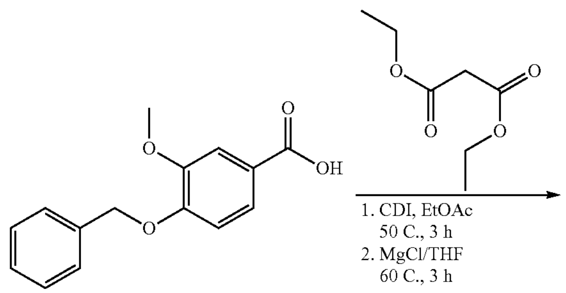

P10-2

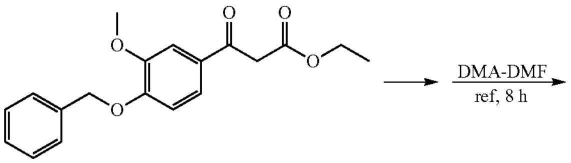

P10-3

-continued

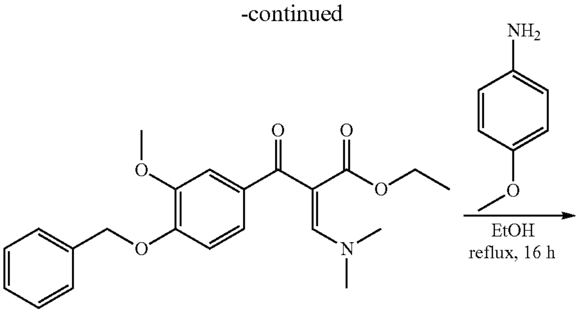

P10-4

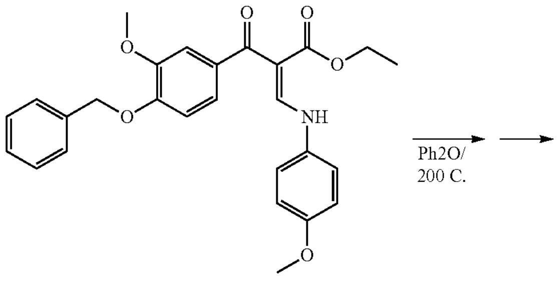

P10-5

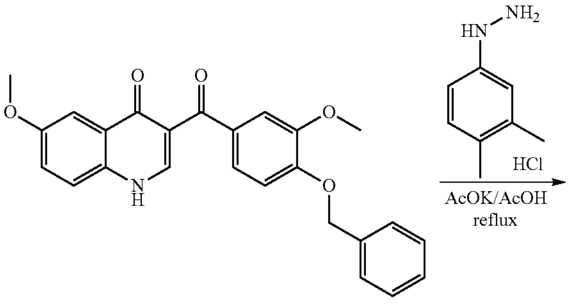

P10-6

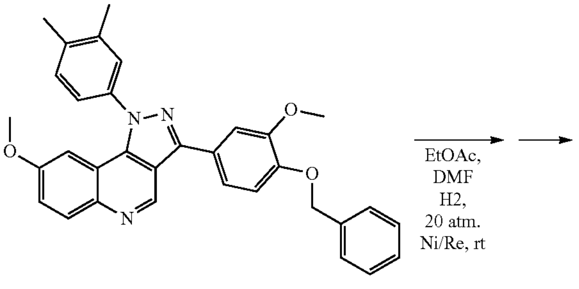

P10-7

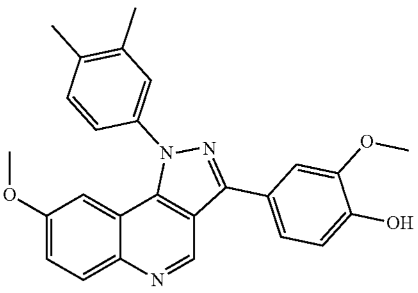

P10

A mixture of 4-hydroxy-3-methoxybenzoic acid (13.25 g, 78 mmol), benzyl bromide (33.7 g, 197 mmol), $K_2CO_3$ (38.1 g, 276 mmol), and DMF (75 mL) was stirred at ambient temperature for 12 h, filtered through Celite pad, and the filtrate was concentrated under reduced pressure. The residue was treated with water (200 mL), the formed precipitate was filtered off and dried by lyophilization to afford 27.2 g (99%) of benzyl 4-(benzyloxy)-3-methoxybenzoate (P10-1) that was used in the next step without further purification. $^1$H NMR (400 MHz, DMSO-$d_6$): 7.60 (d, J=9.2 Hz, 1H), 7.49 (s, 2H), 7.46-7.44 (m, 4H), 7.42-7.38 (m, 4H), 7.36-7.32 (m, 2H), 7.17 (d, J=8.4 Hz, 1H), 5.33 (s, 2H), 5.18 (s, 2H), 3.82 (s, 3H).

A mixture of benzyl 4-(benzyloxy)-3-methoxybenzoate (P10-1) (27.2 g, 78 mmol), KOH (6.5 g, 117 mmol), MeOH (200 mL), and water (15 mL) was stirred and heated under reflux for 2 h, concentrated under reduced pressure to ⅔ of initial volume, and acidified to pH=1-2. The formed precipitate was filtered off, washed with water, and dried by lyophilization to afford a 4-(benzyloxy)-3-methoxybenzoic acid (P10-2, 17.5 g, 88% yield) as a white solid. $^1$H NMR (400 MHz, DMSO-$d_6$): 12.60 (s, 1H), 7.55 (d, J=8.0 Hz, 1H), 7.47-7.45 (m, 3H), 7.42-7.38 (m, 2H), 7.36-7.32 (m, 1H), 7.14 (d, J=8.4 Hz, 1H), 5.16 (s, 2H), 3.81 (s, 3H).

A mixture of 4-(benzyloxy)-3-methoxybenzoic acid (P10-2, 17.5 g, 68 mmol), CDI (12.1 g, 75 mmol), and ethyl acetate (200 mL) was stirring at 50° C. for 3 h to form a solution of imidazolide. A mixture of $MgCl_2$ (25.8 g, 271 mmol), potassium salt of ethyl malonate (23.0 g, 136 mmol), and THF (200 mL) was stirred at 60° C. for 3 h, and then the solution of imidazolide was added. Obtained mixture was stirred and heated under reflux overnight, cooled, and treated with 10% aq. solution of HCl to dissolve formed precipitate. The organic layer was separated, the aqueous one was extracted twice with ethyl acetate. Combined organic layers were dried over $Na_2SO_4$ and concentrated under reduced pressure. The residue was subjected to silica CC eluting with a mixture of hexane and EtOAc (10:1) to afford 14.7 g, (66%) of ethyl 3-[4-(benzyloxy)-3-methoxyphenyl]-3-oxopropanoate (P10-3). $^1$H NMR (400 MHz, DMSO-$d_6$): 7.59 (d, J=8.0 Hz, 1H), 7.47-7.45 (m, 3H), 7.42-7.38 (m, 2H), 7.36-7.32 (m, 1H), 7.17 (d, J=8.4 Hz, 1H), 5.2 (s, 2H), 4.14-4.08 (m, 4H), 3.83 (s, 3H). 1.2-1.6 (t, 3H).

A mixture of ethyl 3-[4-(benzyloxy)-3-methoxyphenyl]-3-oxopropanoate (P10-3) (14.7 g, 45 mmol) and DMF-DMA (58.0 g, 675 mmol) was stirred and heated under reflux for 8 h, then concentrated under reduced pressure to afford 17.25 g (99%) of ethyl (2Z)-2-{[4-(benzyloxy)-3-methoxyphenyl]carbonyl}-3-(dimethylamino)prop-2-enoate (P10-4) that was used for the next step without purification.

A mixture of ethyl 2-{[4-(benzyloxy)-3-methoxyphenyl]carbonyl}-3-(dimethylamino)prop-2-enoate (P10-4) (16.13 g, 58 mmol) and p-anisidine (8.61 g, 70 mmol), and anh. EtOH (100 mL) was stirred and heated under reflux overnight and then concentrated under reduced pressure. The residue was subjected to silica CC eluting with a mixture of hexane and EtOAc (10:1) to afford 14.8 g (72%) of ethyl (2Z)-2-{[4-(benzyloxy)-3-methoxyphenyl]carbonyl}-3-[(4-methoxyphenyl)amino]prop-2-enoate (P10-5) as a mixture Z- and E-isomers.

Ethyl 2-{[4-(benzyloxy)-3-methoxyphenyl]carbonyl}-3-[(4-methoxyphenyl)amino]prop-2-enoate (P10-5, 7.00 g, 15.16 mmol) was added to a stirred at 200° C. $Ph_2O$ (100 mL). Resulted solution was stirred at 200-230° C. for 30 min, cooled to ambient temperature, and poured into hexane (200 mL). The resulted mixture was stirred for 30 min. Formed precipitate was filtered off and washed with hexane to afford 2.50 g (40%) of 3-{[4-(benzyloxy)-3-methoxyphenyl]carbonyl}-6-methoxyquinolin-4(1H)-one (P10-6).

A mixture of 3-{[4-(benzyloxy)-3-methoxyphenyl]carbonyl}-6-methoxyquinolin-4(1H)-one (P10-6, 1.65 g, 3.98 mmol), 3,4-dimethylphenyl hydrazine hydrochloride (0.82 g, 4.77 mmol), AcOK (0.48 g, 4.77 mmol), and AcOH (30 mL) was stirred and heated under reflux for 7 h and cooled to ambient temperature. Formed precipitate was filtered off and purified by re-crystallized from AcOH followed by washing with $Et_2O$ to afford 1.10 g (53%) of 3-[4-(benzyloxy)-3-methoxyphenyl]-1-(3,4-dimethylphenyl)-8-methoxy-H-pyrazolo[4,3-c]quinoline (P10-7). $^1$H NMR (400 MHz, DMSO-$d_6$): 9.41 (s, 1H), 8.09 (d, J=9.0 Hz, 1H), 7.64 (dd, J1=8.3 Hz, J2=1.5 Hz, 1H), 7.59 (d, J=1.5 Hz, 1H), 7.55 (s, 1H), 7.51-7.38 (m, 8H), 7.24 (d, J=8.2 Hz, 1H), 6.86-6.85 (m, 1H), 5.19 (s, 2H), 3.90 (s, 3H), 3.53 (s, 3H), 2.40 (s, 3H), 2.36 (s, 3H).

To a mixture of 3-[4-(benzyloxy)-3-methoxyphenyl]-1-(3,4-dimethylphenyl)-8-methoxy-1H-pyrazolo[4,3-c]quinoline (P10-7, 1.00 g, 1.93 mmol), EtOAc (20 mL), DMF (4 mL), and Ni/Re (300 mg) was hydrogenated at ambient temperature at 20 atm for a 16 h, filtered through Celite pad, and the filtrate was concentrated under reduced pressure. The residue was purified by re-crystallization from acetone to afford 0.51 g (62%) of 4-[1-(3,4-dimethylphenyl)-8-methoxy-1H-pyrazolo[4,3-c]quinolin-3-yl]-2-methoxyphenol (P10) as a slight yellow solid. $^1$H NMR (400 MHz, DMSO-$d_6$): 9.73 (br., 1H), 9.41 (s, 1H), 8.00 (br., 1H), 7.51-7.36 (m, 6H), 6.99-6.90 (m, 2H), 3.87 (s, 3H), 3.50 (s, 3H), 2.37 (s, 3H), 2.34 (s, 3H).

Preparation 16: 5-[1-(3,4-dimethylphenyl)-8-methoxy-1H-pyrazolo[4,3-c]quinolin-3-yl]-2-methoxyphenol (P27)

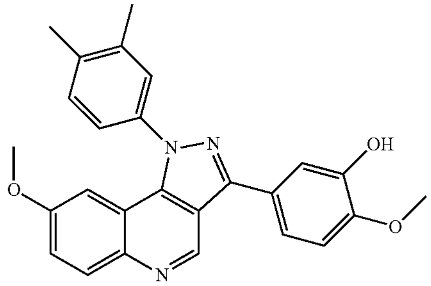 [SMILES: COc1ccc2ncc3c(-c4ccc(OC)c(O)c4)nn(-c4ccc(C)c(C)c4)c3c2c1]

The compound was synthesized according to the procedure described in Preparation 15 using 3-hydroxy-4-methoxybenzoic acid instead of 4-hydroxy-3-methoxybenzoic acid. The product was analyzed by LCMS.

Preparation 17: 4-[1-(3,4-dimethylphenyl)-1H-pyrazolo[4,3-c]quinolin-3-yl]-2-methoxyphenol (P28)

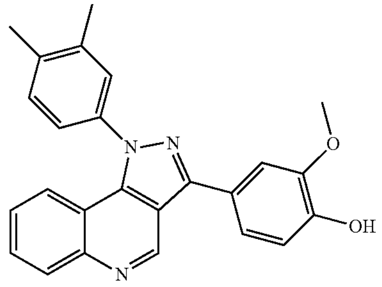 [SMILES: COc1cc(-c2nn(-c3ccc(C)c(C)c3)c3c2cnc2ccccc23)ccc1O]

The compound was synthesized according to the procedure described in Preparation 15 using aniline instead of p-anisidine. The product was analyzed by LCMS.

Preparation 18: 5-[1-(3,4-dimethylphenyl)-1H-pyrazolo[4,3-c]quinolin-3-yl]-2-methoxyphenol (P29)

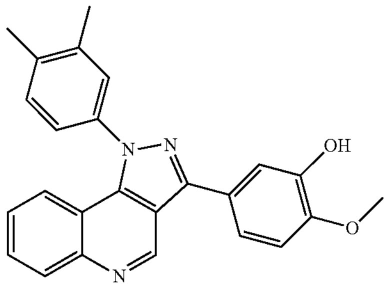

The compound was synthesized according to the procedure described in Preparation 15 using 3-hydroxy-4-methoxybenzoic acid instead of 4-hydroxy-3-methoxybenzoic acid and aniline instead of p-anisidine. The product was analyzed by LCMS.

Preparation 19: 2-methoxy-4-(1-phenyl-1H-pyrazolo[4,3-c]quinolin-3-yl)phenol (P30)

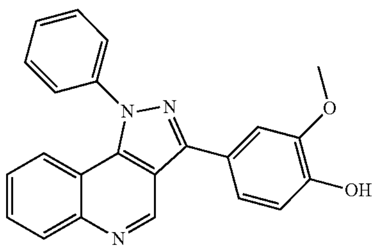 [SMILES: COc1cc(-c2nn(-c3ccccc3)c3c2cnc2ccccc23)ccc1O]

The compound was synthesized according to the procedure described in Preparation 15 using phenylhydrazine instead of 3,4-dimethylphenylhydrazine and aniline instead of p-anisidine. The product was analyzed by LCMS.

Preparation 20: 2-methoxy-4-(8-methoxy-1-phenyl-1H-pyrazolo[4,3-c]quinolin-3-yl)phenol (P31)

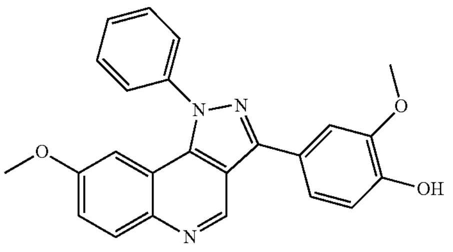 [SMILES: COc1ccc2ncc3c(-c4ccc(O)c(OC)c4)nn(-c4ccccc4)c3c2c1]

The compound was synthesized according to the procedure described in Preparation 15 using phenylhydrazine instead of 3,4-dimethylphenylhydrazine. The product was analyzed by LCMS.

Preparation 21: 2-methoxy-5-(1-phenyl-1H-pyrazolo[4,3-c]quinolin-3-yl)phenol (P32)

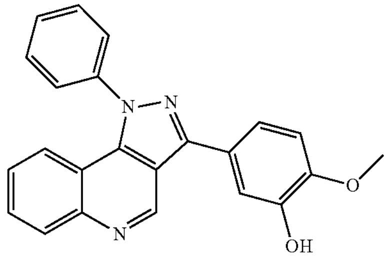 [SMILES: COc1ccc(-c2nn(-c3ccccc3)c3c2cnc2ccccc23)cc1O]

The compound was synthesized according to the procedure described in Preparation 15 using phenylhydrazine instead of 3,4-dimethylphenylhydrazine, aniline instead of p-anisidine, and 3-hydroxy-4-methoxybenzoic acid instead of 4-hydroxy-3-methoxybenzoic acid. The product was analyzed by LCMS.

Preparation 22: 2-methoxy-5-(8-methoxy-1-phenyl-1H-pyrazolo[4,3-c]quinolin-3-yl)phenol (P33)

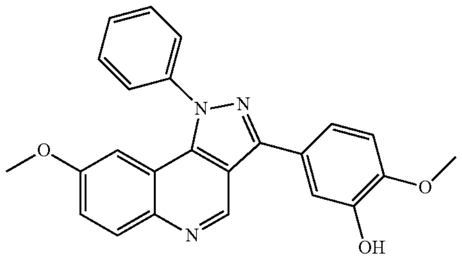

The compound was synthesized according to the procedure described in Preparation 15 using phenylhydrazine instead of 3,4-dimethylphenylhydrazine and 3-hydroxy-4-methoxybenzoic acid instead of 4-hydroxy-3-methoxybenzoic acid. The product was analyzed by LCMS.

Preparation 23: 4-[1-(3,4-dimethylphenyl)-8-methyl-1H-pyrazolo[4,3-c]quinolin-3-yl]-2-methoxyphenol (P34)

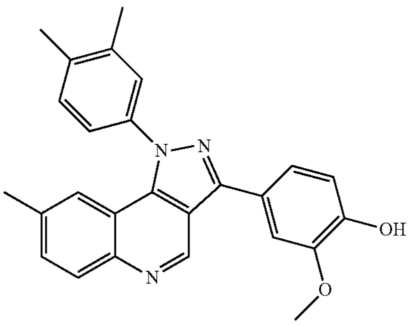 [SMILES: COc1cc(-c2nn(-c3ccc(C)c(C)c3)c3c2cnc2ccc(C)cc23)ccc1O]

The compound was synthesized according to the procedure described in Preparation 15 using p-toluidine instead of p-anisidine. The product was analyzed by LCMS.

Preparation 24: 4-[1-(2,4-dimethylphenyl)-8-methyl-1H-pyrazolo[4,3-c]quinolin-3-yl]-2-methoxyphenol (P35)

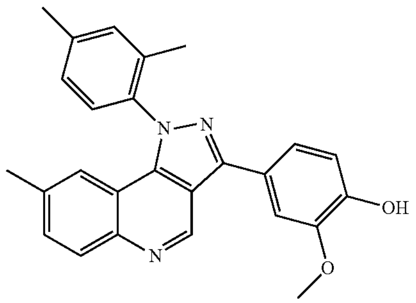 [SMILES: COc1cc(-c2nn(-c3ccc(C)cc3C)c3c2cnc2ccc(C)cc23)ccc1O]

The compound was synthesized according to the procedure described in Preparation 15 using p-toluidine instead of p-anisidine and 2,4-dimethylphenylhydrazine instead of 3,4-dimethylphenylhydrazine. The product was analyzed by LCMS.

Preparation 25: 4-[1-(2,3-dimethylphenyl)-8-methyl-1H-pyrazolo[4,3-c]quinolin-3-yl]-2-methoxyphenol (P36)

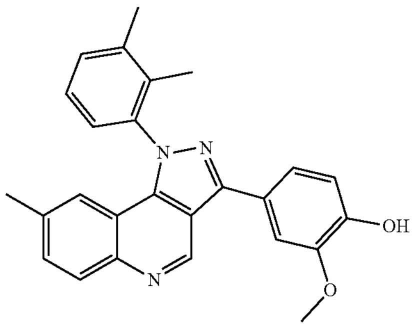 [SMILES: COc1cc(-c2nn(-c3cccc(C)c3C)c3c2cnc2ccc(C)cc23)ccc1O]

The compound was synthesized according to the procedure described in Preparation 15 using p-toluidine instead of p-anisidine and 2,3-dimethylphenylhydrazine instead of 3,4-dimethylphenylhydrazine. The product was analyzed by LCMS.

Preparation 26: 4-[1-(2,5-dimethylphenyl)-8-methyl-1H-pyrazolo[4,3-c]quinolin-3-yl]-2-methoxyphenol (P37)

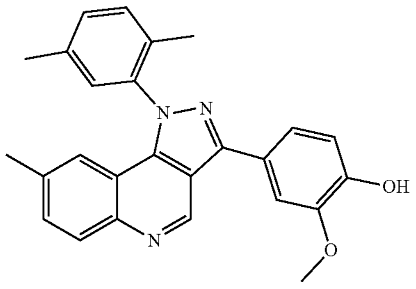 [SMILES: COc1cc(-c2nn(-c3cc(C)ccc3C)c3c2cnc2ccc(C)cc23)ccc1O]

The compound was synthesized according to the procedure described in Preparation 15 using p-toluidine instead of p-anisidine and 2,5-dimethylphenylhydrazine instead of 3,4-dimethylphenylhydrazine. The product was analyzed by LCMS.

Preparation 27: 4-[1-(3-chloro-2-methylphenyl)-8-methyl-1H-pyrazolo[4,3-c]quinolin-3-yl]-2-methoxyphenol (P38)

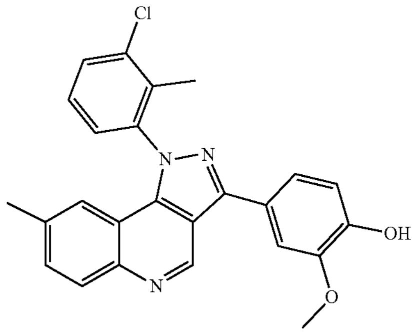 [SMILES: COc1cc(-c2nn(-c3cccc(Cl)c3C)c3c2cnc2ccc(C)cc23)ccc1O]

The compound was synthesized according to the procedure described in Preparation 15 using p-toluidine instead of p-anisidine and 3-chloro-2-methylphenylhydrazine instead of 3,4-dimethylphenylhydrazine. The product was analyzed by LCMS.

Preparation 28: 4-[1-(3,4-dimethylphenyl)-8-(trifluoromethoxy)-1H-pyrazolo[4,3-c]quinolin-3-yl]-2-methoxyphenol (P39)

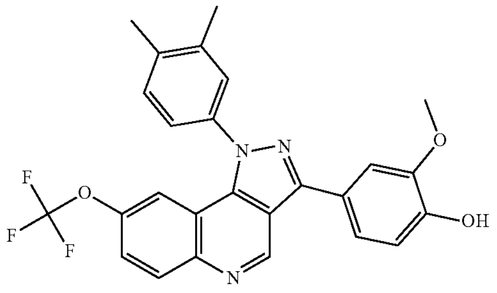 [SMILES: COc1cc(-c2nn(-c3ccc(C)c(C)c3)c3c2cnc2ccc(OC(F)(F)F)cc23)ccc1O]

The compound was synthesized according to the procedure described in Preparation 15 using p-trifluoromethoxyaniline instead of p-anisidine. The product was analyzed by LCMS.

Preparation 29: 3-(1,3-benzodioxol-5-ylcarbonyl) quinolin-4(1H)-one (P11)

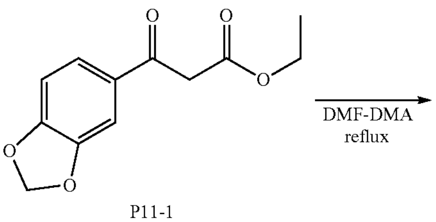

P11-1

-continued

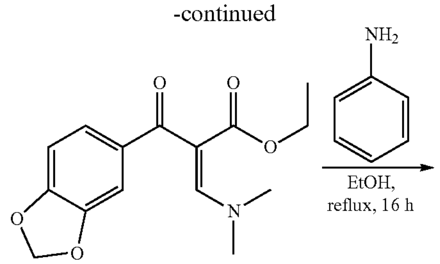

P11-2

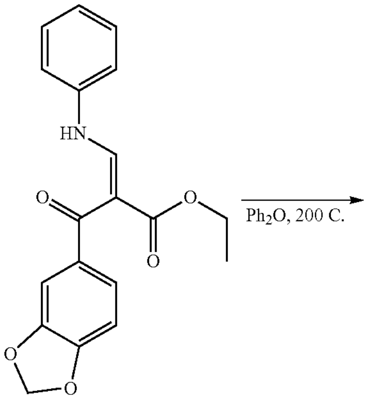

P11-3

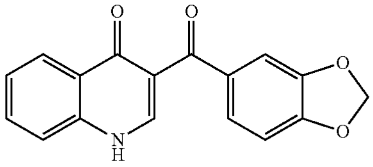

P11

A mixture of ethyl 3-(1,3-benzodioxol-5-yl)-3-oxopropanoate (P11-1) (10 g, 42.3 mmol) and DMF-DMA (27.2 g, 228 mmol) was heated under reflux for 8 h and concentrated under reduced pressure to afford 12.32 g, (97%) of ethyl 2-(1,3-benzodioxol-5-ylcarbonyl)-3-(dimethylamino)prop-2-enoate (P11-2) that was used in next step without further purification.

A mixture of ethyl 2-(1,3-benzodioxol-5-ylcarbonyl)-3-(dimethylamino)prop-2-enoate (P11-2) (10.0 g, 34.3 mmol), aniline (3.50 g, 37.8 mmol), and anh. EtOH (100 mL) was stirred and heated under reflux overnight and then concentrated under reduced pressure. The residue was subjected to silica CC eluting with a mixture of hexane and EtOAc (10:1) to afford 8.15 g (70%) of ethyl 2-(1,3-benzodioxol-5-ylcarbonyl)-3-(phenylamino)prop-2-enoate (P11-3) as a mixture Z- and E-isomers.

Ethyl 2-(1,3-benzodioxol-5-ylcarbonyl)-3-(phenylamino) prop-2-enoate (5.0 g, 14.8 mmol) was added to a stirred at 200° C. $Ph_2O$ (50 mL). Resulted solution was stirred at 200-230° C. for a 30 min, cooled to ambient temperature, and poured into hexane (100 mL). The resulted mixture was stirred for 30 min. Formed precipitate was filtered off and washed with hexane to afford 1.64 g (38%) of 3-(1,3-benzodioxol-5-ylcarbonyl)quinolin-4(1H)-one (P11).

Preparation 30: 3-(1,3-benzodioxol-5-ylcarbonyl)-6-methoxyquinolin-4(1H)-one (P12)

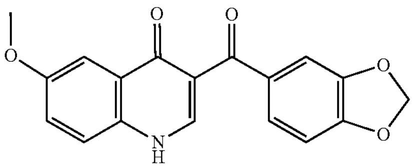 [SMILES: COc1ccc2[nH]cc(C(=O)c3ccc4c(c3)OCO4)c(=O)c2c1]

The compound was synthesized according to the procedure described in Preparation 29 using 4-methoxyaniline instead of aniline. The product was analyzed by LCMS.

Preparation 31: 4-chloroquinoline-3-carbaldehyde (P13)

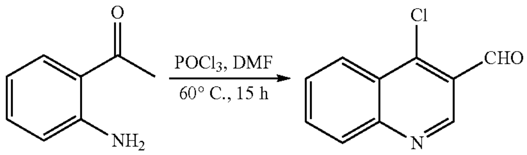

P13

The Vilsmeier reagent was prepared first by adding dropwise of $POCl_3$ (23 mL, 246 mmol) to stirred in inert atmosphere DMF (50 mL) maintaining temperature −5-0° C. followed by stirring of the mixture for 30 min at ambient temperature. Then 1-(2-aminophenyl)ethanone (5.0 mL, 41 mmol) was added dropwise to the stirred mixture within 30 min. The reaction mixture was stirred and heated at 60° C. for 16 h, cooled to ambient temperature, and poured into a vigorously stirred mixture of crashed ice (400 g) and water (200 mL) and neutralized to pH 6-7 by addition portion wise of $NaHCO_3$. The precipitate was filtered off, dissolved in $CHCl_3$, washed with water, dried over $Na_2SO_4$, filtered, and concentrated under reduced pressure, The residue was purified by re-crystallization with a mixture of EtOAc and heptane (1:2) to afford 4.45 g (57%) of 4-chloroquinoline-3-carbaldehyde (P13). $^1H$ NMR (400 MHz, DMSO-$d_6$): δ 10.55 (s, 1H), 9.14 (s, 1H), 8.41 (m, 1H), 8.16 (m, 1H), 8.04 (m, 1H), 7.88 (m, 1H).

Preparation 32: 4-chloro-6-methoxyquinoline-3-carbaldehyde (P14)

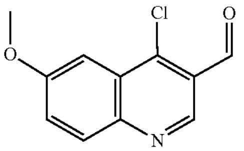

The compound was synthesized according to the procedure described in Preparation 31 using 1-(2-amino-5-methoxyphenyl)ethanone instead of 1-(2-aminophenyl)ethanone. $^1H$ NMR (400 MHz, DMSO-$d_6$): δ 10.55 (s, 1H), 8.99 (s, 1H), 8.08 (d, J=9.2 Hz, 1H), 7.67 (m, 1H), 7.60 (m, 1H), 4.00 (s, 3H).

Preparation 33:
4-chloro-8-methoxyquinoline-3-carbaldehyde (P15)

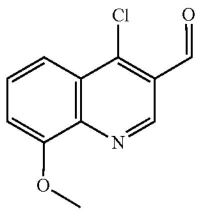

The compound was synthesized according to the procedure described in Preparation 31 using 1-(2-amino-3-methoxyphenyl)ethanone instead of 1-(2-aminophenyl)ethanone. $^1H$ NMR (400 MHz, DMSO-$d_6$): δ 10.55 (s, 1H), 9.06 (s, 1H), 7.92 (d, J=8.2 Hz, 1H), 7.79 (t, J=8.2 Hz, 1H), 7.49 (d, J=8.2 Hz, 1H), 4.01 (s, 3H).

Preparation 34: 4-chloro-6-(trifluoromethoxy)quinoline-3-carbaldehyde (P16)

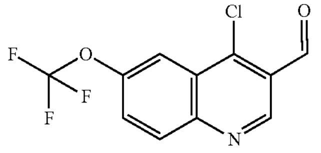 [SMILES: O=Cc1cnc2ccc(OC(F)(F)F)cc2c1Cl]

The compound was synthesized according to the procedure described in Preparation 31 using 1-[2-amino-5-(trifluoromethoxy)phenyl]ethanone instead of 1-(2-aminophenyl)ethanone.

Preparation 35: 1H-pyrazolo[4,3-c]quinoline (P17)

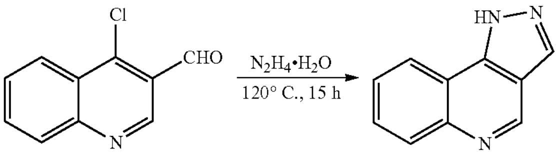

P13 P17

A mixture of 4-chloroquinoline-3-carbaldehyde (P13, 4.0 g, 21 mmol) and hydrazine hydrate (40 mL) was stirred and heated at 120° C. for 15 h, cooled to ambient temperature, and poured into stirred cold water (250 mL). The formed precipitate was filtered off, washed with water, ether, and dried at 60° C. to afford 3.41 g (96%) of 1H-pyrazolo[4,3-c]quinoline (P17). $^1H$ NMR (400 MHz, DMSO-$d_6$): δ 14.33 (s, 1H), 9.24 (s, 1H), 8.42 (m, 2H), 8.12 (d, J=7.6 Hz, 1H), 7.74 (m, 2H).

Preparation 36:
8-methoxy-1H-pyrazolo[4,3-c]quinoline (P18)

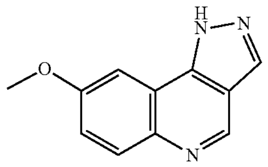

The compound was synthesized according to the procedure described in Preparation 35 using 4-chloro-6-methoxyquinoline-3-carbaldehyde instead of 4-chloroquinoline-3-carbaldehyde, $^1H$ NMR (400 MHz, DMSO-$d_6$): δ 14.11 (s, 1H), 9.08 (s, 1H), 8.36 (s, 1H), 8.03 (d, J=9.2 Hz, 1H), 7.88 (d, J=2.8 Hz, 1H), 7.38 (dd, $J_1$=9.2 Hz, $J_2$=2.8 Hz, 1H), 3.95 (s, 3H).

Preparation 37:
6-methoxy-1H-pyrazolo[4,3-c]quinoline (P19)

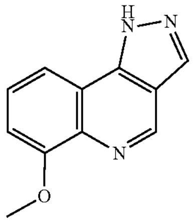

The compound was synthesized according to the procedure described in Preparation 35 using 4-chloro-8-methoxyquinoline-3-carbaldehyde instead of 4-chloroquinoline-3-carbaldehyde. $^1H$ NMR (400 MHz, DMSO-$d_6$): δ 14.25 (brs, 1H), 9.17 (s, 1H), 8.39 (s, 1H), 7.96 (d, J=8.0 Hz, 1H), 7.63 (t, J=8.0 Hz, 1H), 7.26 (d, J=8.0 Hz, 1H), 3.98 (s, 3H).

Preparation 38: 3-iodo-1H-pyrazolo[4,3-c]quinoline (P20)

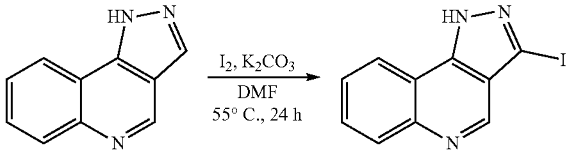

P17 P20

To a stirred mixture of 1H-pyrazolo[4,3-c]quinoline (P17, see Preparation 35) (3.40 g, 20 mmol) and $K_2CO_3$ (6.90 g, 50 mmol) in DMF (200 mL) was added $I_2$ (10.15 g, 40 mmol). The mixture was stirred at 55° C. for 18 h and poured into ice-cooled water (300 mL). The formed precipitate was filtered off, washed with water, and dried at 60° C. to afford 5.81 g (98%) of 3-Iodo-1H-pyrazolo[4,3-c]quinoline (P20). $^1H$ NMR (400 MHz, DMSO-$d_6$): δ 14.75 (s, 1H), 8.89 (s, 1H), 8.41 (m, 1H), 8.15 (d, J=8.4 Hz, 1H), 7.81 (m, 1H), 7.74 (m, 1H).

Preparation 39: 3-iodo-8-methoxy-1H-pyrazolo[4,3-c]quinoline (P21)

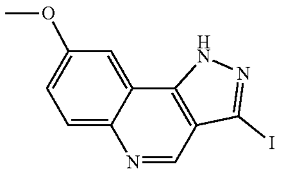 [SMILES: COc1ccc2ncc3c(I)n[nH]c3c2c1]

The compound was synthesized according to the procedure described in Preparation 38 using 8-methoxy-1H-pyrazolo[4,3-c]quinoline (P18) instead of 1H-pyrazolo[4,3-c]quinoline. $^1$H NMR (400 MHz, DMSO-$d_6$): δ 14.57 (s, 1H), 8.73 (s, 1H), 8.05 (d, J=9.2 Hz, 1H), 7.85 (d, J=2.0 Hz, 1H), 7.42 (dd, $J_1$=9.2 Hz, $J_2$=2.0 Hz, 1H), 3.95 (s, 3H).

Preparation 40: 3-iodo-6-methoxy-1H-pyrazolo[4,3-c]quinoline (P22)

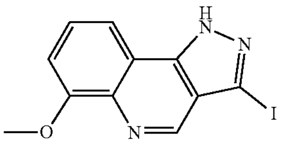 [SMILES: COc1cccc2c1ncc1c(I)n[nH]c12]

The compound was synthesized according to the procedure described in Preparation 38 using 6-methoxy-1H-pyrazolo[4,3-c]quinoline (P19) instead of 1H-pyrazolo[4,3-c]quinoline. $^1$H NMR (400 MHz, DMSO-$d_6$): δ 14.69 (s, 1H), 8.82 (s, 1H), 7.93 (d, J=8.0 Hz, 1H), 7.66 (t, J=8.0 Hz, 1H), 7.30 (d, J=8.0 Hz, 1H), 3.99 (s, 3H).

Preparation 41: 3-(3,4-dimethoxyphenyl)-1H-pyrazolo[4,3-c]quinoline (P23)

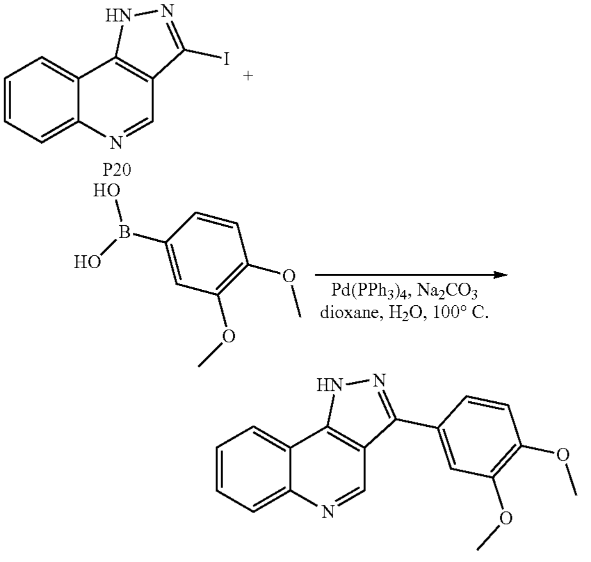

P23

A mixture of 3-Iodo-1H-pyrazolo[4,3-c]quinoline (P20, see Preparation 38) (5.31 g, 18 mmol), 3,4-dimethoxyboronic acid (3.93 g, 21.6 mmol) and $Na_2CO_3$ (5.72 g, 54 mmol), $Pd(PPh_3)_4$ (1.04 g, 0.9 mmol), dioxane (150 mL), and water (30 mL) was degassed, stirred in Ar atmosphere at 100° C. for 15 h, cooled, diluted with water (450 mL), and extracted with i-PrOAc (3×150 mL). The combined organic layers were washed with water, brine, dried over $Na_2SO_4$, and concentrated under reduced pressure. The residue was treated with MTBE, filtered off, and dried at 60° C. to afford 3-(3,4-dimethoxyphenyl)-1H-pyrazolo[4,3-c]quinoline (P23). $^1$H NMR (400 MHz, DMSO-$d_6$): δ 14.33 (s, 1H), 9.49 (s, 1H), 8.47 (m, 1H), 8.15 (m, 1H), 7.77 (m, 2H), 7.66 (m, 1H), 7.60 (m, 1H), 7.47 (m, 1H), 7.15 (d, J=8.0 Hz, 1H), 3.91 (s, 3H), 3.85 (s, 3H).

Preparation 42: 3-(3,4-dimethoxyphenyl)-8-methoxy-1H-pyrazolo[4,3-c]quinoline (P24)

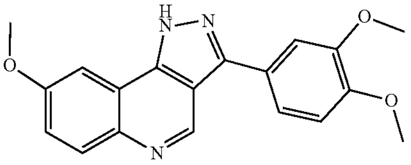 [SMILES: COc1ccc2ncc3c(-c4ccc(OC)c(OC)c4)n[nH]c3c2c1]

The compound was synthesized according to the procedure described in Preparation 41 using 3-iodo-8-methoxy-1H-pyrazolo[4,3-c]quinoline (P21) instead of 3-iodo-1H-pyrazolo[4,3-c]quinoline. $^1$H NMR (400 MHz, DMSO-$d_6$): δ 14.18 (s, 1H), 9.34 (s, 1H), 8.05 (d, J=9.2 Hz, 1H), 7.93 (d, J=2.8 Hz, 1H), 7.65 (dd, $J_1$=8.0 Hz, $J_2$=1.6 Hz, 1H), 7.59 (d, J=1.6 Hz, 1H), 7.41 (dd, $J_1$=9.2 Hz, $J_2$=2.8 Hz, 1H), 7.14 (d, J=8.0 Hz, 1H), 3.97 (s, 3H), 3.90 (s, 3H), 3.85 (s, 3H).

Preparation 43: 3-(3,4-dimethoxyphenyl)-6-methoxy-1H-pyrazolo[4,3-c]quinoline (P25)

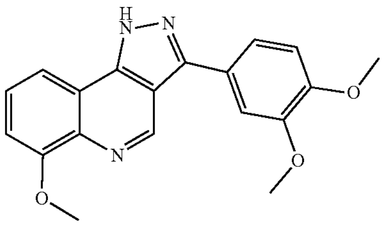 [SMILES: COc1ccc(-c2n[nH]c3c2cnc2c(OC)cccc23)cc1OC]

The compound was synthesized according to the procedure described in Preparation 41 using 3-iodo-6-methoxy-1H-pyrazolo[4,3-c]quinoline (P22) instead of 3-iodo-1H-pyrazolo[4,3-c]quinoline. $^1$H NMR (400 MHz, DMSO-$d_6$): δ 14.28 (s, 1H), 9.43 (s, 1H), 8.00 (d, J=8.0 Hz, 1H), 7.65 (m, 2H), 7.59 (s, 1H), 7.28 (d, J=8.0 Hz, 1H), 7.16 (d, J=8.4 Hz, 1H), 4.00 (s, 3H), 3.91 (s, 3H), 3.85 (s, 3H).

REPRESENTATIVE EXAMPLES OF THE COMPOUND

Example 1: 3-(3,4-dimethoxyphenyl)-8-methoxy-2-(2-morpholin-4-ylethyl)-2H-pyrazolo[4,3-c]quinoline (1.40) and 3-(3,4-dimethoxyphenyl)-8-methoxy-2-(2-morpholin-4-ylethyl)-2H-pyrazolo[4,3-c]quinoline (1.40a)

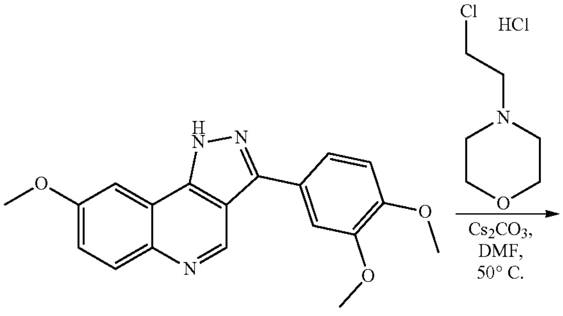

P24

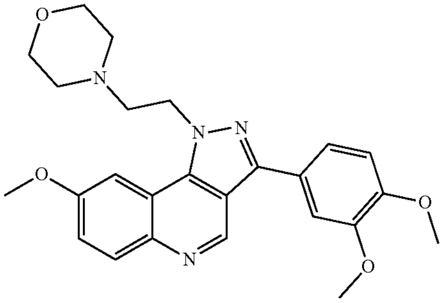

+ +

P26

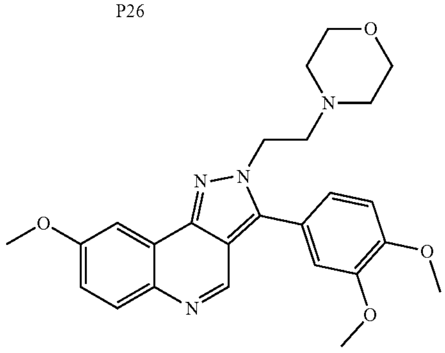

P26A

A mixture of 3-(3,4-dimethoxyphenyl)-8-methoxy-1H-pyrazolo[4,3-c]quinoline (P24) (198 mg, 0.59 mmol), $Cs_2CO_3$ (385 mg, 1.18 mmol), 4-(2-chloroethyl)morpholine hydrochloride (110 mg, 0.59 mmol), and DMF (2 mL) was stirred at ambient temperature for 48 h, diluted with EtOAc, washed with water, brine, and concentrated under reduced pressure. The residue was subjected to HPLC purification to afford 17 mg (6%) of 3-(3,4-dimethoxyphenyl)-8-methoxy-2-(2-morpholin-4-ylethyl)-2H-pyrazolo[4,3-c]quinoline (P26, 1.40) and 50 mg (19%) of 3-(3,4-dimethoxyphenyl)-8-methoxy-2-(2-morpholin-4-ylethyl)-2H-pyrazolo[4,3-c] quinoline (P26A). The structures assignment was done using 2D-NOESY NMR spectroscopy. P26 (1.40): $^1H$ NMR (400 MHz, DMSO-$d_6$): δ 9.29 (s, 1H), 8.11 (d, J=9.2 Hz, 1H), 7.79 (d, J=2.4 Hz, 1H), 7.58 (dd, $J_1$=8.0 Hz, $J_2$=1.6 Hz, 1H), 7.51 (d, J=1.6 Hz, 1H), 7.46 (dd, $J_1$=8.8 Hz, $J_2$=2.4 Hz, 1H), 7.14 (d, J=8.0 Hz, 1H), 5.03 (t, J=7.0 Hz, 2H), 4.02 (s, 3H), 3.89 (s, 3H), 3.84 (s, 3H), 3.53 (m, 4H), 2.91 (t, J=7.0 Hz, 2H), 2.51 (m, 4H); LCMS (ESI) m/z 449.5 $[M+H]^+$. P26A: $^1H$ NMR (400 MHz, DMSO-$d_6$): δ 8.84 (s, 1H), 7.94 (d, J=9.2 Hz, 1H), 7.76 (d, J=2.4 Hz, 1H), 7.31 (m, 3H), 7.23 (m, 1H), 4.58 (t, J=6.0 Hz, 2H), 3.96 (s, 3H), 3.88 (s, 3H), 3.87 (s, 3H), 3.43 (m, 4H), 2.89 (t, J=6.0 Hz, 2H), 2.25 (m, 4H); LCMS (ESI) m/z 449.5 $[M+H]^+$.

Example 2: 1-{3-[1-(3,4-dimethylphenyl)-8-methoxy-1H-pyrazolo[4,3-c]quinolin-3-yl]phenyl}-N,N-dimethylpiperidin-4-amine (1.1)

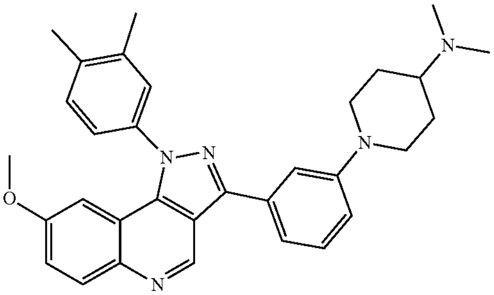

A mixture of 3-(3-Bromophenyl)-1-(3,4-dimethylphenyl)-8-methoxy-1H-pyrazolo[4,3-c]quinoline (P1) (50.0 mg, 0.109 mmol), 4-dimethylamino-piperidine (21.0 mg, 0.163 mmol), t-BuONa (21.0 mg, 0.218 mmol), XPhos (5.1 mg, 0.011 mmol), $Pd(OAc)_2$ (1.2 mg, 0.005 mmol), and degassed dioxane (1 mL,) in sealed tube in inert atmosphere was stirred at 100° C. overnight, cooled, filtered through Celite pad, and concentrated under reduced pressure. The residue was subjected to silica FC eluting with a mixture of DCM and EtOAc (25 to 50%) to afford 17.0 mg (33%) of 1-{3-[1-(3,4-dimethylphenyl)-8-methoxy-1H-pyrazolo[4,3-c]quinolin-3-yl]phenyl}-N,N-dimethylpiperidin-4-amine (1.1) as a slight yellow solid. $^1H$ NMR (400 MHz, $CDCl_3$): 9.37 (s, 1H), 8.15 (d, J=9.2 Hz, 1H), 7.59-7.57 (m, 2H), 7.50-7.39 (m, 4H), 7.34-7.31 (m, 1H), 7.07-7.03 (m, 1H), 6.97 (d, J=2.7 Hz, 1H), 3.98-3.94 (m, 2H), 3.58 (s, 3H), 3.22-3.11 (m, 1H), 2.92-2.86 (m, 2H), 2.75 (s, 6H), 2.43 (s, 3H), 2.40 (s, 3H), 2.29-2.25 (m, 2H), 1.97-1.88 (m, 2H).

Example 3: 1-(3,4-dimethylphenyl)-8-methoxy-3-(3-morpholin-4-ylphenyl)-1H-pyrazolo[4,3-c]quinoline (1.2)

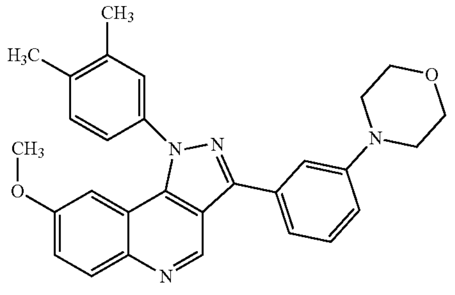 [SMILES: COc1ccc2ncc3c(-c4cccc(N5CCOCC5)c4)nn(-c4ccc(C)c(C)c4)c3c2c1]

The compound was synthesized according to the procedure described in Example 2 using morpholine instead of 4-dimethylamino-piperidine. $^1H$ NMR (400 MHz, $CDCl_3$): 9.39 (s, 1H), 8.19 (d, J=9.4 Hz, 1H), 7.59-7.39 (m, 6H), 7.35-7.32 (m, 1H), 7.06-7.03 (m, 1H), 6.99-6.98 (m, 1H), 3.91-3.89 (m, 4H), 3.57 (s, 3H), 3.30-3.28 (m, 4H), 2.43 (s, 3H), 2.40 (s, 3H).

Example 4: 1-(3,4-dimethylphenyl)-8-methoxy-3-[3-(4-methylpiperazin-1-yl)phenyl]-1H-pyrazolo[4,3-c]quinoline (1.3)

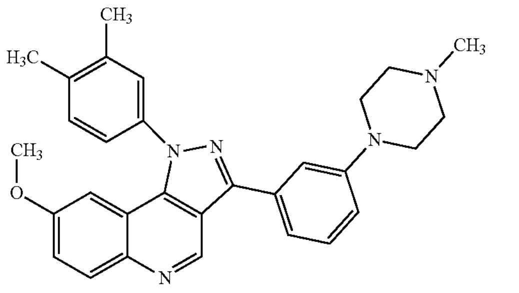 [SMILES: COc1ccc2ncc3c(-c4cccc(N5CCN(C)CC5)c4)nn(-c4ccc(C)c(C)c4)c3c2c1]

The compound was synthesized according to the procedure described in Example 2 using N-methylpiperazine instead of 4-dimethylamino-piperidine. $^1$H NMR (400 MHz, DMSO-$d_6$): 9.37 (s, 1H), 8.09 (d, J=9.0 Hz, 1H), 7.55-7.38 (m, 7H), 7.11-7.09 (m, 1H), 6.87 (d, J=2.7 Hz, 1H), 3.54 (s, 3H), 3.26-3.23 (m, 4H), 2.51-2.48 (m, 4H), 2.40 (s, 3H), 2.36 (s, 3H), 2.24 (s, 3H).

Example 5: 1-{3-[8-methoxy-3-(3-methoxyphenyl)-1H-pyrazolo[4,3-c]quinolin-1-yl]phenyl}-N,N-dimethylpiperidin-4-amine (1.4)

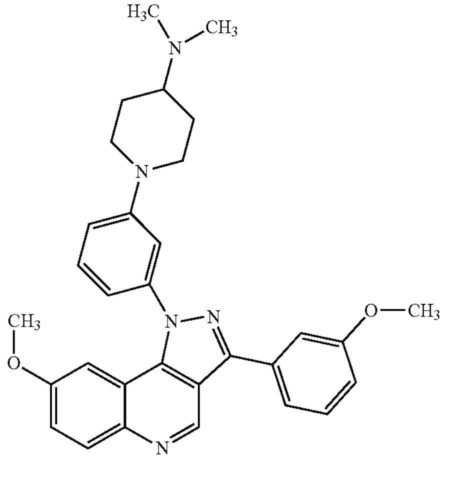 [SMILES: COc1cccc(-c2nn(-c3cccc(N4CCC(N(C)C)CC4)c3)c3c2cnc2ccc(OC)cc23)c1]

The compound was synthesized according to the procedure described in Example 2 using 1-(3-bromophenyl)-8-methoxy-3-(3-methoxyphenyl)-1H-pyrazolo[4,3-c]quinoline (P2) instead of 3-(3-bromophenyl)-1-(3,4-dimethylphenyl)-8-methoxy-1H-pyrazolo[4,3-c]quinoline. Yield 21%. $^1$H NMR (400 MHz, DMSO-$d_6$) δ 9.41 (s, 1H), 8.10 (d, J=9.1 Hz, 1H), 7.69 (d, J=7.5 Hz, 1H), 7.53-7.51 (m, 3H), 7.40-7.38 (m, 1H), 7.27-7.25 (m, 2H), 7.10 (t, J=7.4 Hz, 2H), 6.92 (s, 1H), 3.95-3.87 (m, 4H), 3.55 (s, 3H), 3.35-3.28 (m, 2H), 2.80-2.74 (m, 2H), 2.51-2.48 (m, 6H), 2.00-1.94 (m, 2H), 1.66-1.60 (m, 2H).

Example 6: 8-methoxy-3-(3-methoxyphenyl)-1-[3-(4-methylpiperazin-1-yl)phenyl]-1H-pyrazolo[4,3-c]quinoline (1.5)

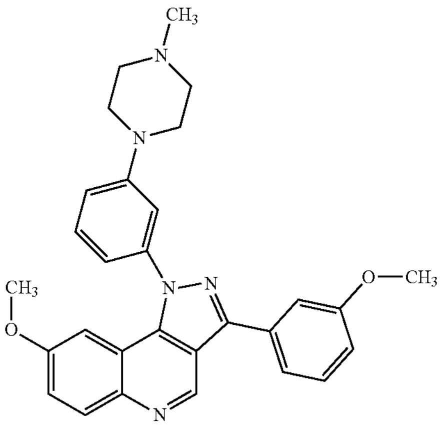 [SMILES: COc1cccc(-c2nn(-c3cccc(N4CCN(C)CC4)c3)c3c2cnc2ccc(OC)cc23)c1]

The compound was synthesized according to the procedure described in Example 2 using 1-(3-bromophenyl)-8-methoxy-3-(3-methoxyphenyl)-1H-pyrazolo[4,3-c]quinoline (P2) instead of 3-(3-bromophenyl)-1-(3,4-dimethylphenyl)-8-methoxy-1H-pyrazolo[4,3-c]quinoline and 1-methylpiperazine instead of 4-dimethylamino-piperidine. Yield 44%. $^1$H NMR (400 MHz, DMSO-$d_6$): 9.42 (s, 1H), 8.08 (d, J=9.0 Hz, 1H), 7.69 (d, J=7.6 Hz, 1H), 7.56-7.59 (m, 3H), 7.42-7.38 (m, 1H), 7.28-7.26 (m, 2H), 7.12-7.08 (m, 2H), 6.92-6.91 (m, 1H), 3.87 (s, 3H), 3.55 (s, 3H), 3.31-3.22 (m, 7H), 2.27-2.20 (m, 4H).

Example 7: 1-{3-[8-methoxy-3-(3-methoxyphenyl)-1H-pyrazolo[4,3-c]quinolin-1-yl]-4-methylphenyl}-N,N-dimethylpiperidin-4-amine (1.7)

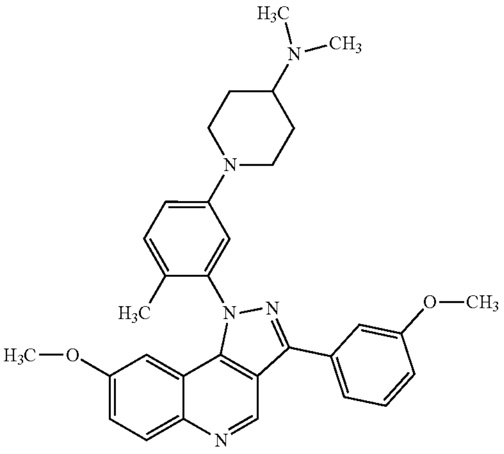

The compound was synthesized according to the procedure described in Example 2 using P3 instead of P1 and 4-dimethylamino-piperidine. $^1$H NMR (400 MHz, DMSO-$d_6$): 9.45 (s, 1H), 8.08 (d, J=9.0 Hz, 1H), 7.71 (d, J=7.8 Hz, 1H), 7.58 (s, 1H), 7.51 (t, J=7.9 Hz, 1H), 7.43-7.41 (m, 2H), 7.25-7.23 (m, 1H), 7.19-7.18 (m, 1H), 7.09-7.08 (m, 1H), 6.64-6.62 (m, 1H), 3.88 (s, 3H), 3.82-3.79 (m, 2H), 3.50 (s, 3H), 3.31 (br., 1H), 2.74-2.67 (m, 2H), 2.31-2.29 (br, 6H), 1.86-1.81 (m, 5H), 1.56-1.57 (m, 2H).

Example 8: 8-methoxy-3-(3-methoxyphenyl)-1-[2-methyl-5-(4-methylpiperazin-1-yl)phenyl]-1H-pyrazolo[4,3-c]quinoline (1.8)

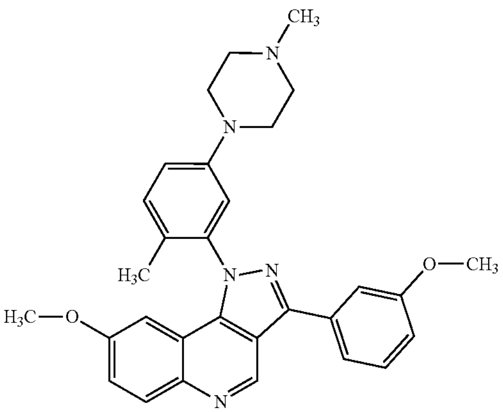

The compound was synthesized according to the procedure described in Example 2 using 1-(5-chloro-2-methylphenyl)-8-methoxy-3-(3-methoxyphenyl)-1H-pyrazolo[4,3-c]quinoline (P3) instead of 3-(3-bromophenyl)-1-(3,4-dimethylphenyl)-8-methoxy-1H-pyrazolo[4,3-c]quinoline and 1-methyl-piperazine instead of 4-dimethylamino-piperidine. Yield 18%. $^1$H NMR (400 MHz, DMSO-$d_6$): 9.45 (s, 1H), 8.08 (d, J=9.0 Hz, 1H), 7.71 (d, J=7.8 Hz, 1H), 7.58 (s, 1H), 7.51 (t, J=7.8 Hz, 1H), 7.43-7.38 (m, 2H), 7.24-7.18 (m, 2H), 7.10-7.07 (m, 1H), 6.64-6.63 (m, 1H), 3.88 (s, 3H), 3.50 (s, 3H), 3.19-3.15 (m, 2H), 2.44-2.41 (m, 2H), 2.19 (s, 3H), 1.82 (s, 3H).

Example 9: 1-{3-[3-(3,4-dimethylphenyl)-8-methoxy-1H-pyrazolo[4,3-c]quinolin-1-yl]-4-methylphenyl}-N,N-dimethylpiperidin-4-amine (1.10)

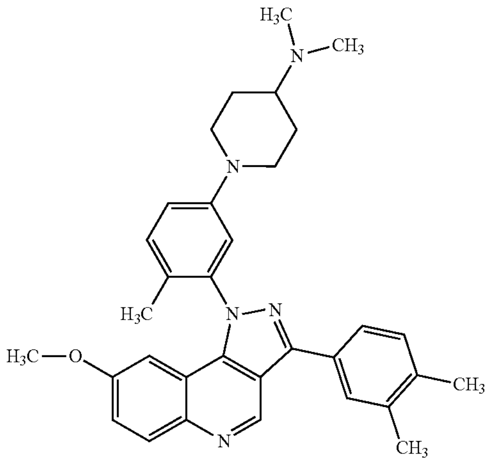

The compound was synthesized according to the procedure described in Example 2 using 1-(5-chloro-2-methylphenyl)-3-(3,4-dimethylphenyl)-8-methoxy-1H-pyrazolo[4,3-c]quinoline (P4) instead of 3-(3-bromophenyl)-1-(3,4-dimethylphenyl)-8-methoxy-1H-pyrazolo[4,3-c]quinoline Yield 53%. $^1$H NMR (400 MHz, DMSO-$d_6$): 9.45 (s, 1H), 8.08 (d, J=9.0 Hz, 1H), 7.89 (s, 1H), 7.84 (d, J=8.8 1H), 742-7.34 (m, 3H), 7.27-7.21 (m, 1H), 7.19-7.18 (m, 1H), 6.64-6.62 (m, 1H), 3.84-3.79 (m, 2H), 3.50 (s, 3H), 2.75-2.68 (m, 2H), 2.36-2.32 (m, 9H), 1.91-1.80 (m, 5H), 1.59-1.50 (m, 2H).

Example 10: 3-(3,4-dimethylphenyl)-8-methoxy-1-[2-methyl-5-(4-methylpiperazin-1-yl)phenyl]-1H-pyrazolo[4,3-c]quinoline (1.11)

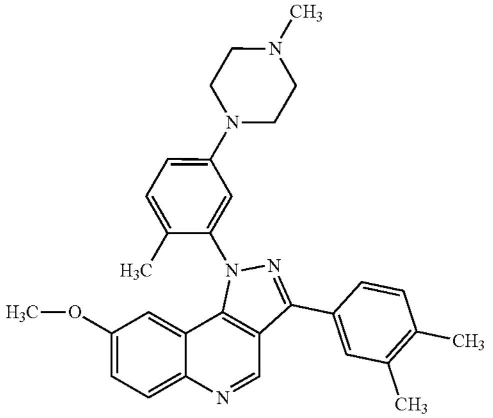

The compound was synthesized according to the procedure described in Example 2 using 1-(5-chloro-2-methylphenyl)-3-(3,4-dimethylphenyl)-8-methoxy-1H-pyrazolo[4,3-c]quinoline (P4) instead of 3-(3-bromophenyl)-1-(3,4-dimethylphenyl)-8-methoxy-1H-pyrazolo[4,3-c]quinoline and 1-methyl-piperazine instead of 4-dimethylamino-piperidine. Yield 41%. $^1$H NMR (400 MHz, DMSO-$d_6$): 9.45 (s, 1H), 8.08 (d, J=9.0 Hz, 1H), 7.88-7.83 (m, 2H), 7.42-7.34 (m, 4H), 7.24 (d, J=9.0 Hz, 1H), 7.17-7.18 (m, 1H), 6.64-6.63 (m, 1H), 3.50 (s, 3H), 3.19-3.16 (m, 4H), 2.44-2.41 (m, 4H), 2.36 (s, 3H), 2.32 (s, 3H), 2.20-2.18 (m, 3H), 1.82 (s, 3H).

Example 11: 1-{3-[3-(3,4-dimethylphenyl)-8-methoxy-1H-pyrazolo[4,3-c]quinolin-1-yl]phenyl}-N,N-dimethylpiperidin-4-amine (1.13)

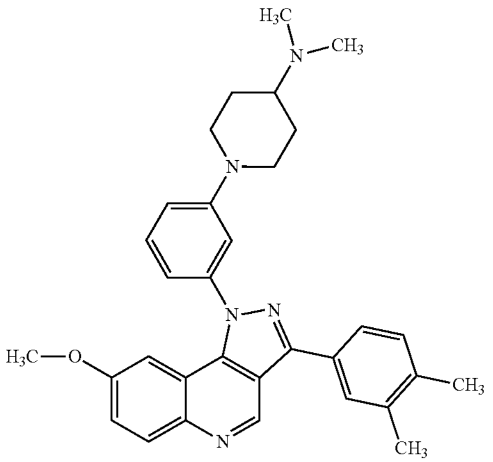

The compound was synthesized according to the procedure described in Example 2 using 1-(3-bromophenyl)-3-(3,4-dimethylphenyl)-8-methoxy-1H-pyrazolo[4,3-c]quinoline (P5) instead of 3-(3-bromophenyl)-1-(3,4-dimethylphenyl)-8-methoxy-1H-pyrazolo[4,3-c]quinoline.

Example 12: 1-{3-[1-(2,3-dimethylphenyl)-8-methoxy-1H-pyrazolo[4,3-c]quinolin-3-yl]phenyl}-N,N-dimethylpiperidin-4-amine (1.14)

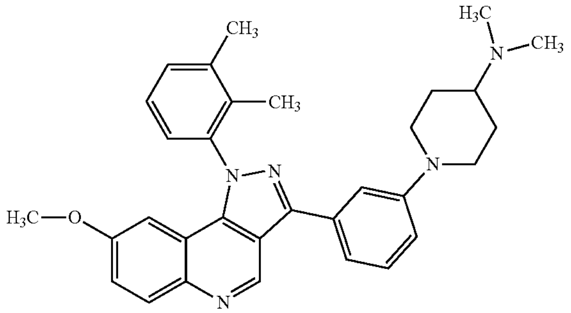

The compound was synthesized according to the procedure described in Example 2 using 3-(3-bromophenyl)-1-(2,3-dimethylphenyl)-8-methoxy-1H-pyrazolo[4,3-c]quinoline (P6) instead of 3-(3-bromophenyl)-1-(3,4-dimethylphenyl)-8-methoxy-1H-pyrazolo[4,3-c]quinoline. Yield 12%. $^{1}$H NMR (400 MHz, DMSO-$d_6$) δ 9.42 (s, 1H), 8.09 (d, J=9.1 Hz, 1H), 7.69-7.31 (m, 7H), 7.13 (d, J=8.1 Hz, 1H), 6.49 (d, J=2.6 Hz, 1H), 3.91 (m, 2H), 3.42 (s, 3H), 2.77 (t, J=12.1, 2H), 2.53 (s, 3H), 2.42 (s, 3H), 2.00 (m, 2H), 1.81 (s, 3H), 1.64 (m, 2H).

Example 13: 1-(3,4-dimethylphenyl)-8-methoxy-3-(4-morpholin-4-ylphenyl)-1H-pyrazolo[4,3-c]quinoline (1.15)

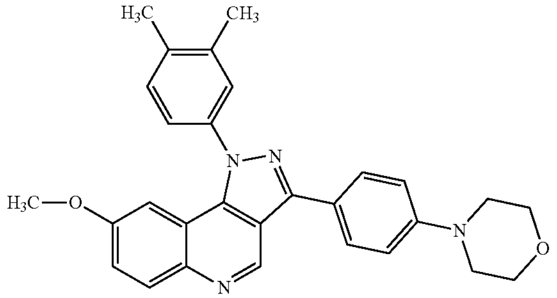 [SMILES: COc1ccc2ncc3c(-c4ccc(N5CCOCC5)cc4)nn(-c4ccc(C)c(C)c4)c3c2c1]

The compound was synthesized according to the procedure described in Example 2 using 3-(4-bromophenyl)-1-(3,4-dimethylphenyl)-8-methoxy-1H-pyrazolo[4,3-c]quinoline (P7) instead of 3-(3-bromophenyl)-1-(3,4-dimethylphenyl)-8-methoxy-1H-pyrazolo[4,3-c]quinoline and morpholine instead of 4-dimethylamino-piperidine. Yield 22%. $^{1}$H-NMR (400 MHz, $CDCl_3$) δ: 9.39 (s, 1H), 8.18 (d, J=9.5 Hz, 1H), 8.00 (d, J=8.5 Hz, 2H), 7.48 (s, 1H), 7.45-7.37 (m, 2H), 7.35-7.30 (m, 1H), 7.09 (d, J=8.3 Hz, 2H), 7.01-6.96 (m, 1H), 3.96-3.89 (m, 4H), 3.58 (s, 3H), 3.34-3.26 (m, 4H), 2.43 (s, 3H), 2.40 (s, 3H).

Example 14: 1-(3,4-dimethylphenyl)-8-methoxy-3-[4-(4-methylpiperazin-1-yl)phenyl]-1H-pyrazolo[4,3-c]quinoline (1.16)

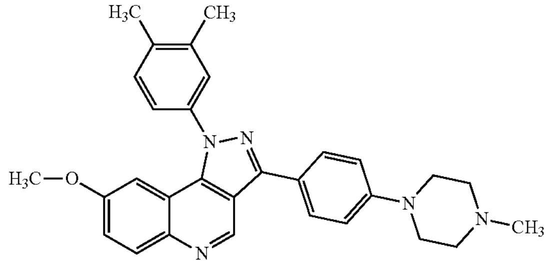

The compound was synthesized according to the procedure described in Example 2 using 3-(4-bromophenyl)-1-(3,4-dimethylphenyl)-8-methoxy-1H-pyrazolo[4,3-c]quinoline (P7) instead of 3-(3-bromophenyl)-1-(3,4-dimethylphenyl)-8-methoxy-1H-pyrazolo[4,3-c]quinoline and 1-methyl-piperazine instead of 4-dimethylamino-piperidine. Yield 29%. $^{1}$H-NMR (400 MHz, DMSO-d6) δ: 9.38 (s, 1H), 8.09 (d, J=9.1 Hz, 1H), 7.94 (d, J=8.8 Hz, 2H), 7.54 (s, 1H), 7.47 (s, 2H), 7.38 (dd, $J_1$=9.0 Hz, $J_2$=2.8 Hz, 1H), 7.12 (d, J=8.6 Hz, 2H), 7.86 (d, J=2.8 Hz, 1H), 3.54 (s, 3H), 3.29-3.20 (m, 4H), 2.53-2.44 (m, 4H), 2.40 (s, 3H), 2.36 (s, 3H), 2.24 (s, 3H).

Example 15: 1-{4-[1-(3,4-dimethylphenyl)-8-methoxy-1H-pyrazolo[4,3-c]quinolin-3-yl]phenyl}-N,N-dimethylpiperidin-4-amine (1.17)

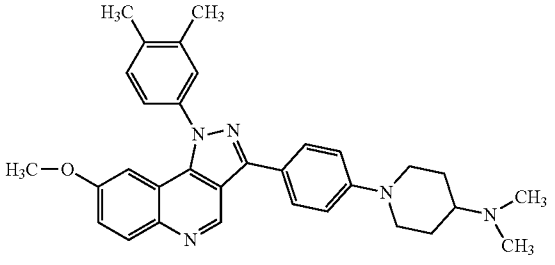

The compound was synthesized according to the procedure described in Example 2 using 3-(4-bromophenyl)-1-(3,4-dimethylphenyl)-8-methoxy-1H-pyrazolo[4,3-c]quinoline (P7) instead of 3-(3-bromophenyl)-1-(3,4-dimethylphenyl)-8-methoxy-1H-pyrazolo[4,3-c]quinoline. Yield 5%. $^{1}$H NMR (400 MHz, DMSO-$d_6$): 9.37 (s, 1H), 8.08 (d, J=9.2 Hz, 1H), 7.90 (d, J=8.7 Hz, 2H), 7.53-7.46 (m, 3H), 7.39 (d, J=6.5 Hz, 1H), 7.14 (d, J=8.6 Hz, 2H), 6.87 (d, J=2.4 Hz, 1H), 3.94-3.91 (m, 2H), 3.53 (s, 3H), 3.45-3.40 (m, 1H), 2.82-2.78 (m, 2H), 2.51-2.47 (m, 6H), 2.40 (s, 3H), 2.36 (s, 3H), 2.00-1.95 (m, 2H), 1.64-1.56 (m, 2H).

Example 16: N-{4-[1-(3,4-dimethylphenyl)-8-methoxy-1H-pyrazolo[4,3-c]quinolin-3-yl]phenyl}-N,N',N'-trimethylpropane-1,3-diamine (1.18)

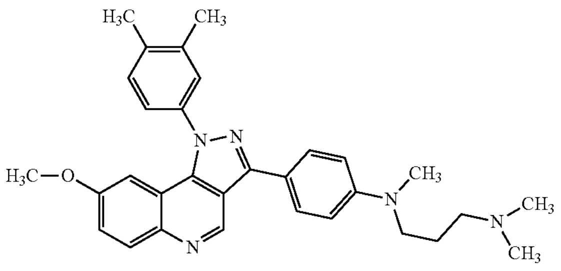

The compound was synthesized according to the procedure described in Example 2 using 3-(4-bromophenyl)-1-(3,4-dimethylphenyl)-8-methoxy-1H-pyrazolo[4,3-c]quinoline (P7) instead of 3-(3-bromophenyl)-1-(3,4-dimethylphenyl)-8-methoxy-1H-pyrazolo[4,3-c]quinoline and N,N,N'-trimethylpropane-1,3-diamine instead of 4-dimethylamino-piperidine. Yield 17%. $^1$H NMR (400 MHz, DMSO-$d_6$): 9.37 (s, 1H), 8.08 (d, J=9.2 Hz, 1H), 7.90 (d, J=8.7 Hz, 2H), 7.53-7.46 (m, 3H), 7.38 (d, J=6.8 Hz, 1H), 6.89-6.87 (m, 3H), 3.53 (s, 3H), 3.45-3.42 (m, 2H), 2.98 (s, 3H), 2.39 (s, 3H), 2.36 (s, 3H), 2.23-2.21 (m, 5H), 1.74-1.68 (m, 2H).

Example 17: 1-(3,4-dimethylphenyl)-3-(4-morpholin-4-ylphenyl)-1H-pyrazolo[4,3-c]quinoline (1.20)

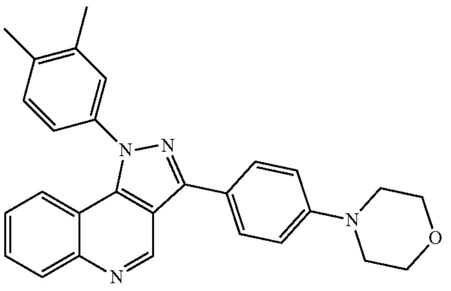 [SMILES: Cc1ccc(-n2nc(-c3ccc(N4CCOCC4)cc3)c3cnc4ccccc4c32)cc1C]

The compound was synthesized according to the procedure described in Example 2 using 3-(4-bromophenyl)-1-(3,4-dimethylphenyl)-1H-pyrazolo[4,3-c]quinoline (P8) instead of 3-(3-bromophenyl)-1-(3,4-dimethylphenyl)-8-methoxy-1H-pyrazolo[4,3-c]quinoline and morpholine instead of 4-dimethylamino-piperidine. Yield 39%. $^1$H-NMR (400 MHz, $CDCl_3$) δ: 9.51 (s, 1H), 8.28 (d, J=8.8 Hz, 1H), 7.99 (d, J=8.2 Hz, 2H), 7.71 (t, J=7.0 Hz, 1H), 7.66 (d, J=9.0 Hz, 1H), 7.46 (s, 1H), 7.43-7.36 (m, 3H), 7.09 (d, J=8.7 Hz, 2H), 3.97-3.87 (m, 4H), 3.35-3.25 (m, 4H), 2.45 (s, 3H), 2.40 (s, 3H).

Example 18: 1-(3,4-dimethylphenyl)-3-[4-(4-methylpiperazin-1-yl)phenyl]-1H-pyrazolo[4,3-c]quinoline (1.21)

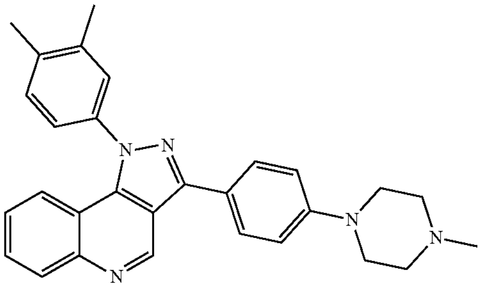 [SMILES: Cc1ccc(-n2nc(-c3ccc(N4CCN(C)CC4)cc3)c3cnc4ccccc4c32)cc1C]

The compound was synthesized according to the procedure described in Example 2 using 3-(4-bromophenyl)-1-(3,4-dimethylphenyl)-1H-pyrazolo[4,3-c]quinoline (P8) instead of 3-(3-bromophenyl)-1-(3,4-dimethylphenyl)-8-methoxy-1H-pyrazolo[4,3-c]quinoline and 1-methyl-piperazine instead of 4-dimethylamino-piperidine. Yield 13%. $^1$H-NMR (400 MHz, $CDCl_3$) δ: 9.50 (s, 1H), 8.24 (d, J=8.4 Hz, 1H), 7.97 (d, J=8.4 Hz, 2H), 7.71-7.64 (m, 2H), 7.45-7.36 (m, 4H), 7.11 (d, J=8.7 Hz, 2H), 3.39-3.36 (m, 4H), 2.67-2.65 (m, 4H), 2.44 (s, 3H), 2.41 (s, 3H), 2.38 (s, 3H).

Example 19: 3-(4-morpholin-4-ylphenyl)-1-phenyl-1H-pyrazolo[4,3-c]quinoline (1.23)

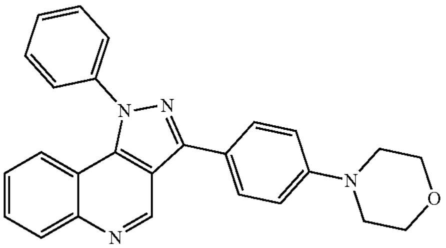 [SMILES: c1ccc(-n2nc(-c3ccc(N4CCOCC4)cc3)c3cnc4ccccc4c32)cc1]

The compound was synthesized according to the procedure described in Example 2 using 3-(4-bromophenyl)-1-phenyl-1H-pyrazolo[4,3-c]quinoline (see Preparation 14) instead of 3-(3-bromophenyl)-1-(3,4-dimethylphenyl)-8-methoxy-1H-pyrazolo[4,3-c]quinoline and morpholine instead of 4-dimethylamino-piperidine. $^1$H-NMR (400 MHz, $CDCl_3$) δ: 9.52 (s, 1H), 8.25 (d, J=7.8 Hz, 1H), 8.00 (d, J=8.4 Hz, 2H), 7.72-7.60 (m, 7H), 7.40-7.36 (m, 1H), 7.10 (d, J=8.4 Hz, 2H), 3.93-3.91 (m, 4H), 3.30-3.25 (m, 4H).

Example 20: 1-(3,4-dimethylphenyl)-8-methoxy-3-[3-(piperazin-1-yl)phenyl]-1H-pyrazolo[4,3-c]quinoline (1.41)

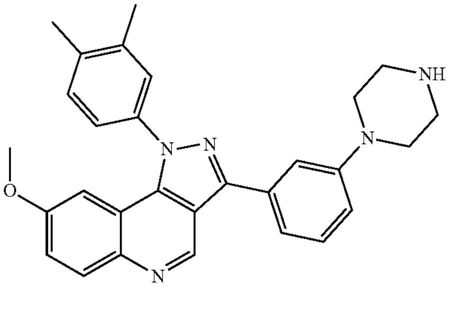 [SMILES: COc1ccc2ncc3c(-c4cccc(N5CCNCC5)c4)nn(-c4ccc(C)c(C)c4)c3c2c1]

The compound was synthesized according to the procedure described in Example 2 using piperazine instead of 4-dimethylamino-piperidine.

Example 21: N-{3-[1-(3,4-dimethylphenyl)-8-methoxy-1H-pyrazolo[4,3-c]quinolin-3-yl]phenyl}-N,N',N'-trimethylpropane-1,3-diamine (1.42)

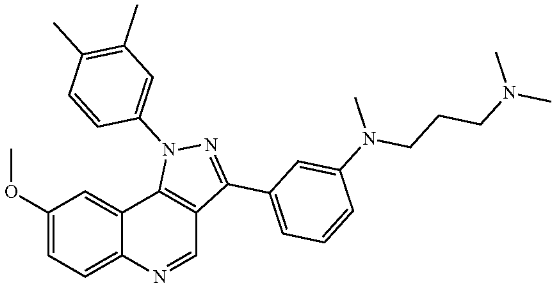 [SMILES: COc1ccc2ncc3c(-c4cccc(N(C)CCCN(C)C)c4)nn(-c4ccc(C)c(C)c4)c3c2c1]

The compound was synthesized according to the procedure described in Example 2 using N,N,N'-trimethylpropane-1,3-diamine instead of 4-dimethylamino-piperidine.

Example 22: 1-(3,4-dimethylphenyl)-8-methoxy-3-(4-pyridin-4-ylphenyl)-1H-pyrazolo[4,3-c]quinoline (1.19)

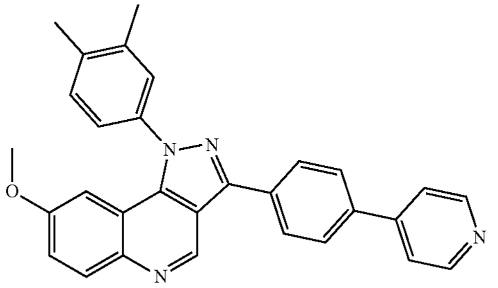 [SMILES: COc1ccc2ncc3c(-c4ccc(-c5ccncc5)cc4)nn(-c4ccc(C)c(C)c4)c3c2c1]

A degassed mixture of 3-(4-bromophenyl)-1-(3,4-dimethylphenyl)-8-methoxy-1H-pyrazolo[4,3-c]quinoline (P7, 140 mg, 0.305 mmol), pyridin-4-ylboronic acid (45 mg. 0.366 mmol), cesium carbonate (199 mg, 0.611 mmol), $Pd(PPh_3)_4$ (35 mg, 0.03 mmol), and dioxane (5 mL) was stirred and heated in a sealed tube at 100° C. for 12 h, cooled, diluted with EtOAc, and filtered through Celite pad. The filtrate was washed with sat. aq. solution of $NaHCO_3$, water, brine, dried over $Na_2SO_4$, and evaporated under reduced pressure. The residue was subjected to silica CC eluting with a mixture of DCM and EtOAc (9:1) to afford 100 mg, (71%) of the title compound 1.19 as a white solid. $^1H$ NMR (400 MHz, DMSO-$d_6$): 9.72 (s, 1H), 8.97 (d, J=6.0 Hz, 2H), 8.36 (d, J=8.4 Hz, 2H), 8.24-8.18 (m, 5H), 7.62 (s, 1H), 7.51-7.48 (m, 1H), 7.55-7.53 (m, 3H), 6.89 (d, J=2.8 Hz, 1H), 2.42 (s, 3H), 2.39 (s, 3H).

Example 23: 4-{[(1S)-2-hydroxy-1-phenylethyl]amino}-N-methyl-2-[(2-methyl-3-oxo-1,2,3,4-tetrahydroisoquinolin-7-yl)amino]pyrimidine-5-carboxamide—Compound 44. The compound was synthesized according to the procedure described in Example 19 using 4-{[(1S)-2-hydroxy-1-phenylethyl]amino}-2-[(2-methyl-3-oxo-1,2,3,4-tetrahydroisoquinolin-7-yl)amino]pyrimidine-5-carboxylic acid instead of 4-{[(1S)-2-hydroxy-1-phenylethyl]amino}-2-{[3-methyl-4-(methylsulfonyl)phenyl]amino}pyrimidine-5-carboxylic acid and methylamine hydrochloride instead of ethylamine hydrochloride.

Example 24: 1-(3,4-dimethylphenyl)-3-(4-piperazin-1-ylphenyl)-1H-pyrazolo[4,3-c]quinoline (1.22)

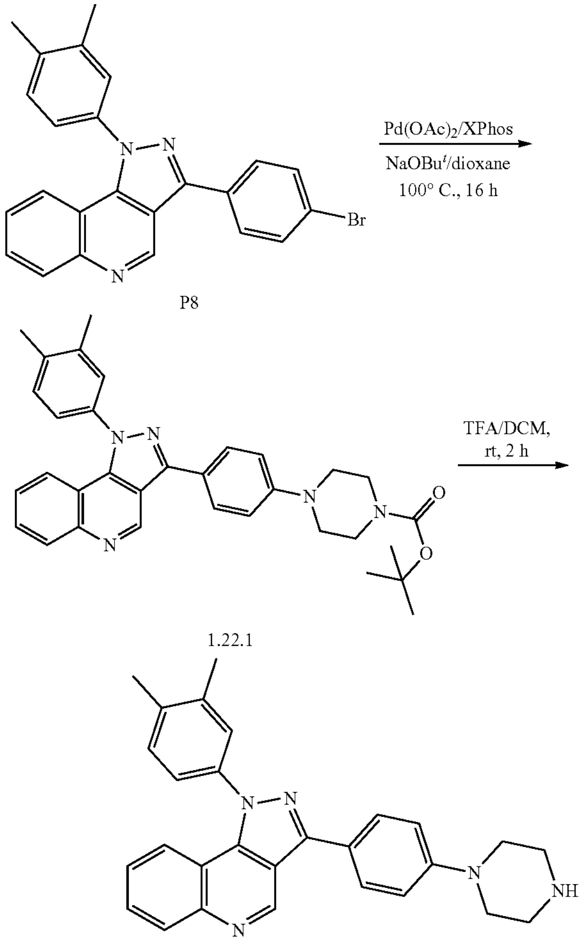

P8

1.22.1

1.22

The compound was synthesized according to the procedure described in Example 2 using 3-(4-bromophenyl)-1-(3,4-dimethylphenyl)-1H-pyrazolo[4,3-c]quinoline (P8) instead of 3-(3-bromophenyl)-1-(3,4-dimethylphenyl)-8-methoxy-1H-pyrazolo[4,3-c]quinoline and tert-butyl piperazine-1-carboxylate instead of 4-dimethylamino-piperidine. Yield 40% of tert-butyl 4-{4-[1-(3,4-dimethylphenyl)-1H-pyrazolo[4,3-c]quinolin-3-yl]phenyl}piperazine-1-carboxylate (1.22.1).

A mixture of 1.22.1 (50.0 mg, 0.094 mmol), DCM (1 mL), and TFA (0.3 mL) was stirred at ambient temperature for a 2 h, diluted with DCM (5 mL), washed with 10% aq. solution of $NaHCO_3$, water, dried under $Na_2SO_4$, and concentrated under reduced pressure. The residue was subjected to HPLC purification, obtained TFA salt was converted to HCl salt by treatment of its solution in DCM with excess of 3M solution of HCl in dioxane followed by dilution with $Et_2O$. Formed precipitate was separated by centrifugation, washed twice with $Et_2O$, and dried to afford 12.0 mg (28%) of the title compound 1.22. $^1H$-NMR (400 MHz, DMSO-d6) δ: 9.91 (s, 1H), 9.51 (br s, 2H), 8.50 (d, J=8.7 Hz, 1H), 8.07

(d, J=8.3 Hz, 2H), 7.99 (t, J=8.3 Hz, 1H), 7.73 (t, J=8.3 Hz, 1H), 7.63-7.56 (m, 2H), 7.43-7.37.526 (s, 2H), 7.20 (d, J=8.3 Hz, 2H), 3.61-3.50 (m, 4H), 3.29-3.17 (m, 4H), 2.43 (s, 3H), 2.37 (s, 3H).

Example 25: 2-{4-[1-(3,4-dimethylphenyl)-8-methoxy-1H-pyrazolo[4,3-c]quinolin-3-yl]-2-methoxyphenoxy}-N,N-dimethylethanamine (1.24)

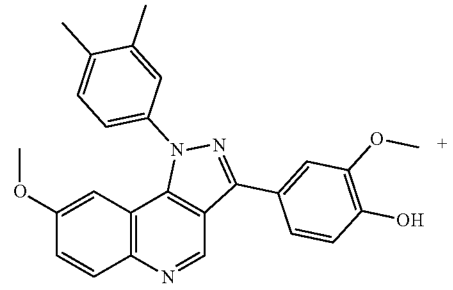

P8

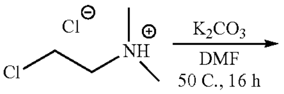

1.24.1

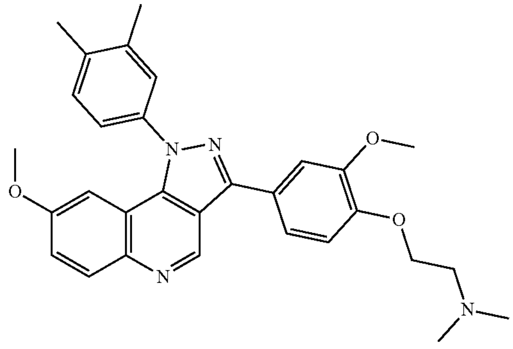

1.24

A mixture of 4-[1-(3,4-dimethylphenyl)-8-methoxy-1H-pyrazolo[4,3-c]quinolin-3-yl]-2-methoxyphenol (P10, 100 mg, 0.235 mmol), $K_2CO_3$ (83 mg, 0.600 mmol), (2-chloroethyl)dimethylamine hydrochloride (1.24.1) (44 mg, 0.305 mmol), and DMF (1 mL) was stirred at 50° C. for a 16 h, cooled to ambient temperature, and diluted with water (10 mL). Formed precipitate was filtered off, washed with water, $Et_2O$ and dried on air at 50° C. to afford 48 mg (41%) of the title compound. $^1$H-NMR (400 MHz, DMSO-d6) δ: 9.41 (s, 1H), 8.17-8.02 (m, 1H), 7.69-7.34 (m, 6H), 7.25-7.13 (m, 1H), 6.86 (s, 1H), 4.22-4.05 (m, 2H), 3.88 (s, 3H), 3.53 (s, 3H), 2.78-2.60 (m, 2H), 2.40 (s, 3H), 2.37 (s, 3H), 2.24 (s, 6H).

Example 26: 1-(3,4-dimethylphenyl)-8-methoxy-3-[3-methoxy-4-(2-morpholin-4-ylethoxy)phenyl]-1H-pyrazolo[4,3-c]quinoline (1.25)

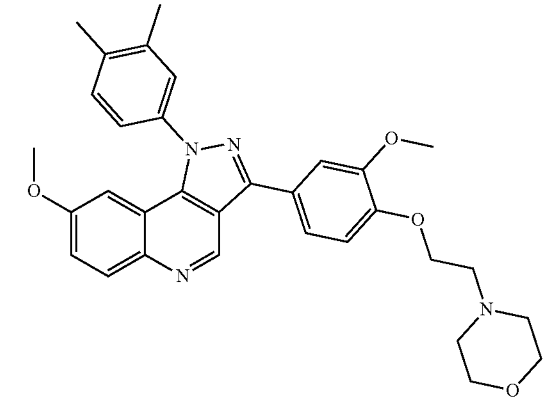 [SMILES: COc1ccc2ncc3c(-c4ccc(OCCN5CCOCC5)c(OC)c4)nn(-c4ccc(C)c(C)c4)c3c2c1]

The compound was synthesized according to the procedure described in Example 25 using 4-(2-chloroethyl)morpholine hydrochloride instead of (2-chloroethyl)dimethylamine. Yield 31%. $^1$H-NMR (400 MHz, DMSO-d6) δ: 9.41 (br, 1H), 8.11-8.08 (m, 1H), 7.66-7.38 (m, 6H), 7.21-7.19 (m, 1H), 6.87-6.86 (m, 1H), 4.19-4.15 (m, 2H), 3.88 (s, 3H), 3.61-3.58 (m, 4H), 3.53 (s, 3H), 2.77-2.72 (m, 2H), 2.54-2.36 (m, 10H).

Example 27: 1-(3,4-dimethylphenyl)-8-methoxy-3-[3-methoxy-4-(3-morpholin-4-ylpropoxy)phenyl]-1H-pyrazolo[4,3-c]quinoline (1.26)

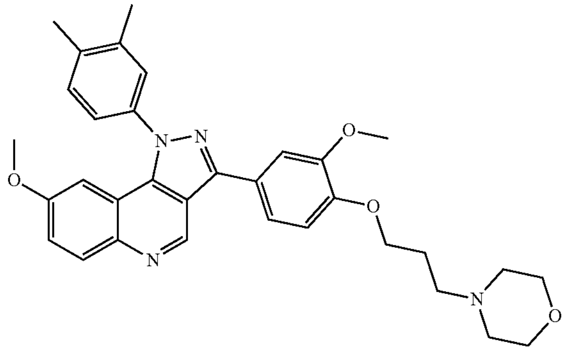 [SMILES: COc1ccc2ncc3c(-c4ccc(OCCCN5CCOCC5)c(OC)c4)nn(-c4ccc(C)c(C)c4)c3c2c1]

The compound was synthesized according to the procedure described in Example 25 using 4-(3-chloropropyl)morpholine hydrochloride instead of (2-chloroethyl)dimethylamine. Yield 21%. $^1$H-NMR (400 MHz, DMSO-d6) δ: 9.41 (br, 1H), 8.11-8.08 (m, 1H), 7.67-7.39 (m, 6H), 7.17-7.14 (m, 1H), 6.87-6.86 (m, 1H), 4.13-4.07 (m, 2H), 3.90-3.87 (m, 2H), 3.51-3.30 (m, 6H), 3.33-3.29 (m, 2H), 2.55-2.35 (m, 12H), 1.97-1.90 (m, 2H).

Example 28: 1-(3,4-dimethylphenyl)-8-methoxy-3-{4-methoxy-3-[2-(morpholin-4-yl)ethoxy]phenyl}-1H-pyrazolo[4,3-c]quinoline (1.43)

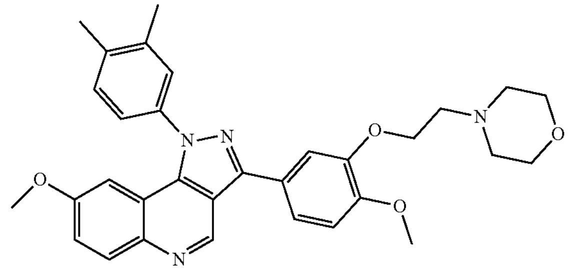 [SMILES: COc1ccc2ncc3c(-c4ccc(OC)c(OCCN5CCOCC5)c4)nn(-c4ccc(C)c(C)c4)c3c2c1]

The compound was synthesized according to the procedure described in Example 25 using 5-[1-(3,4-dimethylphenyl)-8-methoxy-1H-pyrazolo[4,3-c]quinolin-3-yl]-2-methoxyphenol (P27) instead of P10 and 4-(2-chloroethyl)morpholine hydrochloride instead of 1.24.1.

Example 29: 3-{4-methoxy-3-[2-(morpholin-4-yl)ethoxy]phenyl}-1-phenyl-1H-pyrazolo[4,3-c]quinoline (1.53)

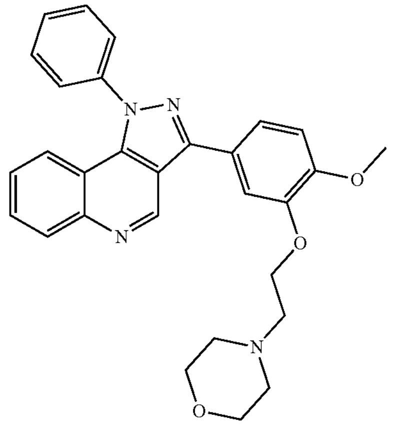 [SMILES: COc1ccc(-c2nn(-c3ccccc3)c3c2cnc2ccccc23)cc1OCCN1CCOCC1]

The compound was synthesized according to the procedure described in Example 25 using 2-methoxy-5-(1-phenyl-1H-pyrazolo[4,3-c]quinolin-3-yl)phenol (P32) instead of P10 and 4-(2-chloroethyl)morpholine hydrochloride instead of 1.24.1.

Example 30: 3-(1,3-benzodioxol-5-yl)-1-(3,4-dimethylphenyl)-1H-pyrazolo[4,3-c]quinoline (1.27)

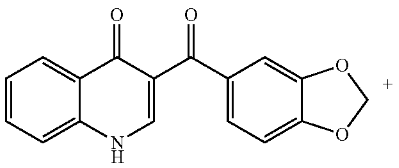

P11

-continued

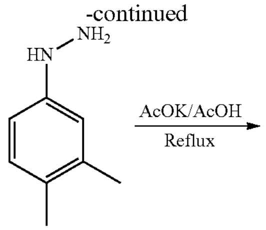

1.27.1

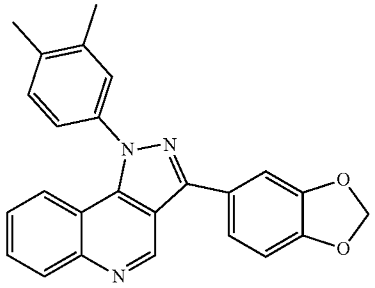

1.27

A mixture of 3-(1,3-benzodioxol-5-ylcarbonyl)quinolin-4(1H)-one (P11, 0.50 g, 1.40 mmol), 3,4-dimethylphenyl hydrazine hydrochloride (1.27.1) (0.295 g, 1.70 mmol), AcOK (0.170 g, 1.70 mmol), and AcOH (10 mL) was stirred and heated under reflux for 7 h and cooled to ambient temperature. Formed precipitate was filtered off and purified by re-crystallized from AcOH (10 mL) followed by washing with $Et_2O$ to afford 0.330 g (51%) of the title compound (1.27). $^1$H-NMR (400 MHz, DMSO-d6) δ: 9.52 (s, 1H), 8.18 (d, J=9.1 Hz, 1H), 7.75 (t, J=8.4 Hz, 1H), 7.63 (dd, $J_1$=8.1 Hz, $J_2$=1.7 Hz, 1H), 7.59-7.52 (m, 3H), 7.51-7.48 (m, 1H), 7.46 (s, 2H), 7.13 (d, J=7.9 Hz, 1H), 6.14 (s, 2H), 2.41 (s, 3H), 2.36 (s, 3H).

Example 31: 3-(1,3-benzodioxol-5-yl)-1-phenyl-1H-pyrazolo[4,3-c]quinoline (1.28)

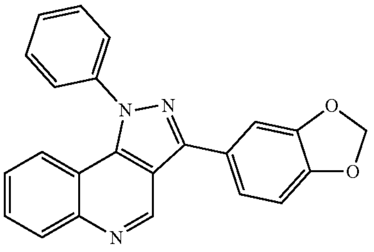 [SMILES: c1ccc(-n2nc(-c3ccc4c(c3)OCO4)c3cnc4ccccc4c32)cc1]

The compound was synthesized according to the procedure described in Example 30 using phenyl hydrazine hydrochloride instead of 1.27.1. $^1$H-NMR (400 MHz, DMSO-$d_6$) δ: 9.37 (s, 1H), 8.09 (d, J=9.0 Hz, 1H), 7.78-7.71 (m, 6H), 7.64 (d, J=6.5 Hz, 1H), 7.59 (s, 1H), 7.49-7.48 (m, 2H), 7.13 (d, J=8.2 Hz, 1H), 6.13 (s, 2H).

Example 32: 3-(1,3-benzodioxol-5-yl)-1-(3,4-dimethylphenyl)-8-methoxy-1H-pyrazolo[4,3-c]quinoline (1.29)

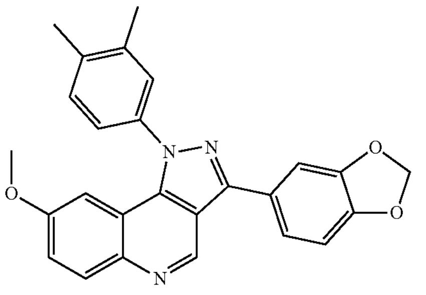 [SMILES: COc1ccc2ncc3c(-c4ccc5c(c4)OCO5)nn(-c4ccc(C)c(C)c4)c3c2c1]

The compound was synthesized according to the procedure described in Example 30 using 3-(1,3-benzodioxol-5-ylcarbonyl)-6-methoxyquinolin-4(1H)-one (P12) instead of P11. $^1$H-NMR (400 MHz, DMSO-$d_6$) δ: 9.37 (s, 1H), 8.09 (d, J=9.6 Hz, 1H), 7.62 (d, J=7.7 Hz, 1H), 7.56 (d, J=9.2 Hz, 2H), 7.47 (s, 2H), 7.39 (dd, $J_1$=8.8 Hz, $J_2$=1.5 Hz, 1H), 7.12 (d, J=8.4 Hz, 1H), 6.89-6.85 (m, 1H), 6.13 (s, 2H), 3.54 (s, 3H), 2.40 (s, 3H), 2.36 (s, 3H).

Example 33: 3-(1,3-benzodioxol-5-yl)-8-methoxy-1-phenyl-1H-pyrazolo[4,3-c]quinoline (1.30)

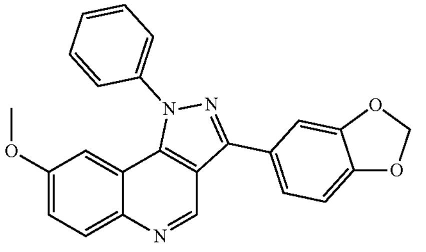 [SMILES: COc1ccc2ncc3c(-c4ccc5c(c4)OCO5)nn(-c4ccccc4)c3c2c1]

The compound was synthesized according to the procedure described in Example 30 using 3-(1,3-benzodioxol-5-ylcarbonyl)-6-methoxyquinolin-4(1H)-one (P12) instead of P11 and phenyl hydrazine hydrochloride instead of 1.27.1. $^1$H-NMR (400 MHz, DMSO-d6) δ: 9.37 (s, 1H), 8.09 (d, J=9.0 Hz, 1H), 7.78-7.71 (m, 5H), 7.63 (d, J=7.8 Hz, 1H), 7.58 (s, 1H), 7.40 (d, J=6.6 Hz, 1H), 7.13 (d, J=7.9 Hz, 1H), 6.81-6.80 (m, 1H), 6.13 (s, 2H), 3.52 (s, 3H).

Example 34: 3-(3,4-dimethoxyphenyl)-1-(1,2,3,4-tetrahydroisoquinolin-7-yl)-1H-pyrazolo[4,3-c]quinoline dihydrochloride (1.31)

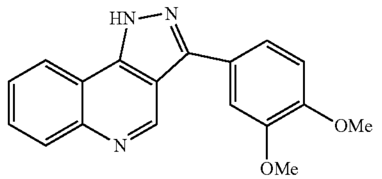

P23

+

-continued

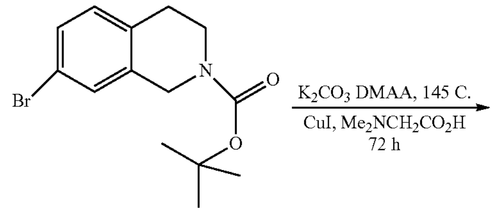

1.31.1

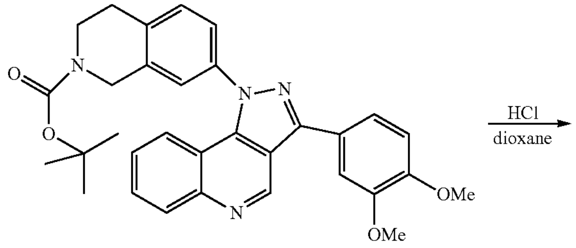

1.31.2

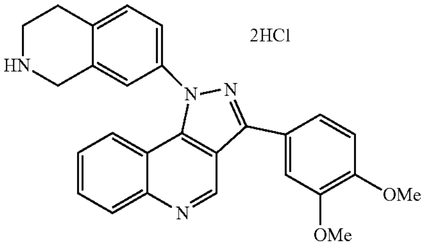

1.31

A mixture of 3-(3,4-dimethoxyphenyl)-1H-pyrazolo[4,3-c]quinoline (P23) (153 mg, 0.5 mmol), tert-butyl 7-bromo-3,4-dihydroisoquinoline-2(1H)-carboxylate (1.31.1) (172 mg, 0.55 mmol), $K_2CO_3$ (83 mg, 0.6 mmol), CuI (10 mg, 0.05 mmol), N,N-dimethylglycine (11 mg, 0.1 mmol), and DMAA (2 mL) was stirred under Ar at 145° C. for 72 h, cooled to ambient temperature, diluted with $CHCl_3$, washed with 1% aq. solution of $Na_2EDTA$, and concentrated under reduced pressure. The residue was subjected to HPLC to afford 87 mg (33%) of tert-Butyl 7-(3-(3,4-dimethoxyphenyl)-1H-pyrazolo[4,3-c]quinolin-1-yl)-3,4-dihydroisoquinoline-2(1H)-carboxylate (1.31.2). $^1$H NMR (400 MHz, DMSO-$d_6$): δ 9.57 (s, 1H), 8.19 (d, J=8.4 Hz, 1H), 7.77 (m, 1H), 7.69 (dd, $J_1$=8.0 Hz, $J_2$=1.6 Hz, 1H), 7.63 (s, 1H), 7.57 (m, 3H), 7.51 (m, 2H), 7.17 (d, J=8.4 Hz, 1H), 4.63 (s, 2H), 3.88 (s, 3H), 3.86 (s, 3H), 3.68 (m, 2H), 2.98 (m, 2H), 1.45 (s, 9H). LCMS (ESI) m/z 538 [MH]$^+$.

To a solution of 1.31.2 (45 mg, 0.084 mmol) in dioxane (2 mL) was added 3N solution of HCl in dioxane (2 mL), and the mixture was stirred for 4 h at ambient temperature. The formed precipitate was filtered off, washed with ether, and dried under reduced pressure at 50° C. to afford 40 mg (78%) of the title compound 3-(3,4-dimethoxyphenyl)-1-(1,2,3,4-tetrahydroisoquinolin-7-yl)-1H-pyrazolo[4,3-c]quinoline dihydrochloride (1.31). $^1$H NMR (400 MHz, DMSO-$d_6$): δ 9.93 (s, 1H), 9.80 (brs, 2H), 8.50 (d, J=8.4 Hz, 1H), 8.01 (t, J=7.6 Hz, 1H), 7.74 (m, 4H), 7.59-7.66 (m, 3H), 7.20 (d, J=7.6 Hz, 1H), 4.40 (m, 2H), 3.90 (s, 3H), 3.88 (s, 3H), 3.49 (m, 2H), 3.23 (t, J=6.0 Hz, 2H).

Example 35: 3-(3,4-dimethoxyphenyl)-1-(1,2,3,4-tetrahydroisoquinolin-6-yl)-1H-pyrazolo[4,3-c]quinoline dihydrochloride (1.32)

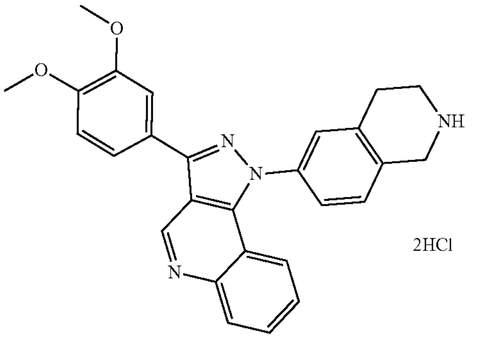 [SMILES: COc1ccc(-c2nn(-c3ccc4c(c3)CCNC4)c3c2cnc2ccccc23)cc1OC]

The compound was synthesized according to the procedure described in Example 34 using tert-butyl 6-bromo-3,4-dihydroisoquinoline-2(1H)-carboxylate instead of 1.31.1. $^1$H NMR (400 MHz, DMSO-$d_6$): δ 9.94 (s, 1H), 9.85 (brs, 2H), 8.53 (d, J=8.4 Hz, 1H), 8.02 (m, 1H), 7.70-7.78 (m, 4H), 7.60-7.65 (m, 3H), 7.20 (d, J=8.4 Hz, 1H), 4.47 (m, 2H), 3.90 (s, 3H), 3.88 (s, 3H), 3.46 (m, 2H), 3.18 (t, J=6.0 Hz, 2H).

Example 36: 1-(2,3-dihydro-1H-isoindol-5-yl)-3-(3,4-dimethoxyphenyl)-1H-pyrazolo[4,3-c]quinoline dihydrochloride (1.33)

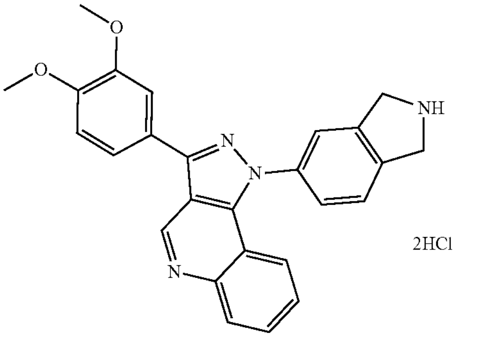 [SMILES: COc1ccc(-c2nn(-c3ccc4c(c3)CNC4)c3c2cnc2ccccc23)cc1OC]

The compound was synthesized according to the procedure described in Example 34 using tert-butyl 5-bromo-1,3-dihydro-2H-isoindole-2-carboxylate instead of 1.31.1. $^1$H NMR (400 MHz, DMSO-$d_6$): δ 10.27 (brs, 2H), 9.93 (s, 1H), 8.49 (d, J=8.4 Hz, 1H), 8.00 (t, J=7.6 Hz, 1H), 7.89 (s, 1H), 7.83 (d, J=8.4 Hz, 1H), 7.77 (m, 2H), 7.71 (t, J=7.6 Hz, 1H), 7.61 (m, 2H), 7.20 (d, J=8.0 Hz, 1H), 4.69 (m, 4H), 3.90 (s, 3H), 3.88 (s, 3H).

Example 37: 3-(3,4-dimethoxyphenyl)-8-methoxy-1-(1,2,3,4-tetrahydroisoquinolin-7-yl)-1H-pyrazolo[4,3-c]quinoline dihydrochloride (1.34)

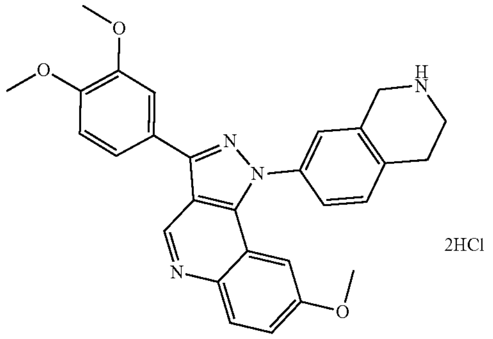 [SMILES: COc1ccc2ncc3c(-c4ccc(OC)c(OC)c4)nn(-c4ccc5c(c4)CNCC5)c3c2c1]

The compound was synthesized according to the procedure described in Example 34 using 3-(3,4-dimethoxyphenyl)-8-methoxy-1H-pyrazolo[4,3-c]quinoline (P24) instead of P23. $^1$H NMR (400 MHz, DMSO-$d_6$): δ 9.82 (brs, 2H), 9.80 (s, 1H), 8.43 (d, J=9.2 Hz, 1H), 7.75 (m, 3H), 7.59-7.67 (m, 3H), 7.19 (d, J=8.4 Hz, 1H), 6.87 (d, J=2.8 Hz, 1H), 4.41 (m, 2H), 3.89 (s, 3H), 3.87 (s, 3H), 3.62 (s, 3H), 3.47 (m, 2H), 3.22 (m, 2H).

Example 38: 3-(3,4-dimethoxyphenyl)-8-methoxy-1-(1,2,3,4-tetrahydroisoquinolin-6-yl)-1H-pyrazolo[4,3-c]quinoline dihydrochloride (1.35)

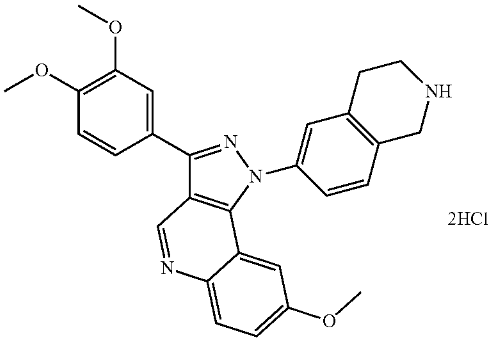 [SMILES: COc1ccc2ncc3c(-c4ccc(OC)c(OC)c4)nn(-c4ccc5c(c4)CCNC5)c3c2c1]

The compound was synthesized according to the procedure described in Example 34 using 3-(3,4-dimethoxyphenyl)-8-methoxy-1H-pyrazolo[4,3-c]quinoline (P24) instead of P23 and tert-butyl 6-bromo-3,4-dihydroisoquinoline-2(1H)-carboxylate instead of 1.31.1. $^1$H NMR (400 MHz, DMSO-$d_6$): δ 9.90 (brs, 2H), 9.80 (s, 1H), 8.45 (d, J=9.2 Hz, 1H), 7.74 (m, 3H), 7.66 (dd, $J_1$=9.2 Hz, $J_2$=2.4 Hz, 1H), 7.63 (d, J=8.0 Hz, 1H), 7.59 (d, J=1.6 Hz, 1H), 7.19 (d, J=8.4 Hz, 1H), 6.91 (d, J=2.4 Hz, 1H), 4.46 (m, 2H), 3.89 (s, 3H), 3.87 (s, 3H), 3.61 (s, 3H), 3.45 (m, 2H), 3.18 (m, 2H).

Example 39: 1-(2,3-dihydro-1H-isoindol-5-yl)-3-(3,4-dimethoxyphenyl)-8-methoxy-1H-pyrazolo[4,3-c]quinoline dihydrochloride (1.36)

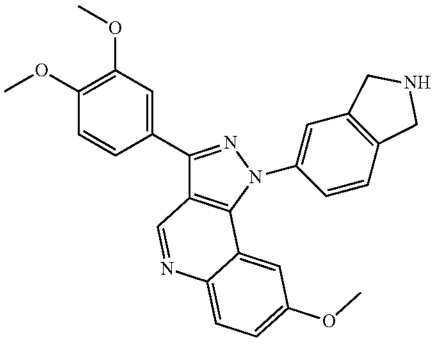

2HCl

The compound was synthesized according to the procedure described in Example 34 using 3-(3,4-dimethoxyphenyl)-8-methoxy-1H-pyrazolo[4,3-c]quinoline (P24) instead of P23 and tert-butyl 5-bromo-1,3-dihydro-2H-isoindole-2-carboxylate instead of 1.31.1. $^1$H NMR (400 MHz, DMSO-$d_6$): δ 10.25 (brs, 2H), 9.79 (s, 1H), 8.41 (d, J=9.2 Hz, 1H), 7.90 (s, 1H), 7.84 (d, J=8.4 Hz, 1H), 7.79 (d, J=8.0 Hz, 1H), 7.75 (dd, $J_1$=8.4 Hz, $J_2$=1.6 Hz, 1H), 7.65 (m, 1H), 7.59 (d, J=1.6 Hz, 1H), 7.19 (d, J=8.4 Hz, 1H), 6.86 (d, J=2.8 Hz, 1H), 4.68 (m, 4H), 3.89 (s, 3H), 3.88 (s, 3H), 3.60 (s, 3H).

Example 40: 3-(3,4-dimethoxyphenyl)-6-methoxy-1-(1,2,3,4-tetrahydroisoquinolin-7-yl)-1H-pyrazolo[4,3-c]quinoline dihydrochloride (1.37)

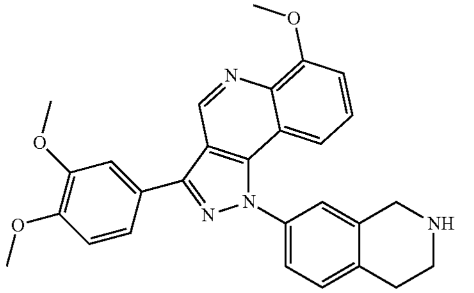

2HCl

The compound was synthesized according to the procedure described in Example 34 using 3-(3,4-dimethoxyphenyl)-6-methoxy-1H-pyrazolo[4,3-c]quinoline (P25) instead of P23. $^1$H NMR (400 MHz, DMSO-$d_6$): δ 9.67 (brs, 2H), 9.60 (s, 1H), 7.70 (m, 3H), 7.57-7.66 (m, 3H), 7.53 (d, J=8.0 Hz, 1H), 7.22 (d, J=8.8 Hz, 1H), 7.16 (d, J=8.4 Hz, 1H), 4.40 (m, 2H), 4.12 (s, 3H), 3.89 (s, 3H), 3.88 (s, 3H), 3.49 (m, 2H), 3.22 (m, 2H).

Example 41: 3-(3,4-dimethoxyphenyl)-6-methoxy-1-(1,2,3,4-tetrahydroisoquinolin-6-yl)-1H-pyrazolo[4,3-c]quinoline dihydrochloride (1.38)

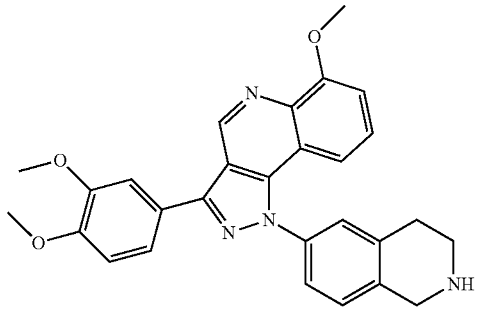

2HCl

The compound was synthesized according to the procedure described in Example 34 using 3-(3,4-dimethoxyphenyl)-6-methoxy-1H-pyrazolo[4,3-c]quinoline (P25) instead of P23 and tert-butyl 6-bromo-3,4-dihydroisoquinoline-2(1H)-carboxylate instead of 1.31.1. $^1$H NMR (400 MHz, DMSO-$d_6$): δ 9.90 (brs, 2H), 9.61 (s, 1H), 7.55-7.73 (m, 7H), 7.22 (d, J=8.4 Hz, 1H), 7.16 (d, J=8.4 Hz, 1H), 4.46 (m, 2H), 4.13 (s, 3H), 3.88 (s, 3H), 3.88 (s, 3H), 3.45 (m, 2H), 3.17 (t, J=6.0 Hz, 2H).

Example 42: 1-(2,3-dihydro-1H-isoindol-5-yl)-3-(3,4-dimethoxyphenyl)-6-methoxy-1H-pyrazolo[4,3-c]quinoline dihydrochloride (1.39)

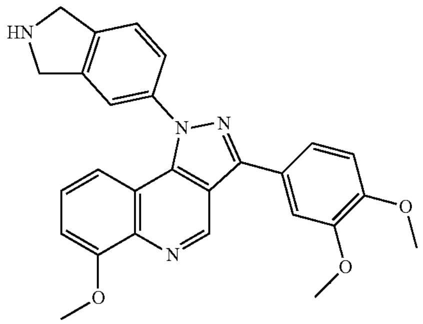 [SMILES: COc1ccc(-c2nn(-c3ccc4c(c3)CNC4)c3c2cnc2c(OC)cccc23)cc1OC]

The compound was synthesized according to the procedure described in Example 34 using 3-(3,4-dimethoxyphenyl)-6-methoxy-1H-pyrazolo[4,3-c]quinoline (P25) instead P23 and tert-butyl 5-bromo-1,3-dihydro-2H-isoindole-2-carboxylate instead 1.31.1. $^1$H NMR (400 MHz, DMSO-d6): δ 10.32 (m, 2H), 9.61 (s, 1H), 7.88 (s, 1H), 7.75-7.81 (m, 2H), 7.73 (dd, $J_1$=8.4 Hz, $J_2$=2.0 Hz, 1H), 7.65 (t, J=8.4 Hz, 1H), 7.58 (d, J=2.0 Hz, 1H), 7.56 (d, J=8.4 Hz, 1H), 7.23 (d, J=8.4 Hz, 1H), 7.14 (dd, $J_1$=8.4 Hz, $J_2$=0.8 Hz, 1H), 4.68 (m, 4H), 4.13 (s, 3H), 3.88 (s, 3H), 3.88 (s, 3H).

Biological Assays

Example A. Primary Assay used to determine potency of HPK1 enzymatic activity inhibition. Compound activity was determined using recombinant HPK1 protein and MBP Substrate (both Promega, Cat #V6398) in an in vitro enzymatic reaction. The enzymatic assay used to determine activity was a Luminescence assay using a Microplate Reader ClarioStar Plus. The enzymatic reaction was carried out in assay buffer (40 mM TRIS-HCl pH 7.4-7.6, 20 mM $MgCl_2$, 0.05 mM DTT, 0.1 mg/ml BSA). The compounds were dispensed on a 384 well Diamond Well Plate (Axigen, Cat #P-384-120SQ-C—S) using the Biomek FX liquid handling system at 100× solutions of compounds in DMSO. 2×HPK1-MBP mix (final concentration 0.64 ng/μl of HPK1 and 45 ng/μl of MBP) was prepared in 1× Assay buffer and 5.5 μl of mixture per well was added into 384 w white Reaction plate with NBS (Corning, Cat #4513). 5.5 μl of MBP substrate w/o HPK1 in 1× buffer was used for negative control. Plates were centrifuged for 1 min at 100 g. Next step the Compounds were added to Reaction plate using Biomek station via following steps: 11 of 100× compounds (in DMSO) were mixed thoroughly with 49 ul of 2×10 uM ATP in Assay Buffer, then 5.5 μl of this mixture was added to Reaction plate with 5.5 μl of HPK1-MBP mix. Plates were centrifuged for 1 min at 100 g and incubated for 1 hour at room temperature. Next 3 μL of ADP-Glo reagent (Promega, ADP-Glo™ Kinase Assay, Cat #V9102) per well was added. Plates were incubated for 30 minutes at room temperature. Then 6 μL of Kinase detection reagent (Promega, ADP-Glo™ Kinase Assay, Cat #V9102) per well was added and the Luminescence was measured using Microplate Reader. The % inhibition was then used to calculate the $IC_{50}$ values. The Ki values are shown in Table A, wherein "A" corresponds to Ki<10.0 nM, "B" corresponds to 10.0 nM≤Ki<20.0 nM, "C" 20.0 nM≤Ki<50.0 nM, and "D" corresponds to 50.0 nM≤Ki.

TABLE A

Primary HPK1 inhibition

| Compound # | HPK1 Ki |
|---|---|
| 1.1 | B |
| 1.3 | B |
| 1.14 | A |
| 1.16 | B |
| 1.17 | B |
| 1.18 | C |
| 1.21 | D |
| 1.22 | D |
| 1.24 | B |
| 1.25 | C |
| 1.26 | C |
| 1.35 | A |
| 1.36 | A |

Example B. MV4-11 Cytotoxicity Assay. CC50 was determined using MV4-11 cell lines in RPMI-1640 culture medium (PanEco cat #C363). Compounds were prepared as 200× stocks with serial dilution in 100% DMSO with a final concentration of 1×. Dispersed 40 μL in 384-well plates at a concentration of 4000 cells per well using a robotic station Biomek (Beckman). Before adding compounds, the cells were incubated at 37° C. A dilution plate was prepared by pouring 78 μl of the appropriate culture medium using a robotic station Biomek (Beckman). Sequentially, using a robotic station, 2 μl of substances were taken and added to 78 μl of culture medium (dilution of compounds 40×). Took from there 10 μl and added to the plates to the cells (dilution of compounds 5×). The plates were incubated for 3 days at a temperature 37° C. After 3 days, 10 μl of CellTiter-Glo (Promega) was added to the cells and the luminescence was measured. The $CC_{50}$ values are shown in Table B, wherein "A" corresponds to $CC_{50}$<50.0 nM, "B" corresponds to 50.0 nM≤$CC_{50}$<100.0 nM, "C" 100.0 nM≤$CC_{50}$<500.0 nM, and "D" corresponds to 500.0 nM≤$CC_{50}$.

TABLE B

MV4-11 Cytotoxicity

| Compound # | MV4-11, $CC_{50}$ |
|---|---|
| 1.1 | D |
| 1.3 | C |
| 1.14 | D |
| 1.16 | B |
| 1.17 | B |
| 1.18 | C |
| 1.21 | C |
| 1.22 | C |
| 1.24 | A |
| 1.25 | C |
| 1.26 | B |

Example C. MOLM-13 Cytotoxicity Assay. Assay was performed according the procedure described in O. A. Elgamal et al. *J. Hematol. Oncol.* 2020, 13, 8 (https://doi.org/10.1186/s13045-019-0821-7). The $CC_{50}$ values are shown in Table C, wherein "A" corresponds to $CC_{50}$<500.0 nM, "B" corresponds to 500.0 nM≤$CC_{50}$<1000.0 nM, "C" 1000.0 nM≤$CC_{50}$<5000.0 nM, and "D" corresponds to 5000.0 nM≤$CC_{50}$.

TABLE C

MOLM-13 Cytotoxicity

| Compound # | MOLM-13, $CC_{50}$ |
|---|---|
| 1.1 | C |
| 1.3 | D |
| 1.16 | A |
| 1.18 | D |
| 1.21 | C |
| 1.22 | C |
| 1.24 | A |
| 1.25 | C |
| 1.26 | B |

Example D. FLT3 inhibitory activity and cytotoxicity. This assay was used to determine potency of FLT3 enzymatic activity inhibition. Corresponding biochemical inhibition of enzymatic activities of FLT3 (wt), FLT3 (D835Y), and FLT3 (ITD) were measured using recombinant protein constructs of kinase domains via activity based FLT3 kinase assay for compound screening and profiling via radiometric HotSpot™ kinase assay (Reaction Biology). Peptide substrate [EAIYAAPFAKKK]. Compounds were dissolved to 10 mM in DMSO. Compounds were tested in 10-dose IC50 mode with a 3-fold serial dilution starting at 0.3 μM. Control compound, Staurosporine, was tested in 10-dose IC50 mode with 4-fold serial dilution starting at 20 μM. Alternate control compounds were tested in 10-dose IC50 mode with 3-fold serial dilution starting at 20 μM. Reactions were carried out at 1 μM ATP. The estimated Ki values were calculated by using the formula presented below, which is applicable for ATP competitive inhibitors: Ki=IC50/(1+[S]/Km). The Ki values are shown in Table D, wherein "A" corresponds to Ki<0.5 nM, "B" corresponds to 0.5 nM≤Ki<2.0 nM, "C" 2.0 nM≤Ki<5.0 nM, and "D" corresponds to 5.0 nM≤Ki. In Table E shown HEK293 cytotoxicity.

TABLE D

FLT3 inhibitory activity of substituted 1H-pyrazolo [4,3-c] quinolines of formula I(A-G).

| | Ki, nM | | |
|---|---|---|---|
| | FLT3 (wt) | FLT3 (D835Y) Gilteretinib | FLT3 (ITD) |
| Compound # | 6.3* | 12.98* | 2* |
| 1.31 | A | A | B |
| 1.32 | B | B | D |
| 1.33 | B | A | C |
| 1.34 | A | A | A |
| 1.35 | A | A | B |
| 1.36 | A | A | B |

*Data from publication CN111646978(A)

TABLE E

HEK293 cytotoxicity. The $CC_{50}$ values are shown in Table E, wherein "A" corresponds to $CC_{50}$ < 10.0 μM, "B" corresponds to 10.0 nM ≤ $CC_{50}$ < 50.0 μM, and "C" corresponds to 50.0 μM ≤ $CC_{50}$.

| Compound # | HEK293, $CC_{50}$ |
|---|---|
| 1.31 | A |
| 1.32 | B |
| 1.33 | C |
| 1.35 | A |
| 1.36 | A |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of Formula I-A:

(I-A)

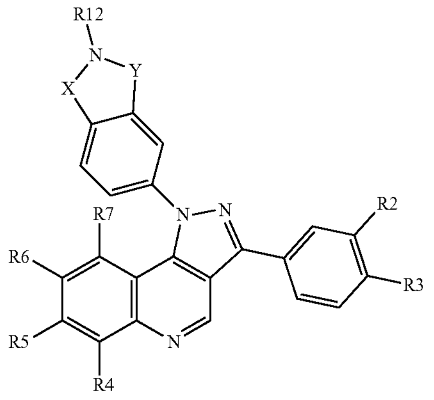

or a pharmaceutically acceptable salt, solvate, enantiomer, stereoisomer, or a tautomer thereof, wherein:

X is selected from $—CH_2—$, $—(CH_2)_2—$, and $—(CH_2)_3—$;

Y is selected from $—CH_2—$, $—(CH_2)_2—$, and $—(CH_2)_3—$; and

R2-R7 and R12 are each independently selected from H, halogen, $—C_{1-6}$alkyl, $—C_{1-6}$alkoxy, $—C_{1-6}$haloalkyl, and $—C_{1-6}$haloalkoxy.

2. A compound selected from:

7-[3-(3,4-dimethoxyphenyl)-1H-pyrazolo[4,3-c]quinolin-1-yl]-1,2,3,4-tetrahydroisoquinoline;

6-[3-(3,4-dimethoxyphenyl)-1H-pyrazolo[4,3-c]quinolin-1-yl]-1,2,3,4-tetrahydroisoquinoline;

5-[3-(3,4-dimethoxyphenyl)-1H-pyrazolo[4,3-c]quinolin-1-yl]-2,3-dihydro-1H-isoindole;

7-[3-(3,4-dimethoxyphenyl)-8-methoxy-1H-pyrazolo[4,3-c]quinolin-1-yl]-1,2,3,4-tetrahydroisoquinoline;

6-[3-(3,4-dimethoxyphenyl)-8-methoxy-1H-pyrazolo[4,3-c]quinolin-1-yl]-1,2,3,4-tetrahydroisoquinoline;

5-[3-(3,4-dimethoxyphenyl)-8-methoxy-1H-pyrazolo[4,3-c]quinolin-1-yl]-2,3-dihydro-1H-isoindole;

7-[3-(3,4-dimethoxyphenyl)-6-methoxy-1H-pyrazolo[4,3-c]quinolin-1-yl]-1,2,3,4-tetrahydroisoquinoline;

6-[3-(3,4-dimethoxyphenyl)-6-methoxy-1H-pyrazolo[4,3-c]quinolin-1-yl]-1,2,3,4-tetrahydroisoquinoline;

5-[3-(3,4-dimethoxyphenyl)-6-methoxy-1H-pyrazolo[4,3-c]quinolin-1-yl]-2,3-dihydro-1H-isoindole;

or a pharmaceutically acceptable salt, solvate, stereoisomer, or tautomer thereof.

3. A pharmaceutical composition comprising the compound of a pharmaceutically acceptable salt, solvate, stereoisomer, or tautomer thereof of claim 1, and a pharmaceutically acceptable carrier.

4. The pharmaceutical composition of claim 3, further comprising an additional pharmaceutically active agent.

5. A pharmaceutical composition comprising the compound of a pharmaceutically acceptable salt, solvate, stereoisomer, or tautomer thereof of claim 2, and a pharmaceutically acceptable carrier.

6. The pharmaceutical composition of claim 5, further comprising an additional pharmaceutically active agent.

* * * * *